(12) United States Patent
Flohr et al.

(10) Patent No.: US 7,160,875 B2
(45) Date of Patent: Jan. 9, 2007

(54) MALONAMIDE DERIVATIVES

(75) Inventors: Alexander Flohr, Basel (CH); Guido Galley, Rheinfelden (DE); Roland Jakob-Roetne, Inzlingen (DE); Eric Argirios Kitas, Aesch (CH); Jens-Uwe Peters, Grenzach-Wyhlen (DE); Wolfgang Wostl, Grenzach-Wyhlen (DE)

(73) Assignee: Hoffmann-La Rache Inc., Nutley, NJ (US)

( * ) Notice: Subject to any disclaimer, the term of this patent is extended or adjusted under 35 U.S.C. 154(b) by 178 days.

(21) Appl. No.: 10/933,177

(22) Filed: Sep. 2, 2004

(65) Prior Publication Data

US 2005/0054633 A1 Mar. 10, 2005

(30) Foreign Application Priority Data

Sep. 9, 2003 (EP) .................................. 03019683

(51) Int. Cl.
*C07D 243/12* (2006.01)
*C07D 487/00* (2006.01)
*C07D 313/00* (2006.01)
*A61K 31/55* (2006.01)
*A61P 25/28* (2006.01)

(52) U.S. Cl. ..................... 514/212.04; 514/212.07; 514/221; 514/450; 540/517; 540/522; 540/523; 549/354

(58) Field of Classification Search ................ 540/517, 540/522, 523; 549/354; 514/212.07, 221, 514/450, 212.04
See application file for complete search history.

(56) References Cited

FOREIGN PATENT DOCUMENTS

WO WO 01/77086 A1 10/2001
WO WO 01/90084 A1 11/2001

OTHER PUBLICATIONS

Sisodia, S. et al., Nature Reviews/Neuroscience vol. 3, Apr. (2002) pp. 281-290.
Beher, D. et al., Biochemical Society Transactions (2002), vol. 30, Part 4, pp. 534-537.
Wolfe, M. S., Current Topics in Medicinal Chemistry, (2002), vol. 2, pp. 371-383.
Tsai, J. Y. et al., Current Medicinal Chemistry (2002) vol. 9, No. 11, pp. 1087-1106.
Sambamurti, K. et al., Drug Development Research vol. 56 (2002), pp. 211-227.
May, P. C., Drug Discovery Today, vol. 6, No. 9 (2001) pp. 459-462.
Nunan, J. et al., FEBS Letters vol. 483 (2000) pp. 6-10.
Hardy, J. et al., Science, vol. 297 (2002) pp. 353-356.
Wolfe, M. S., Journal of Medicinal Chemistry vol. 44, No. 13 (2001) pp. 2039-2060.
Brockhaus, M. et al., Neuroreport vol. 9(7) (1998) pp. 1481-1486.

*Primary Examiner*—Bruce Kifle
(74) *Attorney, Agent, or Firm*—George W. Johnston; Patricia S. Rocha-Tramaloni; Kimberly J. Prior

(57) ABSTRACT

The invention relates to malonamide derivatives of formula

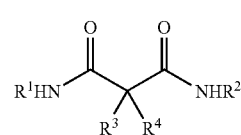

I wherein each of the variables are as defined herein and to pharmaceutically acceptable acid addition salts, optically pure enantiomers, racemates and diastereomeric mixtures thereof. These compounds are γ-secretase inhibitors and may be used for the treatment of Alzheimer's disease.

24 Claims, No Drawings

MALONAMIDE DERIVATIVES

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch.

The γ-secretase activity is absolutely required for the production of Abeta peptides. This has been shown both by genetic means, i.e., ablation of the presenilin genes and by low-molecular-weight inhibitory compounds. Since according to the amyloid hypothesis or AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:
Nature Reviews/Neuroscience, Vol. 3, April 2002/281,
Biochemical Society Transactions (2002), Vol. 30. part 4,
Current Topics in Medicinal Chemistry, 2002, 2, 371–383,
Current Medicinal Chemistry, 2002, Vol. 9, No. 11, 1087–1106,
Drug Development Research, 56, 211–227, 2002,
Drug Discovery Today, Vol. 6, No. 9, May 2001, 459–462,
FEBS Letters, 483, (2000), 6–10,
Science, Vol. 297, 353–356, July 2002 and
Journ. of Medicinal Chemistry, Vol. 44, No. 13, 2001, 2039–2060.

SUMMARY OF THE INVENTION

The present invention provides compounds of formula I per se and pharmaceutically acceptable acid addition salts of compounds of formula I, as well as methods for manufacturing such compounds. The invention further provides all forms of optically pure enantiomers, recemates or diastereomeric mixtures for compounds of formula I.

The invention also provides compositions containing compounds of the invention and a pharmaceutically acceptable carrier and a method for the preparation of such compositions.

The compounds of the invention are γ-secretase inhibitors and will be useful in treating AD by blocking the activity of γ-secretase and reducing or preventing the formation of the various amyloidogenic Abeta peptides. Thus, the invention further provides methods for the treatment of diseases related to γ-secretase inhibition, as well as the methods for the control and prevention of Alzheimer's disease by administering compounds of formula I or pharmaceutically acceptable acid addition salts thereof.

In particular, the invention provides malonamide derivatives of formula

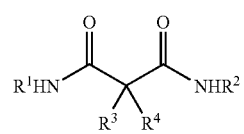

I wherein
$R^1$ is selected from a)

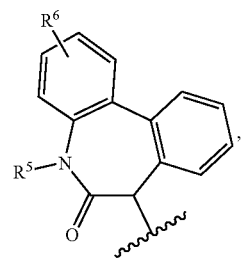

b)

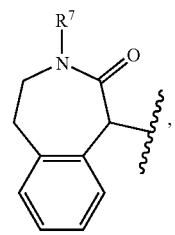

c)

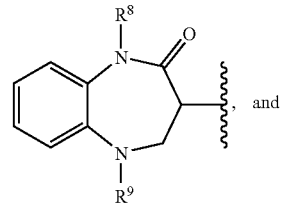

, and

-continued d)

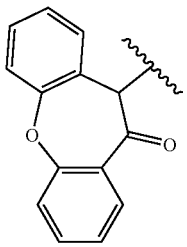

R² is lower alkyl, lower alkinyl, —(CH₂)ₙ—O-lower alkyl, —(CH₂)ₙ—S-lower alkyl, —(CH₂)ₙ—CN, —(CR'R")ₙ—CF₃, —(CR'R")ₙ—CHF₂, —(CR'R")ₙ—CH₂F, —(CH₂)ₙ—C(O)O-lower alkyl, —(CH₂)ₙ-halogen, or is —(CH₂)ₙ-cycloalkyl optionally substituted by one or more substituents selected from the group consisting of phenyl, halogen and CF₃;

R',R" are each independently hydrogen, lower alkyl, lower alkoxy, halogen or hydroxy;

R³, R⁴ are each independently hydrogen, lower alkyl, lower alkoxy, phenyl or halogen;

R⁵ is hydrogen, lower alkyl, —(CH₂)ₙ—CF₃ or —(CH₂)ₙ-cycloalkyl;

R⁶ is hydrogen or halogen;

R⁷ is hydrogen or lower alkyl;

R⁸ is hydrogen, lower alkyl, lower alkinyl, —(CH₂)ₙ—CF₃, —(CH₂)ₙ-cycloalkyl or —(CH₂)ₙ-phenyl optionally substituted by halogen;

R⁹ is hydrogen, lower alkyl, —C(O)H, —C(O)-lower alkyl, —C(O)—CF₃, —C(O)—CH₂F, —C(O)—CHF₂, —C(O)-cycloalkyl, —C(O)—(CH₂)ₙ—O-lower alkyl, —C(O)O—(CH₂)ₙ-cycloalkyl, —C(O)-phenyl optionally substituted by one or more substituents selected from the group consisting of halogen and —C(O)O-lower alkyl, or is —S(O)₂-lower alkyl, —S(O)₂—CF₃, —(CH₂)ₙ-cycloalkyl or is —(CH₂)ₙ-phenyl optionally substituted by halogen;

n is 0, 1, 2, 3 or 4;

or a pharmaceutically acceptable acid addition salt, optically pure enantiomer, racemate or diastereomeric mixture thereof.

DETAILED DESCRIPTION OF THE INVENTION

In one aspect, the invention provides malonamide derivatives of formula

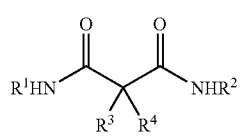

I wherein
R¹ is selected from a)

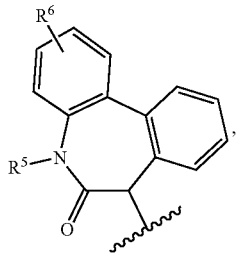

b)

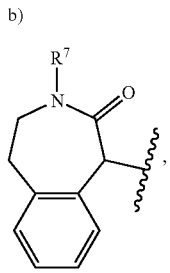

c)

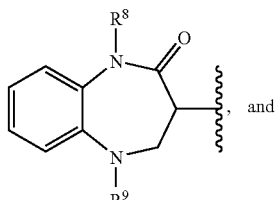
, and d)

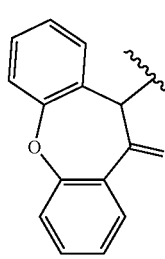

R² is lower alkyl, lower alkinyl, —(CH₂)ₙ—O-lower alkyl, —(CH₂)ₙ—S-lower alkyl, —(CH₂)ₙ—CN, —(CR'R")ₙ—CF₃, —(CR'R")ₙ—CHF₂, —(CR'R")ₙ—CH₂F, —(CH₂)ₙ, —C(O)O-lower alkyl, —(CH₂)ₙ-halogen, or is —(CH₂)ₙ-cycloalkyl optionally substituted by one or more substituents selected from the group consisting of phenyl, halogen and CF₃;

R',R" are each independently hydrogen, lower alkyl, lower alkoxy, halogen or hydroxy;

R³, R⁴ are each independently hydrogen, lower alkyl, lower alkoxy, phenyl or halogen;

R⁵ is hydrogen, lower alkyl, —(CH₂)ₙ—CF₃ or —(CH₂)ₙ-cycloalkyl;

R⁶ is hydrogen or halogen;

R⁷ is hydrogen or lower alkyl;

R⁸ is hydrogen, lower alkyl, lower alkinyl, —(CH₂)ₙ—CF₃, —(CH₂)ₙ-cycloalkyl or —(CH₂)ₙ-phenyl optionally substituted by halogen;

R⁹ is hydrogen, lower alkyl, —C(O)H, —C(O)-lower alkyl, —C(O)—CF₃, —C(O)—CH₂F, —C(O)—CHF₂, —C(O)-cycloalkyl, —C(O)—(CH₂)ₙ—O-lower alkyl, —C(O)O—(CH₂)ₙ-cycloalkyl, —C(O)-phenyl optionally substituted by one or more substituents selected from the group consisting of halogen and —C(O)O-lower alkyl, or is —S(O)$_2$-lower alkyl, —S(O)$_2$—CF$_3$, —(CH$_2$)$_n$-cycloalkyl or is —(CH$_2$)$_n$— phenyl optionally substituted by halogen;

n is 0, 1, 2, 3 or 4;

or a pharmaceutically acceptable acid addition salt, optically pure enantiomer, racemate or diastereomeric mixture thereof.

As used herein, the term "lower alkyl" denotes a saturated straight- or branched-chain alkyl group containing from 1 to 7 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkinyl" denotes a unsaturated straight- or branched-carbon chain containing from 2 to 7 carbon atoms and containing at least one triple bond.

The term "cycloalkyl" denotes a saturated carbocyclic group, containing 3–7 carbon atoms.

The term "halogen" denotes chlorine, iodine, fluorine and bromine.

The term "lower alkoxy" denotes a group wherein the alkyl residues is as defined above, and which is attached via an oxygen atom.

The expression "(CR'R")$_n$" can be, for example —CH$_2$—, —CH$_2$—CH$_2$—, —CH$_2$—CH$_2$—CH$_2$—, —CH$_2$—CF$_2$—, —CH$_2$—CH$_2$—CF$_2$—, —CH$_2$—CH$_2$—CH(OCH$_3$)—, —CH$_2$CH(OH)— or —C(CH$_3$)$_2$—CH(OH)—.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those, wherein R' is a). In particular, preferred compounds are those of formula I, wherein R' is a) and R$^2$ is —(CH$_2$)$_n$-cycloalkyl, optionally substituted by CF$_3$, for example the following compounds:
N-cyclopropylmethyl-2-methyl-N'-(5-methyl-6-oxo-6,7-dihydro-5H-dibenzo[b,d]azepin-7-yl)-malonamide or
2-fluoro-2-methyl-N-(5-methyl-6-oxo-6,7-dihydro-5H-dibenzo[b,d]azepin-7-yl)-N'-(1-trifluoromethyl-cyclopropylmethyl)-malonamide.

Preferred compounds are further those, wherein R' is a) and R$^2$ is lower alkyl, —(CH$_2$)$_n$—O-lower alkyl or —(CH$_2$)$_n$ —S-lower alkyl, for example the following compounds:
2-methyl-N-(5-methyl-6-oxo-6,7-dihydro-5H-dibenzo[b,d]azepin-7-yl)-N'-(2-methoxyethyl)-malonamide,
2-methyl-N-(5-methyl-6-oxo-6,7-dihydro-5H-dibenzo[b,d]azepin-7-yl)-N'-(2-methylthioethyl)-malonamide,
2-methyl-N-(5-methyl-6-oxo-6,7-dihydro-5H-dibenzo[b,d]azepin-7-yl)-N'-(3-methoxy-propyl)-malonamide,
2-methyl-N-(5-methyl-6-oxo-6,7-dihydro-5H-dibenzo[b,d]azepin-7-yl)-N'-propyl-malonamide or
2-fluoro-2-methyl-N-(3-methyl-butyl)-N'-(5-methyl-6-oxo-6,7-dihydro-5H-dibenzo[b,d]azepin-7-yl)-malonamide.

Preferred compounds are further those, wherein R$^1$ is a) and R$^2$ is —(CR'R")$_n$—CF$_3$ or —CR'R")$_n$—CHF$_2$, for example
2-methyl-N-(5-methyl-6-oxo-6,7-dihydro-5H-dibenzo[b,d]azepin-7-yl)-N'-(2,2,2-trifluoroethyl)-malonamide,
2-methyl-N-(5-methyl-6-oxo-6,7-dihydro-5H-dibenzo[b,d]azepin-7-yl)-N'-(3,3,3-trifluoro-propyl)-malonamide,
2-fluoro-2-methyl-N-(5-methyl-6-oxo-6,7-dihydro-5H-dibenzo[b,d]azepin-7-yl)-N'-(2,2,2-trifluoro-ethyl)-malonamide,
2-fluoro-2-methyl-N-(5-methyl-6-oxo-6,7-dihydro-5H-dibenzo[b,d]azepin-7-yl)-N'-(2,2,3,3,3-pentafluoro-propyl)-malonamide,
2-fluoro-2-methyl-N-(5-methyl-6-oxo-6,7-dihydro-5H-dibenzo[b,d]azepin-7-yl)-N'-(3,3,4,4-tetrafluoro-butyl)-malonamide,
2-fluoro-2-methyl-N-(5-methyl-6-oxo-6,7-dihydro-5H-dibenzo[b,d]azepin-7-yl)-N'-(4,4,4-trifluoro-butyl)-malonamide,
2-methyl-N-(5-methyl-6-oxo-6,7-dihydro-5H-dibenzo[b,d]azepin-7-yl)-N'-(4,4,4-trifluoro-3-methoxy-butyl)-malonamide,
2-fluoro-2-methyl-N-(5-methyl-6-oxo-6,7-dihydro-5H-dibenzo[b,d]azepin-7-yl)-N'-(3,3,4,4-tetrafluoro-butyl)-malonamide,
N-(5-cyclopropylmethyl-6-oxo-6,7-dihydro-5H-dibenzo[b,d]azepin-7-yl)-2-methyl-N'-(2,2,3,3,3-pentafluoro-propyl)-malonamide,
2-methyl-N-(6-oxo-6,7-dihydro-5H-dibenzo[b,d]azepin-7-yl)-N'-(2,2,3,3,3-pentafluoro-propyl)-malonamide,
N-((S)-6-oxo-6,7-dihydro-5H-dibenzo[b,d]azepin-7-yl)-N'-(2,2,3,3,3-pentafluoro-propyl)-malonamide,
2,2-dimethyl-N-((S)-6-oxo-6,7-dihydro-5H-dibenzo[b,d]azepin-7-yl)-N'-(2,2,3,3,3-pentafluoro-propyl)-malonamide,
(−)-2-methoxy-N-(6-oxo-6,7-dihydro-5H-dibenzo[b,d]azepin-7-yl)-N'-(2,2,3,3,3-pentafluoro-propyl)-malonamide,
(2R)-2-fluoro-2-methyl-N-((S)-6-oxo-6,7-dihydro-5H-dibenzo[b,d]azepin-7-yl)-N'-(2,2,3,3,3-pentafluoro-propyl)-malonamide,
(2S)-2-fluoro-2-methyl-N-[(S)-6-oxo-6,7-dihydro-5H-dibenzo[b,d]azepin-7-yl]-N'-(2,2,3,3,3-pentafluoro-propyl)-malonamide,
N-((S)-5-cyclopropylmethyl-6-oxo-6,7-dihydro-5H-dibenzo[b,d]azepin-7-yl)-N'-(2,2,3,3,3-pentafluoro-propyl)-malonamide,
(R)-N-((S)-5-cyclopropylmethyl-6-oxo-6,7-dihydro-5H-dibenzo[b,d]azepin-7-yl)-2-methyl-N'-(2,2,3,3,3-pentafluoro-propyl)-malonamide,
(S)-N-((S)-5-cyclopropylmethyl-6-oxo-6,7-dihydro-5H-dibenzo[b,d]azepin-7-yl)-2-methyl-N'-(2,2,3,3,3-pentafluoro-propyl)-malonamide,
N-((S)-5-cyclopropylmethyl-6-oxo-6,7-dihydro-5H-dibenzo[b,d]azepin-7-yl)-2,2-dimethyl-N'-(2,2,3,3,3-pentafluoro-propyl)-malonamide,
(R)-N-((S)-5-cyclopropylmethyl-6-oxo-6,7-dihydro-5H-dibenzo[b,d]azepin-7-yl)-2-fluoro-2-methyl-N'-(2,2,3,3,3-pentafluoro-propyl)-malonamide,
N-((S)-5-cyclopropylmethyl-6-oxo-6,7-dihydro-5H-dibenzo[b,d]azepin-7-yl)-2-methoxy-N'-(2,2,3,3,3-pentafluoro-propyl)-malonamide,
N-((S)-5-cyclopropylmethyl-6-oxo-6,7-dihydro-5H-dibenzo[b,d]azepin-7-yl)-N'-(3,3,4,4,4-pentafluoro-butyl)-malonamide, N-((S)-5-cyclopropylmethyl-6-oxo-6,7-dihydro-5H-dibenzo[b,d]azepin-7-yl)-2-methyl-N'-(3,3,4,4,4-pentafluoro-butyl)-malonamide, N-((S)-5-cyclopropylmethyl-6-oxo-6,7-dihydro-5H-dibenzo[b,d]azepin-7-yl)-2,2-dimethyl-N'-(3,3,4,4,4-pentafluoro-butyl)-malonamide, (R)-N-((S)-5-cyclopropylmethyl-6-oxo-6,7-dihydro-5H-dibenzo[b,d]azepin-7-yl)-2-fluoro-2-methyl —N'-(3,3,4,4,4-pentafluoro-butyl)-malonamide, N-(5-isopropyl-6-oxo-6,7-dihydro-5H-dibenzo[b,d]azepin-7-yl)-2-methyl-N'-(2,2,3,3,3-pentafluoro-propyl)-malonamide, N-(5-isopropyl-6-oxo-6,7-dihydro-5H-dibenzo[b,d]azepin-7-yl)-2,2-dimethyl-N'-(2,2,3,3,3-pentafluoro-propyl)-malonamide, N-((S)-5-methyl-6-oxo-6,7-dihydro-5H-dibenzo[b,d]azepin-7-yl)-N'-(2,2,3,3,3-pentafluoro-propyl)-malonamide, 2,2-dimethyl-N-((S)-5-methyl-6-oxo-6,7-dihydro-5H-dibenzo[b,d]azepin-7-yl)-N-(2,2,3,3,3-pentafluoro-propyl)-malonamide, (2R)-2-fluoro-2-methyl-N-[(S)-5-methyl-6-oxo-6,7-dihydro-5H-dibenzo[b,d]azepin-7-yl]-N'-(2,2,3,3,3-pentafluoro-propyl)-malonamide, (2S)-2-fluoro-2-methyl-N-[(S)-5-methyl-6-oxo-6,7-dihydro-5H-dibenzo[b,d]azepin-7-yl]-N'-(2,2,3,3,3-pentafluoro-propyl)-malonamide, 2-methoxy-N-((S)-5-methyl-6-oxo-6,7-dihydro-5H-dibenzo[b,d]azepin-7-yl)-N'-(2,2,3,3,3-pentafluoro-propyl)-malonamide, N-((S)-5-methyl-6-oxo-6,7-dihydro-5H-dibenzo[b,d]azepin-7-yl)-N'-(3,3,4,4,4-pentafluoro-butyl)-malonamide or 2,2-dimethyl-N-[(S)-6-oxo-5-(2,2,2-trifluoro-ethyl)-6,7-dihydro-5H-dibenzo[b,d]azepin-7-yl]-N'-(2,2,3,3,3-pentafluoro-propyl)-malonamide.

A further preferred group of compounds is those, wherein $R^1$ is c) and $R^2$ is —(CR'R")$_n$—CF$_3$ for example the following compounds:

2-methyl-N-(1-methyl-2-oxo-5-phenyl-2,3,4,5-tetrahydro-1H-benzo[b][1,4]diazepin-3-yl)-N'-(2,2,2-trifluoro-ethyl)-malonamide, N-((3S)-5-benzoyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide, N-[(3S)-5-(4-fluoro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide, N-[(3S)-5-(4-chloro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide, N-[(3S)-5-(3,5-difluoro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide, 4-{(3S)-5-methyl-4-oxo-3-[2-(2,2,3,3,3-pentafluoro-propylcarbamoyl)-propionylamino]-2,3,4,5-tetrahydro-benzo[b][1,4]diazepine-1-carbonyl}-benzoic acid methyl ester, N-((3S)-5-acetyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide, N-[5-((3S)-4-fluoro-benzyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide, N-[(3S)-5-(4-chloro-benzoyl)-1-cyclopropylmethyl-2-oxo-2,3,4,5-tetrahydro-1H-benzo[b][1,4]diazepin-3-yl]-2-methyl-N'-(2,2,3,3,3-pentafluoro-propyl)-malonamide, (2RS)-methyl-N-((3S)-1-methyl-2-oxo-5-trifluoromethanesulfonyl-2,3,4,5-tetrahydro-1H-benzo[b][1,4]diazepin-3-yl)-N'-(2,2,3,3,3-pentafluoro-propyl)-malonamide, (2RS)-methyl-N-[(3S)-1-methyl-2-oxo-5-(2,2,2-trifluoro-acetyl)-2,3,4,5-tetrahydro-1H-benzo[b][1,4]diazepin-3-yl]-N'-(2,2,3,3,3-pentafluoro-propyl)-malonamide, N-[(3S)-5-(2-methoxy-acetyl)-1-methyl-2-oxo-2,3,4,5-tetrahydro-1H-benzo[b][1,4]diazepin-3-yl]-(2RS)-methyl-N'-(2,2,3,3,3-pentafluoro-propyl)-malonamide, N-[(S)-5-methanesulfonyl-2-oxo-1-(2,2,2-trifluoro-ethyl)-2,3,4,5-tetrahydro-1H-benzo[b][1,4]diazepin-3-yl]-(2RS)-methyl-N'-(2,2,3,3,3-pentafluoro-propyl)-malonamide, (2RS)-methyl-N-[(S)-2-oxo-1-(2,2,2-trifluoro-ethyl)-5-trifluoromethanesulfonyl-2,3,4,5-tetrahydro-1H-benzo[b][1,4]diazepin-3-yl]-N'-(2,2,3,3,3-pentafluoro-propyl)-malonamide, 5-methyl-4-oxo-(3S)-[(2RS)-(2,2,3,3,3-pentafluoro-propyl-carbamoyl)-propionylamino]-2,3,4,5-tetrahydro-benzo[b][1,4]diazepine-1-carboxylic acid cyclopropylmethyl estermalonamide, N-[(S)-5-cyclopropanecarbonyl-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide, 4-oxo-(3S)-[(2RS)-(2,2,3,3,3-pentafluoro-propylcarbamoyl)-propionylamino]-5-(2,2,2-trifluoro-ethyl)-2,3,4,5-tetrahydro-benzo[b][1,4]diazepine-1-carboxylic acid cyclopropylmethyl ester, N-[(S)-5-acetyl-1-isopropyl-2-oxo-2,3,4,5-tetrahydro-1H-benzo[b][1,4]diazepin-3-yl]-(2RS)-methyl-N'-(2,2,3,3,3-pentafluoro-propyl)-malonamide or N-((S)-5-acetyl-1-benzyl-2-oxo-2,3,4,5-tetrahydro-1H-benzo[b][1,4]diazepin-3-yl)-(2RS)-methyl-N'-(2,2,3,3,3-pentafluoro-propyl)-malonamide.

Preferred compounds are further those, wherein $R^1$ is b), for example 2-methyl-N-(3-methyl-2-oxo-2,3,4,5-tetrahydro-1H-benzo[d]azepin-1-yl)-N'-(2,2,2-trifluoro-ethyl)-malonamide.

Preferred compounds of formula I are further those, wherein $R^1$ is d), for example 2-methyl-N-(11-oxo-10,11-dihydro-dibenzo[b,f]oxepin-10-yl)-N'-(2,2,2-trifluoro-ethyl)-malonamide or 2-methyl-N-(1-oxo-10,11-dihydro-dibenzo[b,f]oxepin-10-yl)-N'-(2,2,3,3,3-pentafluoro-propyl)-malonamide.

In one embodiment, the invention provides compounds of the general formula

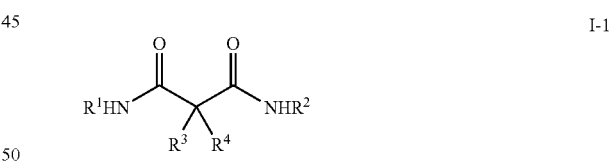

I-1 wherein
$R^1$ is selected from a)

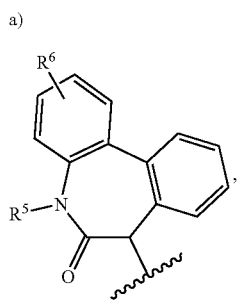

-continued b)
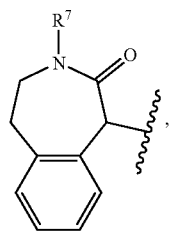

c)
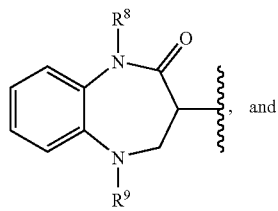, and d)
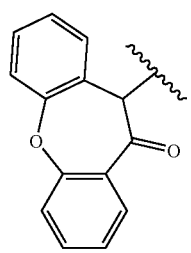

$R^2$ is lower alkyl, lower alkinyl, —$(CH_2)_n$—O-lower alkyl, —$(CH_2)_n$—S-lower alkyl, —$(CH_2)_n$—CN, —$(CR'R'')_n$—$CF_3$, —$(CR'R'')_n$—$CHF_2$, —$(CH_2)_n$—C(O)O-lower alkyl, —$(CH_2)_n$-halogen, or is —$(CH_2)_n$-cycloalkyl optionally substituted by one or more substituents selected from the group consisting of phenyl, halogen and $CF_3$;

$R', R''$ are each independently hydrogen, lower alkyl, lower alkoxy, halogen or hydroxy;

$R^3$, $R^4$ are each independently hydrogen, lower alkyl, phenyl or halogen;

$R^5$ is lower alkyl or —$(CH_2)_2$-cycloalkyl;

$R^6$ is hydrogen or halogen;

$R^7$ is hydrogen or lower alkyl;

$R^8$ is hydrogen, lower alkyl, lower alkinyl or —$(CH_2)_2$-cycloalkyl;

$R^9$ is hydrogen, lower alkyl, —C(O)-lower alkyl, —C(O)-lower cycloalkyl, —$(CH_2)_n$-cycloalkyl, phenyl, —C(O)-phenyl optionally substituted by one or more substituents selected from the group consisting of halogen and —C(O)O-lower alkyl, or is $(CH_2)_2$-phenyl optionally substituted by halogen;

n is 0, 1, 2, 3 or 4;

or a pharmaceutically acceptable acid addition salt, optically pure enantiomer, racemate or diastereomeric mixture thereof.

The present compounds of formula I and their pharmaceutically acceptable acid addition salts can be prepared by methods known in the art, for example, by processes described below, which processes comprise a) reacting a compound of formula

II with a compound of formula $NH_2R^2$   III to produce a compound of formula

I wherein $R^1$–$R^4$ have the meaning as described above, and if desired, converting the compounds obtained into pharmaceutically acceptable acid addition salts.

The detailed description can be found below and in Examples 1–121. The starting materials of formula IV are known compounds or can be prepared by methods well-known in the art. The amines of formulas VI and III are commercially available products or can be prepared by methods described in the literature.

Scheme 1

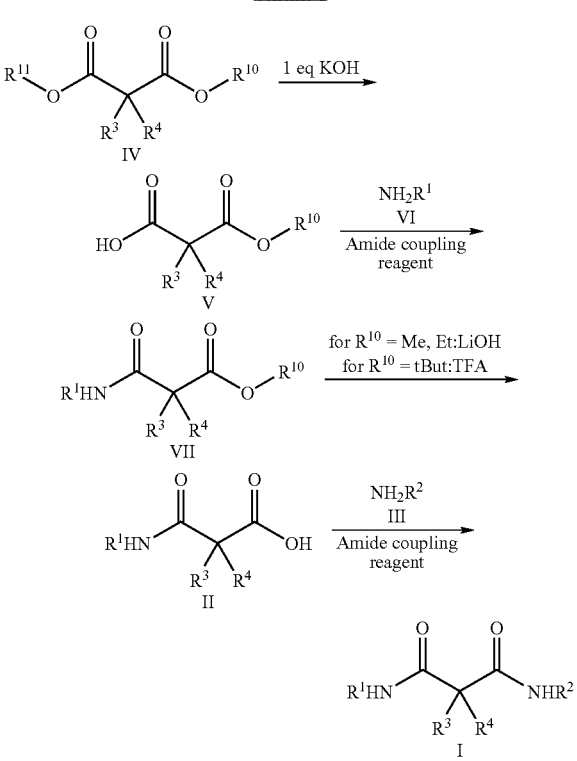

In this scheme $R^1$ and $R^2$ are as described below and $R^{10}$ and $R^{11}$ are independently lower alkyl.

In accordance with scheme 1 a compound of formula I can be prepared as follows: To a cooled solution of a compound of formula V, for example 2-methyl-malonic acid mono-tert-butyl ester, and an amine of formula VI, for example 7-amino-5-methyl-5H,7H-dibenzo[b,d]azepin-6-one, in THF is added hydroxybenzotriazole, diisopropylethylamine and N-(3-dimethylaminopropyl)-N'-ethylcarbodiimide hydrochloride, and the mixture is stirred overnight at r.t. The solvent is evaporated, and the residue is washed, dried and purified in usual manner.

Then TFA (trifluoroacetic acid) is added to the obtained solution of formula VII, for example 2-methyl-N-(5-methyl-6-oxo-6,7-dihydro-5H-dibenzo[b,d]azepin-7-yl)-malonamic acid tert-butyl ester in dichloromethane, and the mixture is stirred at r.t. overnight. The mixture is then taken up in more dichloromethane, washed and dried. After evaporation of the solvent, a compound of formula II, for example 2-methyl-N-(5-methyl-6-oxo-6,7-dihydro-5H-dibenzo[b,d]azepin-7-yl)-malonamic acid, is obtained. This obtained compound and a compound of formula III, for example cyclopropyl-methylamine, are placed in a disposable polypropylene tube and dissolved in DMF. TPTU (2-(2-pyridon-1-yl)-1,1,3,3-tetramethyl uranium tetrafluoroborate) is added, and the mixture is shaken overnight at r.t. The obtained compound of formula I is isolated and purified in a conventional manner.

Compounds of formula I can be converted to a corresponding acid addition salt. The conversion is accomplished by treatment with at least a stoichiometric amount of an appropriate acid, such as hydrochloric acid, hydrobromic acid, sulfueric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, it has been found that the compounds of the present invention may inhibit the γ-secretase.

The compounds were investigated in accordance with the test given hereinafter.

Description of γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro asays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. The latter consist of the C-terminal 100 amino acids of human APP fused to a 6× Histidin tail for purification which is expressed in $E.\ coli$ in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138–6143 (2000). Hek293 cells are mechanically disrupted, and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481–1486 (1998).

The preferred compounds show a $IC_{50}<0.1\ \mu M$. In the list below are described some data to γ-secretase inhibition:

TABLE 1

| Example No. | $IC_{50}$ in vitro |
|---|---|
| 1 | 0.09 |
| 4 | 0.02 |
| 5 | 0.071 |
| 6 | 0.031 |
| 8 | 0.015 |
| 13 | 0.02 |
| 14 | 0.037 |
| 21 | 0.03 |
| 23 | 0.018 |
| 24 | 0.005 |
| 26 | 0.056 |
| 28 | 0.073 |
| 29 | 0.06 |
| 30 | 0.079 |
| 35 | 0.012 |
| 36 | 0.006 |
| 37 | 0.013 |
| 38 | 0.02 |
| 39 | 0.09 |
| 40 | 0.07 |
| 43 | 0.03 |
| 44 | 0.03 |
| 49 | 0.033 |
| 50 | 0.043 |
| 51 | 0.019 |
| 65 | 0.006 |
| 66 | 0.017 |
| 67 | 0.004 |
| 68 | 0.008 |
| 69 | 0.002 |
| 70 | 0.006 |
| 71 | 0.011 |
| 72 | 0.005 |
| 73 | 0.008 |
| 74 | 0.001 |
| 75 | 0.002 |
| 76 | 0.004 |
| 77 | 0.05 |
| 78 | 0.002 |
| 79 | 0.006 |
| 80 | 0.003 |
| 81 | 0.025 |

TABLE 1-continued

| Example No. | $IC_{50}$ in vitro |
|---|---|
| 82 | 0.009 |
| 83 | 0.020 |
| 84 | 0.007 |
| 85 | 0.003 |
| 86 | 0.047 |
| 87 | 0.017 |
| 88 | 0.05 |
| 89 | 0.020 |
| 95 | 0.071 |
| 98 | 0.080 |
| 99 | 0.059 |
| 101 | 0.040 |
| 106 | 0.090 |
| 108 | 0.046 |
| 109 | 0.048 |
| 113 | 0.030 |
| 115 | 0.067 |
| 121 | 0.038 |

In another aspect, the invention provides compositions containing a compound of formula I or a pharmaceutically acceptable acid addition salt thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

In another aspect, the present invention provides a process for the production of the compositions of the invention. This process comprises bringing one or more compounds of formula I and/or pharmaceutically acceptable acid addition salts and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

It has been found that the compounds of general formula I as well as their pharmaceutically acceptable acid addition salts are γ-secretase inhibitors. Thus, in yet another aspect, the invention provides methods of inhibiting γ-secretase and treating diseases associated for which reduction of γ-secretase is beneficial. Further, the present invention provides a method for the treatment or prevention of Alzheimer's disease. For example, the present invention provides a method for the treatment or prevention of Alzheimer's disease which comprises administering to an individual having or at risk for developing Alzheimer's disease a therapeutically effective amount of a compound of formula I or a pharmaceutically acceptable acid addition salt thereof.

The dosage at which the compound of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable acid addition salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

N-Cyclopropylmethyl-2-methyl-N'-(5-methyl-6-oxo-6,7-dihydro-5H-dibenzo[b,d]azepin-7-yl)-malonamide a) 2-Methyl-N-(5-methyl-6-oxo-6a7-dihydro-5H-dibenzo[b,d]azepin-7-yl)-malonanic acid tert-butyl ester To a cooled solution (0° C.) of 2-methyl-malonic acid mono-tert-butyl ester (1.01 g, 5.79 mmol) and 7-amino-5-methyl-5H,7H-dibenzo[b,d]azepin-6-one (1.15 g, 4.83 mmol) in THF (8 ml) was added hydroxybenzotriazole (652 mg, 4.83 mmol), diisopropylethylamine (624 mg, 4.83 mmol) and N-(3-dimethylaminopropyl)-N'-ethylcarbodiimide hydrochloride (925 mg, 4.83 mmol), and the mixture was stirred overnight at r.t. The solvent was evaporated, the residue was taken up in ethyl acetate, washed with water, and dried ($Na_2SO_4$). After evaporation of the solvent, the title compound, MS: m/e=395.3 ($M+H^+$), (920 mg, 48%) was obtained by chromatographic purification of the residue (silica gel, MeOH, $CH_2Cl_2$).

b) 2-Methyl-N-(5-methyl-6-oxo-6,7-dihydro-5H-dibenzo[b,d]azepin-7-yl)-malonamic acid TFA (3 ml) was added to a solution of 2-methyl-N-(5-methyl-6-oxo-6,7-dihydro-5H-dibenzo[b,d]azepin-7-yl)-malonamic acid tert-butyl ester (920 mg, 2.33 mmol) in dichloromethane (3 ml) and the mixture was stirred at r.t. overnight. The mixture was then taken up in more dichloromethane, washed with water, and dried ($Na_2SO_4$). After evaporation of the solvent, the title compound, MS: m/e=339.3 ($M+H^+$), (580 mg, 73%) was obtained by chromatographic purification of the residue (silica gel, MeOH, $CH_2Cl_2$).

c) N-Cyclopropylmethyl-2-methyl-N'-(5-methyl-6-oxo-6,7-dihydro-5H-dibenzo[b,d]azepin 7-yl)-malonamide 2-Methyl-N-(5-methyl-6-oxo-6,7-dihydro-5H-dibenzo[b,d]azepin-7-yl)-malonamic acid (20 mg, 0.059 mmol) and cyclopropylmethylamine (5 mg, 0.059 mmol) were placed in a disposable polypropylene tube and dissolved in DMF (2 ml). TPTU (2-(2-pyridon-1-yl)-1,1,3,3-tetramethyl uronium tetrafluoroborate, 19 mg, 0.065 mmol) was added, and the mixture was shaken overnight at r.t. The title compound, MS: m/e=392.2 ($M+H^+$), was isolated from the reaction mixture by automated, preparative HPLC (YMC CombiPrep C18 column 50×20 mm, solvent gradient 5–95% $CH_3CN$ in 0.1% TFA(aq) over 6.0 min, λ=230 nm, flow rate 40 ml/min).

EXAMPLE 2

2-Methyl-N-(5-methyl-6-oxo-6,7-dihydro-5H-dibenzo[b,d]azepin-7-yl)-N'-ethyl-malonamide The title compound, MS: m/e=366.2 ($M+H^+$), was prepared in analogy to example 1 from ethylamine.

EXAMPLE 3

2-Methyl-N-(5-methyl-6-oxo-6,7-dihydro-5H-dibenzo[b,d]azepin-7-yl)-N'-propargyl-malonamide The title compound, MS: m/e=376.3 ($M+H^+$), was prepared in analogy to example 1 from propargylamine.

EXAMPLE 4

2-Methyl-N-(5-methyl-6-oxo-6,7-dihydro-5H-dibenzo[b,d]azepin-7-yl)-N'-(2-methoxyethyl)-malonamide The title compound, MS: m/e=396.3 ($M+H^+$), was prepared in analogy to example 1 from 2-methoxyethylamine.

EXAMPLE 5

2-Methyl-N-(5-methyl-6-oxo-6,7-dihydro-5H-dibenzo[b,d]azepin-7-yl)-N'-propyl-malonamide The title compound, MS: m/e=380.3 ($M+H^+$), was prepared in analogy to example 1 from propylamine.

EXAMPLE 6

2-Methyl-N-(5-methyl-6-oxo-6,7-dihydro-5H-dibenzo[b,d]azepin-7-yl)-N'-(2-methylthioethyl)-malonamide The title compound, MS: m/e=412.3 ($M+H^+$), was prepared in analogy to example 1 from 2-Methylthioetylamine.

EXAMPLE 7

2-Methyl-N-(5-methyl-6-oxo-6,7-dihydro-5H-dibenzo[b,d]azepin-7-yl)-N'-cyclobutyl-malonamide The title compound, MS: m/e=392.3 ($M+H^+$), was prepared in analogy to example 1 from cyclobutylamine.

EXAMPLE 8

2-Methyl-N-(5-methyl-6-oxo-6,7-dihydro-5H-dibenzo[b,d]azepin-7-yl)-N'-(3-methoxy-propyl)-malonamide The title compound, MS: m/e=410.3 ($M+H^+$), was prepared in analogy to example 1 from 3-methoxypropylamine.

EXAMPLE 9

2-Methyl-N-(5-methyl-6-oxo-6,7-dihydro-5H-dibenzo[b,d]azepin-7-yl)-N'-cyanomethyl-malonamide The title compound, MS: m/e=377.3 ($M+H^+$), was prepared in analogy to example 1 from aminoacetonitrile.

EXAMPLE 10

2-Methyl-N-(5-methyl-6-oxo-6,7-dihydro-5H-dibenzo[b,d]azepin-7-yl)-N'-cyclopropyl-malonamide The title compound, MS: m/e=378.3 ($M+H^+$), was prepared in analogy to example 1 from cyclopropylamine.

EXAMPLE 11

2-Methyl-N-(5-methyl-6-oxo-6,7-dihydro-5H-dibenzo[b,d]azepin-7-yl)-N'-(2-cyanoethyl)-malonamide The title compound, MS: m/e=391.2 ($M+H^+$), was prepared in analogy to example 1 from 3-aminopropionitrile.

EXAMPLE 12

2-Methyl-N-(5-methyl-6-oxo-6,7-dihydro-5H-dibenzo[b,d]azepin-7-yl)-N'-(2-ethoxyethyl)malonamide The title compound, MS: m/e=410.3 (M+H$^+$), was prepared in analogy to example 1 from 2-ethoxyethylamine.

EXAMPLE 13

2-Methyl-N-(5-methyl-6-oxo-6,7-dihydro-5H-dibenzo[b,d]azepin-7-yl)-N'-(2,2,2-trifluoroethyl)-malonamide The title compound, MS: m/e=420.2 (M+H$^+$), was prepared in analogy to example 1 from 2,2,2-trifluoroethylamine.

EXAMPLE 14

2-Methyl-N-(5-methyl-6-oxo-6,7-dihydro-5H-dibenzo[b,d]azepin-7-yl)-N'-(3,3,3-trifluoro-propyl)-malonamide The title compound, MS: m/e=434.3 (M+H$^+$), was prepared in analogy to example 1 from 3,3,3-trifluoropropylamine.

EXAMPLE 15

2-Methyl-N-(5-methyl-6-oxo-6,7-dihydro-5H-dibenzo[b,d]azepin-7-yl)-N'-(2,2,3,3,3-pentafluoro-propyl)-malonamide The title compound, MS: m/e=470.1 (M+H$^+$), was prepared in analogy to example 1 from 2,2,3,3,3-pentafluoropropylamine.

EXAMPLE 16

[2-(5-Methyl-6-oxo-6,7-dihydro-5H-dibenzo[b,d]azepin-7-ylcarbamoyl)-propionylamino]-acetic acid tert-butyl ester The title compound, MS: m/e=452.3 (M+H$^+$), was prepared in analogy to example 1 from tert-butyl glycinate.

EXAMPLE 17

2-Methyl-N-(5-methyl-6-oxo-6,7-dihydro-5H-dibenzo[b,d]azepin-7-yl)-N'-(3,3,3-trifluoro-2-hydroxy-propyl)-malonamide The title compound, MS: m/e=450.2 (M+H$^+$), was prepared in analogy to example 1 from 3-amino-1,1,1-trifluoro-2-propanol.

EXAMPLE 18

N-(2,2-Difluoro-3-phenyl-cyclopropylmethyl)-2-methyl-N'-(5-methyl-6-oxo-6,7-dihydro-5H-dibenzo[b,d]azepin-7-yl)-malonamide The title compound, MS: m/e=504.3 (M+H$^+$), was prepared in analogy to example 1 from C-(2,2-difluoro-3-phenyl-cyclopropyl)-methylamine.

EXAMPLE 19

N-(2,2-Difluoro-cyclopropylmethyl)-2-methyl-N'-(5-methyl-6-oxo-6,7-dihydro-5H-dibenzo[b,d]azepin-7-yl)-malonamide The title compound, MS: m/e=428.2 (M+H$^+$), was prepared in analogy to example 1 from C-(2,2-difluoro-cyclopropyl)-methylamine.

EXAMPLE 20

2-Methyl-N-(3-methyl-2-oxo-2,3,4,5-tetrahydro-1H-benzo[d]azepin-1-yl)-N'-(2,2,2-trifluoro-ethyl)-malonamide a) 2-methyl-malonic acid monoethyl ester To a solution of 6.44 g (115 mmol) potassium hydroxide in 200 ml of ethanol 20.0 g diethyl methyl-malonate (115 mmol) was added and the mixture was refluxed for 4 hours. After cooling the reaction mixture was concentrated on a rotary evaporator, 50 ml of water was added and the mixture was extracted with ether (two times 50 ml). The aqueous solution was acidified with 4M hydrochloric acid and extracted with ethyl acetate (three times 50 ml). The combined organic layers were dried (MgSO$_4$), concentrated under reduced pressure and used without further purification.

MS m/e (%): 101.1 (M-EtO, 100), 147.1 (M+H$^+$, 8).

b) 2-Methyl-N-(2,2,2-trifluoro-ethyl)-malonamic acid ethyl ester

To a solution of 1.56 g (10.6 mmol) methyl-malonic acid monoethyl ester in 20 ml of tetrahydrofuran 1.06 g (10.6 mmol) of 2,2,2-trifluoroethylamine, 2.05 g (10.6 mmol) of N-(3-dimethylaminopropyl)-N'-ethylcarbodiimide hydrochloride, 1.44 g (10.6 mmol) of 1-hydroxybenzotrizole hydrate and 2.75 g (21.2 mmol) of N,N-diisopropyl-ethylamine were added. The mixture was stirred at room temperature for 18 h. The mixture was poured onto 0.5 N HCl (50 ml) and afterwards extracted with dichloromethane (three times 50 ml). The combined organic layers were extracted with 0.5 N aqueous NaHCO$_3$ solution, dried (MgSO$_4$) and evaporated on the rotary evaporator. The residue was purified by column filtration (hexane/ethyl acetate=2:1) to yield 1.48 g (61%) of the title compound as white crystalline solid.

MS m/e (%): 226,1 (M–H$^+$, 100).

c) 2-Methyl-N-(2,2,2-trifluoro-ethyl)-malonamic acid

To a solution of 1.48 g (6.52 mmol) 2-Methyl-N-(2,2,2-trifluoro-ethyl)-malonamic acid ethyl ester in 40 ml of tetrahydrofurane, 20 ml of water and 1.09 g (26 mmol) of lithium hydroxide were added and the mixture was stirred overnight at room temperature. After concentration in vacuo water (50 ml) was added and the mixture was extracted with dichloromethane (three times 30 ml). The aqueous phase was acidified with 8 N hydrochloric acid and extracted with dichloromethane (four times 30 ml). The combined organic layers from the second extraction were dried (MgSO$_4$) and evaporated in vacuo to give 1.09 g (84%) of the title compound as a white solid.

MS m/e (%): 197,9 (M–H$^+$, 100).

d) 2-Methyl-N-(3-methyl-2-oxo-2,3,4,5-tetrahydro-1H-benzo[d]azeyin-1-yl)-N'-(2,2,2-trifluoro-ethyl)-malonamide To a solution of 0.066 g (0.3 mmol) 2-methyl-N-(2,2,2-trifluoro-ethyl)-malonamic acid in 2 ml of tetrahydrofuran 0.057 g (0.3 mmol) of (RS)-1-amino-3-methyl-1,3,4,5-tetrahydro-benzo[d]azepin-2-one, 0.058 g (0.3 mmol) of N-(3-dimethylaminopropyl)-N'-ethylcarbodiimide hydrochloride, 0.040 g (0.3 mmol) of 1-hydroxybenzotrizole hydrate and 0.116 g (0.9 mmol) of N,N-diisopropyl-ethylamine were added. The mixture was stirred at room temperature for 18 h. Then 0.5 N HCl (5 ml) was added and the mixture was extracted with dichloromethane (three times 5 ml). The combined organic layers were extracted with 0.5 N aqueous NaHCO$_3$ solution, dried (MgSO$_4$) and evaporated on the rotary evaporator. The residue was purified by flash chromatography (hexane/ethyl acetate=3:1) to yield 0.10 g (89%) of the diastereomeric mixture of title compound as white solid.

MS m/e (%): 372,1 (M+H$^+$, 100).

EXAMPLE 21

2-Methyl-N-(1-methyl-2-oxo-5-phenyl-2,3,4,5-tetrahydro-1H-benzo[b][1,4]diazepin-3-yl)-N'-(2,2,2-trifluoro-ethyl)-malonamide The title compound was obtained in comparable yields according to the procedures described for example 20 using (RS)-3-amino-1-methyl-5-phenyl-1,3,4,5-tetrahydro-benzo[b][1,4]diazepin-2-one instead of (RS)-1-amino-3-methyl-1,3,4,5-tetrahydro-benzo[d]azepin-2-one diethyl methyl-malonate in step d).

MS m/e (%): 449.1 (M+H$^+$, 100).

EXAMPLE 22

N-(5-Methyl-6-oxo-6,7-dihydro-5H-dibenzo[b,d]azepin-7-yl)-2-phenyl-N'-(2,2,2-trifluoro-ethyl)-malonamide The title compound was obtained in comparable yields according to the procedures described for example 20 using diethyl phenylmalonate instead of diethyl methyl-malonate in step a) and (RS)-7-amino-5-methyl-5H,7H-dibenzo[b,d]azepin-6-one instead of (RS)-1-amino-3-methyl-1,3,4,5-tetrahydro-benzo[d]azepin-2-one in step d).

MS m/e (%): 482.1 (M+H$^+$, 100).

EXAMPLE 23

2-Fluoro-2-methyl-N-(5-methyl-6-oxo-6,7-dihydro-5H-dibenzo[b,d]azepin-7-yl)-N'-(2,2,2-trifluoro-ethyl)-malonamide The title compound was obtained in comparable yields according to the procedures described for example 20 using diethyl 2-fluoro-2-methylmalonate instead of diethyl methyl-malonate in step a) and (RS)-7-amino-5-methyl-5H,7H-dibenzo[b,d]azepin-6-one instead of (RS)-1-amino-3-methyl-1,3,4,5-tetrahydro-benzo[d]azepin-2-one in step d).

MS m/e (%): 438.3 (M+H$^+$, 100).

EXAMPLE 24

2-Fluoro-2-methyl-N-(5-methyl-6-oxo-6,7-dihydro-5H-dibenzo[b,d]azepin-7-yl)-N'-(2,2,3,3,3-pentafluoro-propyl)-malonamide The title compound was obtained in comparable yields according to the procedures described for example 20 using diethyl 2-fluoro-2-methylmalonate instead of diethyl methyl-malonate in step a), pentafluoropropylamine instead of 2,2,2-trifluoroethylamine in step b) and (RS)-7-amino-5-methyl-5H,7H-dibenzo[b,d]azepin-6-one instead of (RS)-1-amino-3-methyl-1,3,4,5-tetrahydro-benzo[d]azepin-2-one in step d).

MS m/e (%): 488.2 (M+H$^+$, 100).

EXAMPLE 25

2-Methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide a) (S)-3-Amino-1-methyl-1,3,4,5-tetrahydro-benzo[b][1,4]diazepin-2-one To a solution of 5.0 g (18 mmol) (S)-(2-oxo-2,3,4,5-tetrahydro-1H-benzo[b][1,4]diazepin-3-yl)-carbamic acid tert-butyl ester in 80 ml of tetrahydrofuran at −75° C. 18 ml (18 mmol) of lithium bis(trimethylsilyl)amide solution (1M in tetrahydrofurane) was added. After stirring for 30 min at −75° C. the mixture was allowed to reach room temperature and 3.07 g (21.6 mmol) of methyl iodide was added. The mixture was stirred for 2.5 hours at room temperature and concentrated in vacuo. The residue was distributed between 1M NaHSO$_4$ solution and ethyl acetate. The combined organic layers were reextracted with water and dried (MgSO$_4$). After evaporation of the solvent 20 ml of dichlorometane and 20 ml of trifluoracetic acid was added and the mixture was stirred for 2.5 h at room temperature. For workup the mixture was concentrated in vacuo, then ethylacetate was added and the mixture was extracted two times with water. The aqueouos phase was basified with sodium hydroxide and extracted three times with ethyl acetate. The combined organic layers were dried (MgSO$_4$) and evaporated. The residue was purified by column chromatography (dichloromethane/methanol=9:1) to yield 2.1 g (65%) of (S)-3-amino-1-methyl-1,3,4,5-tetrahydro-benzo[b][1,4]diazepin-2-one.

MS m/e (%): 192.2 (M−H$^+$, 100).

b) 2-Methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide The title compound was obtained in comparable yields according to the procedures described for example 20 using pentafluoropropylamine instead of 2,2,2-trifluoroethylamine in step b) and (S)-3-amino-1-methyl-1,3,4,5-tetrahydro-benzo[b][1,4]diazepin-2-one instead of (RS)-1-amino-3-methyl-1,3,4,5-tetrahydro-benzo[d]azepin-2-one in step d).

MS m/e (%): 421.2 (M−H$^+$, 100).

EXAMPLE 26

N-((3S)-5-Benzoyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide To a solution of 0.2 g (0.47 mmol) of 2-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide in 3 ml of dichloromethane 0.096 g (0.95 mmol) of triethylamine and 0.08 mg (0.57 mmol) of benzoylchloride were added. The mixture was stirred for 20 min at room temperature. Hydrochloric acid (10 ml of a 1 N solution) was added and the mixture was extracted two times with dichloromethane. The combined organic layers were extracted with 1N sodiumbicarbonate solution, dried (MgSO$_4$) and concentrated in vacuo. The remaining oil was purified by column chromatography to yield 0.15 g (60%) of a white foam.

MS m/e (%): 527.3 (M+H$^+$, 100).

EXAMPLE 27

N-((3S)-5-Benzoyl-1-methyl-2-oxo-2,3,4,5-tetrahydro-1H-benzo[b][1,4]diazepin-3-yl)-2,2-dimethyl-N'-(2,2,2-trifluoro-ethyl)-malonamide The title compound was obtained in comparable yields according to the procedures described for example 25 using diethyl 2,2-dimethylmalonate instead of diethyl methyl-malonate and 2,2,2-trifluoroethylamine instead of pentafluoropropylamine in step b) followed by the reaction with benzoylchloride as described in example 26.

MS m/e (%): 491.3 (M+H$^+$, 100).

EXAMPLE 28

N-[(3)S5-(4-Fluoro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide The title compound was obtained in comparable yields according to the procedures described for example 26 using 4-fluorobenzoylchloride instead of benzoylchloride.

MS m/e (%): 545.3 (M+H$^+$, 100).

EXAMPLE 29

N-[(3S)-5-(4-Chloro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide The title compound was obtained in comparable yields according to the procedures described for example 26 using 4-chlorobenzoylchloride instead of benzoylchloride.

MS m/e (%): 561.4 (M+H$^+$, 100).

EXAMPLE 30

N-[(3S)-5-(3,5-Difluoro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide The title compound was obtained in comparable yields according to the procedures described for example 26 using 3,5-difluorobenzoylchloride instead of benzoylchloride.

MS m/e (%): 563.4 (M+H$^+$, 100).

EXAMPLE 31

2-Fluoro-2-methyl-N-(5-methyl-6-oxo-6,7-dihydro-5H-dibenzo[b,d]azepin-7-yl)-N'-(3,3,3-trifluoro-2-hydroxy-1,1-dimethyl-propyl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and rac-3-amino-1,1,1-trifluoro-3-methyl-2-butanol instead of (RS)-1-amino-3-methyl-1,3,4,5-tetrahydro-benzo[d]azepin-2-one in step d).

MS m/e (%): 496.2 (M+H$^+$, 100).

EXAMPLE 32

2-Fluoro-N-(2-fluoro-ethyl)-2-methyl-N'-(5-methyl-6-oxo-6,7-dihydro-5H-dibenzo[b,d]azepin-7-yl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and 2-fluoroethylamine instead of (RS)-1-amino-3-methyl-1,3,4,5-tetrahydro-benzo[d]azepin-2-one in step d).

MS m/e (%): 402,2 (M+H$^+$, 100).

EXAMPLE 33

N-(2,2-Difluoro-ethyl)-2-fluoro-2-methyl-N'-(5-methyl-6-oxo-6,7-dihydro-5H-dibenzo[b,d]azepin-7-yl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and 2,2-difluoroethylamine instead of (RS)-1-amino-3-methyl-1,3,4,5-tetrahydro-benzo[d]azepin-2-one in step d).

MS m/e (%): 420.1 (M+H$^+$, 100).

EXAMPLE 34

2-Fluoro-N-(2-cis-fluoro-cyclopropyl)-2-methyl-N'-(5-methyl-6-oxo-6,7-dihydro-5H-dibenzo[b,d]azepin-7-yl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and cis-2-fluorocyclopropylamine instead of (RS)-1-amino-3-methyl-1,3,4,5-tetrahydro-benzo[d]azepin-2-one in step d).

MS m/e (%): 414.2 (M+H$^+$, 100).

EXAMPLE 35

2-Fluoro-2-methyl-N-(5-methyl-6-oxo-6,7-dihydro-5H-dibenzo[b,d]azepin-7-yl)-N'-(3,3,4,4-tetrafluoro-butyl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and 3,3,4,4-tetrafluorobutylamine (available from the corresponding bromide via the Phthalimide method according to Jacobs et al: J.Med.Chem. 1994, 37, 1282) instead of (RS)-1-amino-3-methyl-1,3,4,5-tetrahydro-benzo[d]azepin-2-one in step d).

MS m/e (%): 484.2 (M+H$^+$, 100).

EXAMPLE 36

2-Fluoro-2-methyl-N-(5-methyl-6-oxo-6,7-dihydro-5H-dibenzo[b,d]azepin-7-yl)-N'-(4,4,4-trifluoro-butyl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and 4,4,4-trifluorobbutylamine instead of (RS)-1-amino-3-methyl-1,3,4,5-tetrahydro-benzo[d]azepin-2-one in step d).

MS m/e (%): 466.2 (M+H$^+$, 100).

EXAMPLE 37

2-Fluoro-2-methyl-N-(3-methyl-butyl)-N'-(5-methyl-6-oxo-6,7-dihydro-5H-dibenzo[b,d]azepin-7-yl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and 3-methyl-butylamine instead of (RS)-1-amino-3-methyl-1,3,4,5-tetrahydro-benzo[d]azepin-2-one in step d).

MS m/e (%): 426.2 (M+H$^+$, 100).

EXAMPLE 38

2-Fluoro-2-methyl-N-(5-methyl-6-oxo-6,7-dihydro-5H-dibenzo[b,d]azepin-7-yl)-N'-(1-trifluoromethyl-cyclopropylmethyl)-malonamide The title compound was obtained in comparable yields according to the procedures described for example 20 using diethyl 2-fluoro-2-methylmalonate instead of diethyl methyl-malonate in step a), (RS)-7-amino-5-methyl-5H,7H-dibenzo[b,d]azepin-6-one instead of 2,2,2-trifluoroethylamine in step b) and 1-trifluormethyl-cyclopropylmethylamine (available from the corresponding alcohol via the Phthalimide method according to Jacobs et al: J.Med.Chem. 1994, 37, 1282) instead of (RS)-1-amino-3-methyl-1,3,4,5-tetrahydro-benzo[d]azepin-2-one in step d).

MS m/e (%): 478.1 (M+H$^+$, 100).

EXAMPLE 39

4-{(3S)-5-Methyl-4-oxo-3-[2-(2,2,3,3,3-pentafluoro-propylcarbamoyl)-propionylamino]-2,3,4,5-tetrahydro-benzo[b][1,4]diazepine-1-carbonyl}-benzoic Acid Methyl Ester The title compound was obtained in comparable yields according to the procedures described for example 26 using 4-(methoxycarbonyl)-benzoylchloride instead of benzoylchloride.

MS m/e (%): 583.3 (M+H$^+$, 100).

EXAMPLE 40

N-((3S5-Acetyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide The title compound was obtained in comparable yields according to the procedures described for example 26 using acetylchloride instead of benzoylchloride.

MS m/e (%): 465.2 (M+H$^+$, 100).

EXAMPLE 41

2-Methyl-N-(11-oxo-10,11-dihydro-dibenzo[b,f]oxepin-10-yl)-N'-(2,2,2-trifluoro-ethyl)-malonamide a) (RS)-11-Amino-11H-dibenzo[b,f]oxepin-10-one hydrochloride To a solution of 1.85 g (8.77 mmol) 11H-dibenzo[b,f]oxepin-10-one in 4 ml of toluene at −20° C. 2.5 g (21.9 mmol) of potassium tert.butoxide was added. The solution was saturated with N2. After stirring for 15 min 1.2g (10.5 mmol) of isoamyl nitrite was added. After stirring overnight at room temperature the solution was cooled at 0° C. for 15 min water (80 ml), acetic acid (4 ml) and ethyl acetate (80 ml) were added. The aqueouos phase was extracted with ethyl acetate. The combined organic layers were reextracted with water and dried (MgSO$_4$). After evaporation of the ethyl acetate the resulting slurry of the oxim in toluene was cooled to 0° C. during an hour and filtered. The solid material was dissolved in tetrahydrofurane (20 ml), 8 ml 1M hydrochloric acid in tetrahydrofurane and 20 mg of platinum oxide were added. The reaction mixture was flushed with N2 and subjected to a hydrogen atmosphere of 50 psi at room temperature. After stirring overnight with hydrogen atmosphere the formed precipitate was collected by filtration, washed with tetrahydrofurane and recrystallised from a methanol tetrahydrofurane mixture to yield 0.9 g of white crystals (Fp.215–217° C.)

b) 2-Methyl-N-(11-oxo-10,11-dihydro-dibenzo[b,f]oxepin-10-yl)-N'-(2,2,2-trifluoro-ethyl)-malonamide The title compound was obtained in comparable yields according to the procedures described for example 20 using (RS)-11-amino-11H-dibenzo[b,f]oxepin-10-one instead of (RS)-1-amino-3-methyl-1,3,4,5-tetrahydro-benzo[d]azepin-2-one in step d).

MS m/e (%): 407.3 (M+H$^+$, 100).

EXAMPLE 42

2-Methyl-N-(11-oxo-10,11-dihydro-dibenzo[b,f]oxepin-10-yl)-N'-(2,2,3,3,3-pentafluoro-propyl)-malonamide The title compound was obtained in comparable yields according to the procedures described for example 20 using 2,2,3,3,3-pentafluoropropylamine instead of 2,2,2-trifluoroethylamine in step b) and (RS)-11-amino-11H-dibenzo[b,f]oxepin-10-one instead of (RS)-1-amino-3-methyl-1,3,4,5-tetrahydro-benzo [d] azepin-2-one in step d).

MS m/e (%): 457.4 (M+H$^+$, 100).

EXAMPLE 43

2-Methyl-N-(5-methyl-6-oxo-6,7-dihydro-5H-dibenzo[b,d]azepin-7-yl)-N'-(4,4,4-trifluoro-3-methoxy-butyl)-malonamide The title compound was obtained in comparable yields according to the procedures described for example 20 using (RS)-7-amino-5-methyl-5H,7H-dibenzo[b,d]azepin-6-one instead of 2,2,2-trifluoroethylamine in step b) and 4,4,4-trifluoro-3-methoxy-butylamine (available from 4,4,4-trifluoro-3-methoxybutaneamide via lithium aluminiumhydride reduction according to Jacobs et al: J.Med.Chem.1994, 37, 1282) instead of (RS)-1-amino-3-methyl-1,3,4,5-tetrahydro-benzo[d]azepin-2-one in step d).

MS m/e (%): 476.3 (M−H$^+$, 100).

EXAMPLE 44

2-Fluoro-N-(5-methyl-6-oxo-6,7-dihydro-5H-dibenzo[b,d]azepin-7-yl)-N'-(3,3,4,4-tetrafluoro-butyl)-malonamide The title compound was obtained in comparable yields according to the procedures described for example 20 using (RS)-7-amino-5-methyl-5H,7H-dibenzo[b,d]azepin-6-one instead of 2,2,2-trifluoroethylamine in step b) and 3,3,4,4-tetrafluorobutylamine (available from the corresponding bromide via the Phthalimide method according to Jacobs et al: J.Med.Chem.1994, 37, 1282) instead of (RS)-1-amino-3-methyl-1,3,4,5-tetrahydro-benzo[d]azepin-2-one in step d).

MS m/e (%): 464.2 (M−H$^+$, 100).

EXAMPLE 45

N-(3-Isopropoxy-propyl)-2-methyl-N'-(5-methyl-6-oxo-6,7-dihydro-5H-dibenzo[b,d]azepin-7-yl)-malonamide The title compound was obtained in comparable yields according to the procedures described for example 20 using (RS)-7-amino-5-methyl-5H,7H-dibenzo[b,d]azepin-6-one instead of 2,2,2-trifluoroethylamine in step b) and 3-Isopropoxy-propylamine instead of (RS)-1-amino-3-methyl-1,3,4,5-tetrahydro-benzo[d]azepin-2-one in step d).

MS m/e (%): 436.3 (M+H$^+$, 100).

EXAMPLE 46

N-((3S)-1-Cyclopropylmethyl-2-oxo-2,3,4,5-tetrahydro-1H-benzo[b][1,4]diazepin-3-yl)-2-methyl-N'-(2,2,3,3,3-pentafluoro-propyl)-malonamide The title compound was obtained in comparable yields according to the procedures described for example 25 using cyclopropylmethyl bromide instead of methyl iodide in step a).

MS m/e (%): 463.5 (M+H$^+$, 100).

EXAMPLE 47

N-((3S)-1,5-Dimethyl-2-oxo-2,3,4,5-tetrahydro-1H-benzo[b][1,4]diazepin-3-yl)-2-methyl-N'-(2,2,3,3,3-pentafluoro-propyl)-malonamide a) ((3S)-1-Methyl-2-oxo-2,3,4,5-tetrahydro-1H-benzo[b][1,4]diazepin-3-yl)-carbamic acid tert-butyl ester To a solution of 5.0 g (18 mmol) (S)-(2-oxo-2,3,4,5-tetrahydro-1H-benzo[b][1,4]diazepin-3-yl)-carbamic acid tert-butyl ester in 80 ml of tetrahydrofuran at −75° C. 18 ml (18 mmol) of lithium bis(trimethylsilyl)amide solution (1M in tetrahydrofurane) was added. After stirring for 30 min at −75° C. the mixture was allowed to reach room temperature and 3.07 g (21.6 mmol) of methyl iodide was added. The mixture was stirred for 2.5 hours at room temperature and concentrated in vacuo. The residue was distributed between 1M NaHSO$_4$ solution and ethyl acetate. The combined organic layers were reextracted with water and dried (MgSO$_4$) to yield 4.95 g (94%) of (1-methyl-2-oxo-2,3,4,5-tetrahydro-1H-benzo[b][1,4]diazepin-3-yl)-carbamic acid tert-butyl ester as a white foam.

MS m/e (%): 292.0 (M+H$^+$, 100).

b) (S)-3-Amino-1,5-dimethyl-1,3,4,5-tetrahydro-benzo[b][1,4]diazepin-2-one

To 0.29 g (1 mmol) of (1-methyl-2-oxo-2,3,4,5-tetrahydro-1H-benzo[b][1,4]diazepin-3-yl)-carbamic acid tert-butyl ester in dimethylformamide (3 ml) 0.46 g (3.33 mmol) of potassium carbonate and 0.17 g (1.2 mmol) of methyl iodide were added and the mixture was stirred at room temperature overnight. Water (10 ml) was added and the mixture was extracted two times with ethyl acetate (10 ml each). The combined organic layers dried (MgSO$_4$) and purified by column chromatography (hexane/ethyl acetate=1:1) to yield 0.19 g (62%) of a white solid. This compound was dissolved in a mixture of 2 ml of dichlorometane and 2 ml of trifluoracetic acid and stirred for 2.5 h at room temperature. For workup the mixture was concentrated in vacuo, then dichloromethane was added and the mixture was extracted with sodium bicarbonate solution. The organic phase was dried (MgSO$_4$) and evaporated to yield 0.12 g of (S)-3-amino-1,5-dimethyl-1,3,4,5-tetrahydro-benzo[b][1,4] diazepin-2-one as a light yellow solid.

MS m/e (%): 206.4 (M+H$^+$, 100).

c) N-((3S)-1,5-Dimethyl-2-oxo-2,3,4,5-tetrahydro-1H-benzo[b][1,4]diazepin-3-yl)-2-methyl-N'-(2,2,3,3,3-pentafluoro-propyl)-malonamide The title compound was obtained in comparable yields according to the procedures described for example 20 using pentafluoropropylamine instead of 2,2,2-trifluoroethylamine in step b) and (S)-3-amino-1,5-dimethyl-1,3,4,5-tetrahydro-benzo[b][1,4]diazepin-2-one instead of (RS)-1-amino-3-methyl-1,3,4,5-tetrahydro-benzo[d]azepin-2-one in step d).

MS m/e (%): 437.5 (M+H$^+$, 100).

EXAMPLE 48

N-((3S)-5-Cyclopropylmethyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide The title compound was obtained in comparable yields according to the procedures described for example 47 using cyclopropylmethyl bromide instead of methyl iodide in step b).

MS m/e (%): 477.3 (M+H$^+$, 100).

EXAMPLE 49

N-[5-((3S)-4-Fluoro-benzyl)-1-methyl-2-oxo-2,3,4,
5-tetrahydro-1H-benzo[b][1,4]diazepin-3-yl]-2-methyl-N'-(2,2,3,3,3-pentafluoro-propyl)-malonamide The title compound was obtained in comparable yields according to the procedures described for example 47 using 4-fluorobenzyl bromide instead of methyl iodide in step b).
MS m/e (%): 531.3 (M+H$^+$, 100).

EXAMPLE 50

N-[(3S)-5-(4-Chloro-benzoyl)-1-cyclopropylmethyl-2-oxo-2,3,4,5-tetrahydro-1H-benzo[b][1,4]diazepin-3-yl]-2-methyl-N'-(2,2,3,3,3-pentafluoro-propyl)-malonamide The title compound was obtained in comparable yields according to the procedures described for example 26 using N-((3S)-1-cyclopropylmethyl-2-oxo-2,3,4,5-tetrahydro-1H-benzo[b][1,4]diazepin-3-yl)-2-methyl-N'-(2,2,3,3,3-pentafluoro-propyl)-malonamide instead of 2-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide and using 4-chlorobenzoyl chloride instead of benzoyl chloride.
MS m/e (%): 601.5 (M+H$^+$, 100).

EXAMPLE 51

N-(5-Cyclopropylmethyl-6-oxo-6,7-dihydro-5H-dibenzo[b,d]azepin-7-yl)-2-methyl-N'-(2,2,3,3,3-pentafluoro-propyl)-malonamide a) 5-Cyclopropylmethyl-5H,7H-dibenzo[b,d]azepin-6-one To a solution of 0.5 g (2.4 mmol) of 5H,7H-dibenzo[b,d]azepin-6-one in 6 ml of dimethylformamide at room temperature 0.143 g (3.58 mmol) of sodium hydride was added. After stirring for 1 hour at 60° C. 0.97 g (7.2 mmol) of cyclopropylmethyl bromide were added and stirring was continued at 60° C. overnight. After cooling to room temperature the mixture was was distributed between water and dichloromethane. The combined organic layers were reextracted with sodium sulphate solution and dried (MgSO$_4$). After concentration in vacuo the residue was purified by column chromatography (hexane/ethyl acetate=1:1) to yield 0.6 g (95%) of 5-cyclopropylmethyl-5H,7H-dibenzo[b,d]azepin-6-one as a white crystalline compound.
MS m/e (%): 264.1 (M+H$^+$, 100).

b) (RS)-7-Amino-5-cyclopropylmethyl-5H,7H-dibenzo[b,d]azepin-6-one

To a solution of 0.3 g (1.14 mmol) 5-cyclopropylmethyl-5H,7H-dibenzo[b,d]azepin-6-one in 5 ml of toluene 0.285 g (2.44 mmol) of isoamyl nitrite were added and the mixture was cooled to 0° C. A solution of 3.6 ml (1.83 mmol) of potassium bis(trimethylsilyl)amide (0.5 M in toluene) was added slowly and stirring was continued for 1 hour at this temperature. Sodium hydrogensulphate solution was added and the mixture was extracted two times with ethylacetate.

The combined organic layers were reextracted with water and dried (MgSO$_4$). After evaporation of the solvent 0.2 g of a white foam was obtained, that was dissolved in ethanol (5 ml). Palladium on carbon (90 mg) was added and the mixture was hydrogenated at 2.5 bar H$_2$ pressure for 32 hours. The catalyst was filtered off and the solvent was evaporated. The residue was partitioned between dichloromethane (5 ml) and 4N hydrochloric acid (2 ml). The aqueouos solution was separated, set to basic pH with sodium hydroxide and extracted 2 times with ethyl acetate. After drying (MgSO$_4$) and evaporation of the ethyl acetate 0.1 g (52%) of an off-white solid material was obtained.
MS m/e (%): 279.3 (M+H$^+$, 100).

c) N-(5-Cyclopropylmethyl-6-oxo-6,7-dihydro-5H-dibenzo[b,d]azepin-7-yl)-2-methyl-N'-(2,2,3,3,3-pentafluoro-propyl)-malonamide The title compound was obtained in comparable yields according to the procedures described for example 20 using 2,2,3,3,3-pentafluoropropylamine instead of 2,2,2-trifluoroethylamine in step b) and (RS)-7-amino-5-cyclopropylmethyl-5H,7H-dibenzo[b,d]azepin-6-one instead of (RS)-1-amino-3-methyl-1,3,4,5-tetrahydro-benzo[d]azepin-2-one in step d).
MS m/e (%): 508.4 (M–H$^+$, 100).

EXAMPLE 52

N-((3S)-1-Acetyl-4-oxo-2,3,4,5-tetrahydro-1H-benzo[b][1,4]diazepin-3-yl)-2-methyl-N'-(2,2,3,3,3-pentafluoro-propyl)-malonamide a) 5-Acetyl-3-amino-1,3,4,5-tetrahydro-benzo[b][1,4]diazepin-2-one A solution of 0.5 g (1.8 mmol) (S)-(2-oxo-2,3,4,5-tetrahydro-1H-benzo[b][1,4]diazepin-3-yl)-carbamic acid tert-butyl ester in 1.7 ml of acetic anhydride is stirred for 3 hours at 65° C. The mixture was put onto water (5 ml) and extracted two times with dichloromethane (10 ml each). The combined organic layers were dried (MgSO$_4$) and evaporated to yield 0.6 g of a light yellow foam. This compound was dissolved in a mixture of 2 ml of dichlorometane and 2 ml of trifluoracetic acid and stirred for 2.5 h at room temperature. For workup the mixture was concentrated in vacuo, then dichloromethane was added and the mixture was extracted with sodium bicarbonate solution. The organic phase was dried (MgSO$_4$) and evaporated to yield 0.31 g of (S)-1-acetyl-3-amino-1,3,4,5-tetrahydro-benzo[b][1,4]diazepin-2-one as a light yellow solid.
MS m/e (%): 220.4 (M+H$^+$, 100).

b) N-(1-Acetyl-4-oxo-2,3,4,5-tetrahydro-1H-benzo[b][1,4]diazepin-3-yl)-2-methyl-N'(2,2,3,3,3-pentafluoro-propyl)-malonamide The title compound was obtained in comparable yields according to the procedures described for example 20 using pentafluoropropylamine instead of 2,2,2-trifluoroethylamine in step b) and (S)-1-acetyl-3-amino-1,3,4,5-tetrahydro-benzo[b][1,4]diazepin-2-one instead of (RS)-1-amino-3-methyl-1,3,4,5-tetrahydro-benzo[d]azepin-2-one in step d).
MS m/e (%): 449.2 (M+H$^+$, 100).

EXAMPLE 53

N-((3S)-5-Acetyl-1-cyclopropylmethyl-2-oxo-2,3,4,5-tetrahydro-1H-benzo[b][1,4]diazepin-3-yl)-2-methyl-N'-(2,2,3,3,3-pentafluoro-propyl)-malonamide The title compound was obtained in comparable yields according to the procedures described for example 26 using N-((3S)-1-cyclopropylmethyl-2-oxo-2,3,4,5-tetrahydro-1H-benzo[b][1,4]diazepin-3-yl)-2-methyl-N'-(2,2,3,3,3-pentafluoro-propyl)-malonamide instead of 2-methyl-N-((3S)-

1-methyl-2-oxo-2,3,4,5-tetrahydro-1H-benzo[b][1,4]
diazepin-3-yl)-N'-(2,2,3,3,3-pentafluoro-propyl)-
malonamide and using acetyl chloride instead of benzoyl
chloride.

MS m/e (%): 503.2 (M–H⁺, 100).

EXAMPLE 54

N-(3-tert-Butoxy-propyl)-2-methyl-N'-(5-methyl-6-
oxo-6,7-dihydro-5H-dibenzo [b,d]azepin-7-yl)-mal-
onamide The title compound was obtained in comparable yields according to the procedures described for example 20 using (RS)-7-amino-5-methyl-5H,7H-dibenzo[b,d]azepin-6-one instead of 2,2,2-trifluoroethylamine in step b) and 3-tert-butoxy-propylamine instead of (RS)-1-amino-3-methyl-1,3, 4,5-tetrahydro-benzo[d]azepin-2-one in step d).

MS m/e (%): 396.2 (M—C₄H₉+H⁺, 100); 452.2 (M+H⁺, 43).

EXAMPLE 55

2-Methyl-N-((3S2-oxo-1-prop-2-ynyl-2,3,4,5-tet-
rahydro-1H-benzo[b][1,4]diazepin-3-yl)-N'-(2,2,3,3,
3-pentafluoro-propyl)-malonamide The title compound was obtained in comparable yields according to the procedures described for example 25 using prop-2-ynyl bromide instead of methyl iodide in step a).

MS m/e (%): 447.5 (M+H⁺, 100).

EXAMPLE 56

N-((3S)-5-Cyclopropanecarbonyl-1-methyl-2-oxo-2,
3,4,5-tetrahydro-1H-benzo[b][1,4]diazepin-3-yl)-2-
methyl-N'-(2,2,3,3,3-pentafluoro-propyl)-malona-
mide The title compound was obtained in comparable yields according to the procedures described for example 26 using cyclopropanecarbonyl chloride instead of benzoylchloride.

MS m/e (%): 491.5 (M+H⁺, 100).

EXAMPLE 57

2-Ethyl-N-(5-methyl-6-oxo-6,7-dihydro-5H-dibenzo
[b,d]azepin-7-yl)-N'-(2,2,3,3,3-pentafluoro-propyl)-
malonamide The title compound was obtained in comparable yields according to the procedures described for example 20 using diethyl ethyl-malonate instead of diethyl methyl-malonate in step a), (RS)-7-amino-5-methyl-5H,7H-dibenzo[b,d]azepin-6-one instead of 2,2,2-trifluoroethylamine in step b) and 2,2,3,3,3-pentafluoropropylamine instead of (RS)-1-amino-3-methyl-1,3,4,5-tetrahydro-benzo[d]azepin-2-one in step d).

MS m/e (%): 484.5 (M+H⁺, 100).

EXAMPLE 58

2-Isopropyl-N-(5-methyl-6-oxo-6,7-dihydro-5H-
dibenzo[b,d]azepin-7-yl)-N'-(2,2,3,3,3-pentafluoro-
propyl)-malonamide The title compound was obtained in comparable yields according to the procedures described for example 20 using diethyl isopropyl-malonate instead of diethyl methyl-malonate in step a), (RS)-7-amino-5-methyl-5H,7H-dibenzo[b, d]azepin-6-one instead of 2,2,2-trifluoroethylamine in step b) and 2,2,3,3,3-pentafluoropropylamine instead of (RS)-1-amino-3-methyl-1,3,4,5-tetrahydro-benzo[d]azepin-2-one in step d).

MS m/e (%): 498.5 (M+H⁺, 100).

EXAMPLE 59

N-((3S)-5-Cyclopropylmethyl-2-oxo-1-prop-2-ynyl-
2,3,4,5-tetrahydro-1H-benzo[b][1,4]diazepin-3-yl)-
2-methyl-N'-(2,2,3,3,3-pentafluoro-propyl)-malona-
mide The title compound was obtained in comparable yields according to the procedures described for example 47 using prop-2-ynyl bromide instead of methyl iodide in step a) and cyclopropylmethyl bromide instead of methyl iodide in step b).

MS m/e (%): 501.4 (M+H⁺, 100).

EXAMPLE 60

N-((3S)-5-Cyclopropanecarbonyl-2-oxo-1-prop-2-
ynyl-2,3,4,5-tetrahydro-1H-benzo[b][1,4]diazepin-3-
yl)-2-methyl-N'-(2,2,3,3,3-pentafluoro-propyl)-mal-
onamide The title compound was obtained in comparable yields according to the procedures described for example 26 using 2-methyl-N-((3S)-2-oxo-1-prop-2-ynyl-2,3,4,5-tetrahydro-1H-benzo[b][1,4]diazepin-3-yl)-N'-(2,2,3,3,3-pentafluoro-propyl)-malonamide instead of 2-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide and using cyclopropanecarbonyl chloride instead of benzoyl chloride.

MS m/e (%): 515.4 (M+H⁺, 100).

EXAMPLE 61

N-(5-Methyl-6-oxo-6,7-dihydro-5H-dibenzo[b,d]
azepin-7-yl)-N'-(2,2,3,3,3-pentafluoro-propyl)-mal-
onamide The title compound was obtained in comparable yields according to the procedures described for example 20 using diethyl malonate instead of diethyl methyl-malonate in step a), (RS)-7-amino-5-methyl-5H,7H-dibenzo[b,d]azepin-6-one instead of 2,2,2-trifluoroethylamine in step b) and 2,2,3,3,3-pentafluoropropylamine instead of (RS)-1-amino-3-methyl-1,3,4,5-tetrahydro-benzo[d]azepin-2-one in step d).

MS m/e (%): 456.5 (M+H⁺, 100).

EXAMPLE 62

2,2-Dimethyl-N-(5-methyl-6-oxo-6,7-dihydro-5H-
dibenzo[b,d]azepin-7-yl)-N'-(2,2,3,3,3-pentafluoro-
propyl)-malonamide The title compound was obtained in comparable yields according to the procedures described for example 20 using diethyl 2,2-dimethylmalonate instead of diethyl methyl-malonate in step a), (RS)-7-amino-5-methyl-5H,7H-dibenzo [b,d]azepin-6-one instead of 2,2,2-trifluoroethylamine in step b) and 2,2,3,3,3-pentafluoropropylamine instead of (RS)-1-amino-3-methyl-1,3,4,5-tetrahydro-benzo[d]azepin-2-one in step d).

MS m/e (%): 484.5 (M+H⁺, 100).

EXAMPLE 63

N-(3-Fluoro-5-methyl-6-oxo-6,7-dihydro-5H-dibenzo[b,d]azepin-7-yl)-2-methyl-N'-(2,2,3,3,3-pentafluoro-propyl)-malonamide The title compound was obtained in comparable yields according to the procedures described for example 20 using (RS)-7-amino-3-fluoro-5-methyl-5H,7H-dibenzo[b,d]azepin-6-one (prepared in the same manner as the 2-fluoroderivative in WO9932453) instead of 2,2,2-trifluoroethylamine in step b) and 2,2,3,3,3-pentafluoropropylamine instead of (RS)-1-amino-3-methyl-1,3,4,5-tetrahydro-benzo[d]azepin-2-one in step d).

MS m/e (%): 486.4 (M−H$^+$, 100).

EXAMPLE 64

N-(2-Fluoro-5-methyl-6-oxo-6,7-dihydro-5H-dibenzo[b,d]azepin-7-yl)-2-methyl-N'-(2,2,3,3,3-pentafluoro-propyl)-malonamide The title compound was obtained in comparable yields according to the procedures described for example 20 using (RS)-7-amino-2-fluoro-5-methyl-5H,7H-dibenzo[b,d]azepin-6-one instead of 2,2,2-trifluoroethylamine in step b) and 2,2,3,3,3-pentafluoropropylamine instead of (RS)-1-amino-3-methyl-1,3,4,5-tetrahydro-benzo[d]azepin-2-one in step d).

MS m/e (%): 486.2 (M−H$^+$, 100).

EXAMPLE 65

2-Methyl-N-(6-oxo-6,7-dihydro-5H-dibenzo[b,d]azepin-7-yl)-N'-(2,2,3,3,3-pentafluoro-propyl)-malonamide a) 5-(4-Methoxy-benzyl)-5H,7H-dibenzo[b,d]azepin-6-one To a solution of 0.82 g (4 mmol) of 5H,7H-dibenzo[b,d]azepin-6-one in 15 ml of dimethylformamide at room temperature 0.20 g (5 mmol) of sodium hydride 55% in oil was added. After stirring for 30 min at room temperature 0.75 g (5 mmol) of p-methoxybenzyl chloride were added and stirring was continued at room temperature for 2 hours. For workup the mixture was distributed between water and ethyl acetate. The organic layer was re-extracted with 1 N hydrochloric acid and the aqueous layers were washed with ethyl acetate. The combined organic layers were dried (MgSO4) and concentrated in vacuo. The residue was purified by column chromatography (hexane/ethyl acetate=1:1) to yield 1.175 g (91%) of 5-(4-methoxybenzyl)-5H,7H-dibenzo[b,d]azepin-6-one as a colourless oil.

MS m/e (%): 330.4 (M+H$^+$, 100).

b) (RS)-7-Amino-5-(4-methoxy-benzyl)-5H,7H-dibenzo[b,d]azepin-6-one

To a solution of 1.15 g (3.5 mmol) 5-(4-methoxybenzyl)-5H,7H-dibenzo[b,d]azepin-6-one in 15 ml of toluene 0.836 g (7 mmol) of isoamyl nitrite were added and the mixture was cooled to 0° C. A solution of 21.4 ml (10.5 mmol) of potassium bis(trimethylsilyl)amide (0.5 M in toluene) was added slowly and stirring was continued for 2 hours at this temperature. Sodium hydrogensulphate solution was added and the mixture was extracted two times with ethylacetate. The combined organic layers were re-extracted with water and dried (MgSO4). After evaporation of the solvent a solid was obtained, that was purified by column chromatography (dichloromethane/methanol=95:5) to yield 1.03 g (81%) oxime. This compound was dissolved in ethanol (5 ml) and 1.5 ml of 2N hydrochloric acid were added. Palladium on carbon (10%, Degussa 1835, 100 mg) was added and the mixture was hydrogenated at 5 bar H2 pressure for 24 hours at room temperature. The catalyst was filtered off and the solvent was evaporated. The residue was partitioned between dichloromethane (5 ml) and 4N hydrochloric acid (2 ml). The aqueous solution was separated, set to basic pH with sodium hydroxide and extracted 2 times with ethyl acetate. After drying (MgSO4) and evaporation of the ethyl acetate 0.8 g (63%) of a white solid material was obtained.

MS m/e (%): 345.3 (M+H$^+$, 100).

c) (RS)-7-Amino-5H,7H-dibenzo[b,d]azepin-6-one

To a solution of 0.1 g (0.29 mmol) (RS)-7-amino-5-(4-methoxy-benzyl)-5H,7H-dibenzo[b,d]azepin-6-one in 8 ml of dichloromethane at 0° C. temperature 0.67 ml (8.7 mmol) of trifluoroacetic acid and 0.25 ml of trifluoromethansulfonic acid (2.9 mmol) were added and the mixture was stirred for 4 hours at room temperature. After concentration of the mixture at 40° C. in vacuo an aqueous NaHCO$_3$ solution was added and the mixture extracted two times with ethyl acetate. The combined organic layers were dried (MgSO$_4$). After evaporation of the solvent a light yellow oil was obtained, that was used directly in the next step.

d) (RS)-2-Methyl-N-(6-oxo-6,7-dihydro-5H-dibenzo[b,d]azepin-7-yl)-N'-(2,2,3,3,3-pentafluoro-propyl)-malonamide The title compound was obtained in comparable yields according to the procedures described for example 20 using and 2,2,3,3,3-pentafluoropropylamine instead of 2,2,2-trifluoroethylamine in step b) and (RS)-7-amino-5H,7H-dibenzo[b,d]azepin-6-one instead of (RS)-1-amino-3-methyl-1,3,4,5-tetrahydro-benzo[d]azepin-2-one in step d).

MS m/e (%): 456.5 (M+H$^+$, 100).

EXAMPLE 66

N-((S)-6-Oxo-6,7-dihydro-5H-dibenzo[b,d]azepin-7-yl)-N'-(2,2,3,3,3-pentafluoro-propyl)-malonamide a) (S)-7-amino-5-(4-methoxy-benzyl)-5H,7H-dibenzo[b,d]azepin-6-one Racemic (RS)-7-amino-5-(4-methoxy-benzyl)-5H,7H-dibenzo[b,d]azepin-6-one was separated by chromatography on Chiralpak AD with isopropanol/heptane 1:3 as solvent to yield (S)-7-amino-5-(4-methoxy-benzyl)-5H,7H-dibenzo[b,d]azepin-6-one, [α] 589=−146° (1% in CHCl$_3$) and (R)-7-amino-5-(4-methoxy-benzyl)-5H,7H-dibenzo[b,d]azepin-6-one, [α] 589=+148° (1% in CHCl$_3$).

b) (S)-N-(6-oxo-6,7-dihydro-5H-dibenzo[b,d]azepin-7-yl)-N'-(2,2,3,3,3-pentafluoro-propyl)-malonamide The methoxybenzyl group of (S)-7-amino-5-(4-methoxy-benzyl)-5H,7H-dibenzo[b,d]azepin-6-one was removed according to the method described in section c) of example 65 and the resulting (S)-7-amino-5H,7H-dibenzo[b,d]azepin-6-one was coupled with N-(2,2,3,3,3-pentafluoropropyl)-malonamic acid according to the method described in section d) of example 65 to yield (S)-N-(6-oxo-6,7-dihydro-5H-dibenzo[b,d]azepin-7-yl)-N'-(2,2,3,3,3-pentafluoro-propyl)-malonamide,

[α] 589=−79.7° (1% in MeOH), MS m/e (%): 442.4 (M+H$^+$, 100).

EXAMPLE 67

2,2-Dimethyl-N-((S)-6-oxo-6,7-dihydro-5H-dibenzo[b,d]azepin-7-yl)-N'-(2,2,3,3,3-pentafluoro-propyl)-malonamide (S)-7-Amino-5H,7H-dibenzo[b,d]azepin-6-one was coupled with 2,2-dimethyl-N-(2,2,3,3,3-pentafluoro-propyl)-malonamic acid in analogy to the description in examples 65 and 66 to yield 2,2-dimethyl-N-((S)-6-oxo-6,7-dihydro-5H-dibenzo[b,d]azepin-7-yl)-N'-(2,2,3,3,3-pentafluoro-propyl)-malonamide,

[α] 589=−38.8° (1% in CHCl$_3$), MS m/e (%): 470.3 (M+H$^+$, 100).

EXAMPLE 68

(−)-2-Methoxy-N-((S)-6-oxo-6,7-dihydro-5H-dibenzo[b,d]azepin-7-yl)-N'-(2,2,3,3,3-pentafluoro-propyl)-malonamide a) 2-Methoxy-N-(2,2,3,3,3-pentafluoro-propyl)-malonamic acid methyl ester 2-Methoxy-malonic acid monomethyl ester was coupled with 2,2,3,3,3-pentafluoro-propylamine in analogy to the description in Example 73 to yield 2-methoxy-N-(2,2,3,3,3-pentafluoro-propyl)-malonamic acid methyl ester as colourless oil, MS m/e (%): 280.0 (M+H$^+$, 100).

b) 2-Methoxy-N-(2,2,3,3,3-pentafluoro-propyl)-malonamic acid

2-Methoxy-N-(2,2,3,3,3-pentafluoro-propyl)-malonamic acid methyl ester was saponified in analogy to the procedure of example 75b to yield 2-methoxy-N-(2,2,3,3,3-pentafluoro-propyl)-malonamic acid as white solid, MS m/e (%): 266.0 (M+H$^+$, 100).

c) (−)-2-Methoxy-N-((S)-6-oxo-6,7-dihydro-5H-dibenzo[b,d]azepin-7-yl)-N'-(2,2,3,3,3-pentafluoro-propyl)-malonamide (S)-7-Amino-5H,7H-dibenzo[b,d]azepin-6-one was coupled with 2-methoxy-N-(2,2,3,3,3-pentafluoro-propyl)-malonamic acid in analogy to the description in examples 65 and 66 to yield (−)-2-methoxy-N-(6-oxo-6,7-dihydro-5H-dibenzo[b,d]azepin-7-yl)-N'-(2,2,3,3,3-pentafluoro-propyl)-malonamide as white solid,

[α] 589=−87.6° (1% in MeOH), MS m/e (%): 472.0 (M+H$^+$, 100).

EXAMPLE 69

(2R)-2-Fluoro-2-methyl-N-((S)-6-oxo-6,7-dihydro-5H-dibenzo[b,d]azepin-7-yl)-N'-(2,2,3,3,3-pentafluoro-propyl)-malonamide a) (2S)-2-Fluoro-2-methyl-N-[(S)-6-oxo-6,7-dihydro-5H-dibenzo[b,d]azepin-7-yl]-malonamic acid ethyl ester In an analogous manner to that described in Example 1 a), the condensation of (S)-7-amino-5H,7H-dibenzo[b,d]azepin-6-one and (2S)-2-fluoro-2-methyl-malonic acid mono ethyl ester (96.9% e.e.) yielded the title compound as a white solid; MS: m/e=371 (M+H$^+$). The (2S)-2-fluoro-2-methyl-malonic acid mono ethyl ester was obtained by stereoselective hydrolysis of the corresponding diester by *Candida cylindracea* hydrolase following the procedure described in J. Org. Chem. 1986, 51, 1003-6.

b) (2S)-2-Fluoro-2-methyl-N-[(S)-6-oxo-6,7-dihydro-5H-dibenzo[b,d]azepin-7-yl]-malonamic acid In an analogous manner to that described in Example WC b), the hydrolysis of the (2S)-2-fluoro-2-methyl-N-[(S)-6-oxo-6,7-dihydro-5H-dibenzo[b,d]azepin-7-yl]-malonamic acid ethyl ester under basic conditions yielded the title compound as white foam;

MS: m/e=341 (M−H)$^−$.

c) (2R)-2-Fluoro-2-methyl-N-[(S)-6-oxo-6,7-dihydro-5H-dibenzo[b,d]azepin-7-yl]-N'-(2,2,3,3,3-pentafluoro-propyl)-malonamide In an analogous manner to that described in Example 1 c), the condensation of (2S)-2-fluoro-2-methyl-N-[(S)-6-oxo-6,7-dihydro-5H-dibenzo[b,d]azepin-7-yl]-malonamic acid and 2,2,3,3,3-pentafluoro-propylamine yielded the title compound as a white solid; MS: m/e=474 (M+H)$^+$; optical integrity 96.4% d.e.

EXAMPLE 70

(2S)-2-Fluoro-2-methyl-N-[(S6-oxo-6,7-dihydro-5H-dibenzo[b,d]azepin-7-yl]-N'-(2,2,3,3,3-pentafluoro-propyl)-malonamide In an analogous manner to that described in Example 20 d), the condensation of (S)-7-amino-5H,7H-dibenzo[b,d]azepin-6-one and (2S)-2-fluoro-2-methyl-N-(2,2,3,3,3-pentafluoro-propyl)-malonamic acid yielded the title compound as a white solid;

MS: m/e=474 (M+H)$^+$.

EXAMPLE 71

N-((S)-5-Cyclopropylmethyl-6-oxo-6,7-dihydro-5H-dibenzo[b,d]azepin-7-yl)-N'-(2,2,3,3,3-pentafluoro-propyl)-malonamide a) (S)-7-amino-5-cyclopropylmethyl-5H,7H-dibenzo[b,d]azepin-6-one (RS)-7-Amino-5-cyclopropylmethyl-5H,7H-dibenzo[b,d]azepin-6-one was separated by HPLC on Chiralpak AD with isopropanol/heptane 1:4 to give (S)-7-amino-5-cyclopropylmethyl-5H,7H-dibenzo[b,d]azepin-6-one, [α] 589=−162° (1% in MeOH), and (R)-7-amino-5-cyclopropylmethyl-5H,7H-dibenzo[b,d]azepin-6-one, [α] 589=+163° (1% in MeOH).

Assignment of the absolute configuration by derivatisation with (−)—(S)-naproxen and x-ray analysis of the derivative (S)-N-((R)-5-cyclopropylmethyl-6-oxo-6,7-dihydro-5H-dibenzo[b,d]azepin-7-yl)-2-(6-methoxy-naphthalen-2-yl)-propionamide. A tetrahydrofurane solution of 0.05 g (0.18 mmol) (+)-7-amino-5-cyclopropylmethyl-5H,7H-dibenzo[b,d]azepin-6-one was reacted overnight at room temperature with 0.04 g (0.18 mmol) (+)-(S)-naproxen, 0.03 g (0.18 mmol) 1-hydroxybenzotriazole, 0.063 µl (0.36 mmol) diisopropylethylamine and 0.04 g (0.18 mmol) N-(3-dimethylaminopropyl)-N'-ethyl-carbodiimid-hydrochlorid. Extraction with 1 N aqueous hydrochloric acid/dichloromethane and chromatography on silicagel yielded 0.09 g (97%) (S)-N-((R)-5-cyclopropylmethyl-6-oxo-6,7-dihydro-5H-dibenzo[b,d]azepin-7-yl)-2-(6-methoxy-naphthalen-2-yl)-propionamide as white solid which was crystallized from ethanol.

mp.: 151–152° C., MS m/e (%): 491.4 (M+H$^+$, 100).

b) N-((S)-5-cyclopropylmethyl-6-oxo-6,7-dihydro-5H-dibenzo[b,d]azepin-7-yl)-N'-(2,2,3,3,3-pentafluoro-propyl)-malonamide 0.11 g (0.38 mmol) (S)-7-Amino-5-cyclopropylmethyl-5H,7H-dibenzo[b,d]azepin-6-one and 0.09 g (0.38 mmol) 3-oxo-3-(2,2,3,3,3-pentafluoro-propylamino)-propanoic acid in 10 ml tetrahydrofuran were reacted with 0.06 g (0.38 mmol) 1-hydroxybenzotriazole hydrate, 0.13 ul (0.76 mmol) diisopropylethylamine and 0.7 g (0.38 mmol) N-(3-dimethylaminopropyl)-N'-ethyl-carbodiimid-hydrochlorid at 0° C. for 4 hours. After stirring at room temperature over night the solvent was removed by distillation and the residue purified by chromatography on silicagel with heptane/ethylacetate (gradient 100–0/0-100) to yield 0.17 g (89%) N-((S)-5-cyclopropylmethyl-6-oxo-6,7-dihydro-5H-dibenzo[b,d]azepin-7-yl)-N'-(2,2,3,3,3-pentafluoro-propyl)-malonamide as white solid.

[α] 589=−63.9° (1% in CHCl$_3$), MS m/e (%): 496.3 (M+H$^+$, 100).

EXAMPLE 72

(R)-N-((S)-5-Cyclopropylmethyl-6-oxo-6,7-dihydro-5H-dibenzo[b,d]azepin-7-yl)-2-methyl-N'-(2,2,3,3,3-pentafluoro-propyl)-malonamide and

EXAMPLE 73

(S)-N-((S)-5-Cyclopropylmethyl-6-oxo-6,7-dihydro-5H-dibenzo[b,d]azepin-7-yl)-2-methyl-N'-(2,2,3,3,3-pentafluoro-propyl)-malonamide 0.15 g (0.54 mmol) (S)-7-amino-5-cyclopropylmethyl-5H,7H-dibenzo[b,d]azepin-6-one and 0.13 g (0.54 mmol) 2-methyl-3-oxo-3-(2,2,3,3,3-pentafluoro-propylamino)-propanoic acid in 13 ml tetrahydrofuran were reacted with 0.07 g (0.54 mmol) 1-hydroxybenzotriazole hydrate, 0.19 ul (1.08 mmol) diisopropylethylamine and 0.11 g (0.54 mmol) N-(3-dimethylaminopropyl)-N'-ethyl-carbodiimid-hydrochlorid with stirring at room temperature over night. Extraction with 1N aqueous hydrochloric acid/dichloromethane and chromatography on silicagel with ethylacetate gave 0.22 g solid material which was separated by chromatography on Chiralpak AD with heptane/isopropanol 80/20 to yield 0.10 g (R)-N-((S)-5-cyclopropylmethyl-6-oxo-6,7-dihydro-5H-dibenzo[b,d]azepin-7-yl)-2-methyl-N'-(2,2,3,3,3-pentafluoro-propyl)-malonamide [α] 589=−74.6° (1% in CHCl$_3$), MS m/e (%): 510.3 (M+H$^+$, 100) as white solid and 0.09 g (S)-N-((S)-5-cyclopropylmethyl-6-oxo-6,7-dihydro-5H-dibenzo[b,d]azepin-7-yl)-2-methyl-N'-(2,2,3,3,3-pentafluoro-propyl)-malonamide [α] 589=−63.8° (1% in CHCl$_3$), MS m/e (%): 510.3 (M+H$^+$, 100) as white solid.

EXAMPLE 74

N-((S)-5-Cyclopropylmethyl-6-oxo-6,7-dihydro-5H-dibenzo[b,d]azepin-7-yl)-2,2-dimethyl-N'-(2,2,3,3,3-pentafluoro-propyl)-malonamide (S)-7-amino-5-cyclopropylmethyl-5H,7H-dibenzo[b,d]azepin-6-one was coupled with 2,2-dimethyl-N-(2,2,3,3,3-pentafluoro-propyl)-malonamic acid in analogy to the description in example 73 to yield N-((S)-5-cyclopropylmethyl-6-oxo-6,7-dihydro-5H-dibenzo[b,d]azepin-7-yl)-2,2-dimethyl-N'-(2,2,3,3,3-pentafluoro-propyl)-malonamide as white solid.

[α] 589=−60.4° (1% in CHCl$_3$), MS m/e (%): 524.3 (M+H$^+$, 100).

EXAMPLE 75

(R)-N-((S)-5-Cyclopropylmethyl-6-oxo-6,7-dihydro-5H-dibenzo[b,d]azepin-7-yl)-2-fluoro-2-methyl-N'-(2,2,3,3,3-pentafluoro-propyl)-malonamide a) (S)-N-((S)-5-cyclopropylmethyl-6-oxo-6,7-dihydro-5H-dibenzo[b,d]azepin-7-yl)-2-fluoro-2-methyl-malonamic acid ethyl ester (S)-7-amino-5-cyclopropylmethyl-5H,7H-dibenzo[b,d]azepin-6-one was coupled with (S)-2-fluoro-2-methyl-malonic acid monoethyl ester in analogy to the description in example 73 to yield (S)-N-((S)-5-cyclopropylmethyl-6-oxo-6,7-dihydro-5H-dibenzo[b,d]azepin-7-yl)-2-fluoro-2-methyl-malonamic acid ethyl ester as colourless oil.

MS m/e (%): 425.4 (M+H$^+$, 100).

b) (S)-N-((S)-5-cyclopropylmethyl-6-oxo-6,7-dihydro-5H-dibenzo[b,d]azepin-7-yl)-2-fluoro-2-methyl-malonamic Acid 0.22g (0.52 mmol) (S)-N-((S)-5-cyclopropylmethyl-6-oxo-6,7-dihydro-5H-dibenzo[b,d]azepin-7-yl)-2-fluoro-2-methyl-malonamic acid ethyl ester in 3 ml tetrahydrofurane was reacted with a solution of 0.02 g (0.52 mmol) lithium hydroxide monohydrate in 1 ml water at room temperature for 2 hours. Evaporation of the tetrahydrofurane, extraction with diethylether, acidification with 0.5 ml 1 N aqueous hydrochloric acid and extraction with ethylacetate gave 0.18 g (S)-N-((S)-5-cyclopropylmethyl-6-oxo-6,7-dihydro-5H-dibenzo[b,d]azepin-7-yl)-2-fluoro-2-methyl-malonamic acid as white solid.

MS m/e (%): 397.4 (M+H$^+$, 100).

c) (R)-N-((S)-5-cyclopropylmethyl-6-oxo-6,7dihydro-5H-dibenzo[b,d]azepin-7-yl)-2-fluoro-2-methyl-N'-(2,2,3,3,3-pentafluoro-propyl)-malonamide (S)-N-((S)-5-cyclopropylmethyl-6-oxo-6,7-dihydro-5H-dibenzo[b,d]azepin-7-yl)-2-fluoro-2-methyl-malonamic acid was coupled with 2,2,3,3,3-pentafluoropropylamine in analogy to the procedure described for RJR 7 to yield (R)-N-((S)-5-cyclopropylmethyl-6-oxo-6,7-dihydro-5H-dibenzo[b,d]azepin-7-yl)-2-fluoro-2-methyl-N'-(2,2,3,3,3-pentafluoro-propyl)-malonamide as white solid.

[α] 589=−45.7° (1% in CHCl$_3$), MS m/e (%): 528.2 (M+H$^+$, 100).

EXAMPLE 76

N-((S)-5-Cyclopropylmethyl-6-oxo-6,7-dihydro-5H-dibenzo[b,d]azepin-7-yl)-2-methoxy-N'-(2,2,3,3,3-pentafluoro-propyl)-malonamide (S)-7-amino-5-cyclopropylmethyl-5H,7H-dibenzo[b,d]azepin-6-one was coupled with 2-methoxy-N-(2,2,3,3,3-pentafluoro-propyl)-malonamic acid in analogy to the description in example 73 to yield N-((S)-5-cyclopropylmethyl-6-oxo-6,7-dihydro-5H-dibenzo[b,d]azepin-7-yl)-2-methoxy-N'-(2,2,3,3,3-pentafluoro-propyl)-malonamide as white solid.

[α] 589=−105.5° (1% in MeOH), MS m/e (%): 526.3 (M+H$^+$, 100).

EXAMPLE 77

N-((S)-5-Cyclopropylmethyl-6-oxo-6,7-dihydro-5H-dibenzo[b,d]azepin-7-yl)-N'-(3,3,4,4,4-pentafluoro-butyl)-malonamide (S)-7-amino-5-cyclopropylmethyl-5H,7H-dibenzo[b,d]azepin-6-one was coupled with N-(3,3,4,4,4-pentafluoro-butyl)-malonamic acid in analogy to the description in example 73 to yield N-((S)-5-cyclopropylmethyl-6-oxo-6,7-dihydro-5H-dibenzo[b,d]azepin-7-yl)-N'-(3,3,4,4,4-pentafluoro-butyl)-malonamide as white solid.

[α] 589=−57.5° (1% in $CHCl_3$), MS m/e (%): 510.1 ($M+H^+$, 100).

EXAMPLE 78

N-((S)-5-Cyclopropylmethyl-6-oxo-6,7-dihydro-5H-dibenzo[b,d]azepin-7-yl)-2-methyl-N'-(3,3,4,4,4-pentafluoro-butyl)-malonamide a) 2-Methyl-N-(3,3,4,4,4-pentafluoro-butyl)-malonamic acid ethyl ester 2-Methyl-malonic acid monoethyl ester was coupled with 3,3,4,4,4-pentafluoro-butylamine in analogy to the description in example 73 to yield 2-methyl-N-(3,3,4,4,4-pentafluoro-butyl)-malonamic acid ethyl ester as colourless oil.

MS m/e (%): 292.1 ($M+H^+$, 100).

b) 2-Methyl-N-(3,3,4,4,4-pentafluoro-butyl)-malonamic Acid

2-Methyl-N-(3,3,4,4,4-pentafluoro-butyl)-malonamic acid ethyl ester was saponified in analogy to the procedure of example 75b to yield 2-methyl-N-(3,3,4,4,4-pentafluoro-butyl)-malonamic acid as white solid.

MS m/e (%): 262.1 ($M-H^+$, 100).

c) N-((S)-5-Cyclopropylmethyl-6-oxo-6,7-dihydro-5H-dibenzo[b,d]azepin-7-yl)-2-methyl-N'-(3,3,4,4,4-pentafluoro-butyl)-malonamide (S)-7-amino-5-cyclopropylmethyl-5H,7H-dibenzo[b,d]azepin-6-one was coupled with 2-methyl-N-(3,3,4,4,4-pentafluoro-butyl)-malonamic acid in analogy to the description in example 73 to yield N-((S)-5-cyclopropylmethyl-6-oxo-6,7-dihydro-5H-dibenzo[b,d]azepin-7-yl)-2-methyl-N'-(3,3,4,4,4-pentafluoro-butyl)-malonamide (epimers) as white solid.

MS m/e (%): 524.2 ($M+H^+$, 100).

EXAMPLE 79

N-((S)-5-Cyclopropylmethyl-6-oxo-6,7-dihydro-5H-dibenzo[b,d]azepin-7-yl)-2,2-dimethyl-N'-(3,3,4,4,4-pentafluoro-butyl)-malonamide (S)-7-amino-5-cyclopropylmethyl-5H,7H-dibenzo[b,d]azepin-6-one was coupled with 2,2-dimethyl-N-(3,3,4,4,4-pentafluoro-butyl)-malonamic acid in analogy to the description in example 73 to yield N-((S)-5-cyclopropylmethyl-6-oxo-6,7-dihydro-5H-dibenzo[b,d]azepin-7-yl)-2,2-dimethyl-N'-(3,3,4,4,4-pentafluoro-butyl)-malonamide (epimers) as white solid, [α] 589=−64.9° (1% in $CHCl_3$), MS m/e (%): 538.3 ($M+H^+$, 100).

EXAMPLE 80

(R)-N-((S)-5-Cyclopropylmethyl-6-oxo-6,7-dihydro-5H-dibenzo[b,d]azepin-7-yl)-2-fluoro-2-methyl-N'-(3,3,4,4,4-pentafluoro-butyl)-malonamide (S)-N-((S)-5-cyclopropylmethyl-6-oxo-6,7-dihydro-5H-dibenzo[b,d]azepin-7-yl)-2-fluoro-2-methyl-malonamic acid was coupled with 3,3,4,4,4-pentafluoro-butylamine in analogy to the procedure described for example 73 to yield (R)-N-((S)-5-cyclopropylmethyl-6-oxo-6,7-dihydro-5H-dibenzo[b,d]azepin-7-yl)-2-fluoro-2-methyl-N'-(3,3,4,4,4-pentafluoro-butyl)-malonamide as white solid.

[α] 589=−56.7° (1% in $CHCl_3$), MS m/e (%): 542.0 ($M+H^+$, 100).

EXAMPLE 81

N-(5-Isopropyl-6-oxo-6,7-dihydro-5H-dibenzo[b,d]azepin-7-yl)-2-methyl-N'-(2,2,3,3,3-pentafluoro-propyl)-malonamide The title compound was obtained in comparable yields according to the procedures described for example 65 using and 2-iodopropane instead of p-methoxybenzyl chloride in step a) while step c) was omitted and directly continued with step d).

MS m/e (%): 496.1 ($M-H^+$, 100).

EXAMPLE 82

N-(5-Isopropyl-6-oxo-6,7-dihydro-5H-dibenzo[b,d]azepin-7-yl)-2,2-dimethyl-N'-(2,2,3,3,3-pentafluoro-propyl)-malonamide The title compound was obtained in comparable yields according to the procedures described for example 65 using and 2-iodopropane instead of p-methoxybenzyl chloride in step a) while step c) was omitted and 2,2-dimethyl-N-(2,2,3,3,3-pentafluoro-propyl)-malonamic acid was used instead of 2-methyl-N-(2,2,3,3,3-pentafluoro-propyl)-malonamic acid in step d).

MS m/e (%): 510.3 ($M-H^+$, 100).

EXAMPLE 83

N-((S)-5-Methyl-6-oxo-6,7-dihydro-5H-dibenzo[b,d]azepin-7-yl)-N'-(2,2,3,3,3-pentafluoro-propyl)-malonamide (S)-7-Amino-5-methyl-5H,7H-dibenzo[b,d]azepin-6-one was coupled with N-(2,2,3,3,3-pentafluoro-propyl)-malonamic acid in analogy to the description in example 73 to yield N-((S)-5-Methyl-6-oxo-6,7-dihydro-5H-dibenzo[b,d]azepin-7-yl)-N'-(2,2,3,3,3-pentafluoro-propyl)-malonamide as white solid.

[α] 589=−52.7° (1% in $CHCl_3$), MS m/e (%): 456.4 ($M+H^+$, 100).

EXAMPLE 84

2,2-Dimethyl-N-((S)-5-methyl-6-oxo-6,7-dihydro-5H-dibenzo[b,d]azepin-7-yl)-N-(2,2,3,3,3-pentafluoro-propyl)-malonamide (S)-7-Amino-5-methyl-5H,7H-dibenzo[b,d]azepin-6-one was coupled with 2,2-dimethyl-N-(3,3,4,4,4-pentafluorobutyl)-malonamic acid in analogy to the description example 73 to yield 2,2-dimethyl-N-((S)-5-methyl-6-oxo-6,7-dihydro-5H-dibenzo[b,d]azepin-7-yl)-N-(2,2,3,3,3-pentafluoro-propyl)-malonamide as white solid. [α] 589=−53.8° (1% in CHCl$_3$), MS m/e (%): 484.0 (M+H$^+$, 100).

EXAMPLE 85

(2R)-2-Fluoro-2-methyl-N-[(S)-5-methyl-6-oxo-6,7-dihydro-5H-dibenzo[b,d]azepin-7-yl]-N'-(2,2,3,3,3-pentafluoro-propyl)-malonamide a) (2S)-2-Fluoro-2-methyl-N-((S)-5-methyl-6-oxo-6,7-dihydro-5H-dibenzo[b,d]azepin-7-yl)-malonamic acid ethyl ester In an analogous manner to that described in Example 1 a), the condensation of (S)-7-amino-5-methyl-5H,7H-dibenzo[b,d]azepin-6-one and (2S)-2-fluoro-2-methyl-malonic acid mono ethyl ester yielded the title compound as a colourless oil;

MS: m/e=385 (M+H)$^+$.

The (2S)-2-fluoro-2-methyl-malonic acid mono ethyl ester (optical integrity 91% e.e.) was obtained by stereoselective hydrolysis of the corresponding diester by *Candida cylindracea* hydrolase following the procedure described in J.Org.Chem. 1986, 51, 1003-6.

b) (2S)-2-Fluoro-2-methyl-N-((S)-5-methyl-6-oxo-6,7-dihydro-5H-dibenzo[b,d]azepin-7-yl)-malonamic acid A solution of 75 mg (0.2 mmol) of (2S)-2-fluoro-2-methyl-N-((S)-5-methyl-6-oxo-6,7-dihydro-5H-dibenzo[b,d]azepin-7-yl)-malonamic acid ethyl ester in 1 ml of tetrahydrofurane was treated for 2 h at room temperature with a solution of 8 mg (0.2 mmol) of lithium hydroxide monohydrate in 0.5 ml of water. For the working-up, the tetrahydrofurane was evaporated under reduced pressure and the remaining aqueous layer was extracted twice with 10 ml of diethylether. The combined organic layers were washed with 5 ml of water and, thereafter, the combined aqueous layers were acidified with 0.025 ml of hydrochloric acid (25%). Thereupon, the aqueous layer was extracted three times with 15 ml of ethyl acetate. The organic layers were washed with 15 ml of a saturated solution of sodium chloride, then combined, dried over sodium sulphate, and evaporated under reduced pressure. There were obtained 69 mg (99% of theory) of the title compound as a white foam;

MS: m/e=355 (M−H)$^-$.

c) (2R)-2-Fluoro-2-methyl-N-r(S)-5-methyl-6-oxo-6,7-dihydro-5H-dibenzo[b,d]azepin-7yl-N'-(2,2,3,3,3-pentafluoro-propyl)-malonamide In an analogous manner to that described in Example 1 c), the condensation of (2S)-2-fluoro-2-methyl-N-((S)-5-methyl-6-oxo-6,7-dihydro-5H-dibenzo[b,d]azepin-7-yl)-malonamic acid and 2,2,3,3,3-pentafluoro-propylamine yielded the title compound as a white foam; MS: m/e=488 (M+H)$^+$; optical integrity 94% d.e.

EXAMPLE 86

(2S)-2-Fluoro-2-methyl-N-[(S)-5-methyl-6-oxo-6,7-dihydro-5H-dibenzo[b,d]azepin-7-yl]-N'-(2,2,3,3,3-pentafluoro-propyl)-malonamide In an analogous manner to that described in Example 20 d), the condensation of (S)-7-amino-5-methyl-5H,7H-dibenzo[b,d]azepin-6-one and (2S)-2-fluoro-2-methyl-N-(2,2,3,3,3-pentafluoro-propyl)-malonamic acid yielded the title compound as a white solid;

MS: m/e=488 (M+H)$^+$.

The (2S)-2-fluoro-2-methyl-N-(2,2,3,3,3-pentafluoro-propyl)-malonamic acid was obtained in a reaction sequence analogous to that leading to (2RS)-methyl-N-(2,2,2-trifluoro-ethyl)-malonamic acid [Example 20 c)] by replacing (2RS)-methyl-malonic acid monoester by (2S)-2-fluoro-2-methyl-malonic acid monoester.

EXAMPLE 87

2-Methoxy-N-((S)-5-methyl-6-oxo-6,7-dihydro-5H-dibenzo[b,d]azepin-7-yl)-N'-(2,2,3,3,3-pentafluoro-propyl)-malonamide (S)-7-Amino-5-methyl-5H,7H-dibenzo[b,d]azepin-6-one was coupled with 2-methoxy-N-(2,2,3,3,3-pentafluoro-propyl)-malonamic acid in analogy to the description in example 73 to yield 2-methoxy-N-((S)-5-methyl-6-oxo-6,7-dihydro-5H-dibenzo[b,d]azepin-7-yl)-N'-(2,2,3,3,3-pentafluoro-propyl)-malonamide as white solid. [α] 589=−71.8° (1% in CHCl$_3$), MS m/e (%): 486.4 (M+H$^+$, 100).

EXAMPLE 88

N-((S)-5-Methyl-6-oxo-6,7-dihydro-5H-dibenzo[b,d]azepin-7-yl)-N'-(3,3,4,4,4-pentafluoro-butyl)-malonamide (S)-7-Amino-5-methyl-5H,7H-dibenzo[b,d]azepin-6-one was coupled with N-(3,3,4,4,4-pentafluoro-butyl)-malonamic acid in analogy to the description example 73 to yield N-((S)-5-methyl-6-oxo-6,7-dihydro-5H-dibenzo[b,d]azepin-7-yl)-N'-(3,3,4,4,4-pentafluoro-butyl)malonamide as white solid.

[α] 589=−51.4° (1% in CHCl$_3$), MS m/e (%): 470.1 (M+H$^+$, 100).

EXAMPLE 89

2,2-Dimethyl-N-[(S)-6-oxo-5-(2,2,2-trifluoro-ethyl)-6,7-dihydro-5H-dibenzo[b,d]azepin-7-yl]-N'-(2,2,3,3,3-pentafluoro-propyl)-malonamide a) 7-Amino-5-(2,2,2-trifluoro-ethyl)-5H,7H-dibenzo[b,d]azepin-6-one Racemic (RS)-7-amino-5-(2,2,2-trifluoro-ethyl)-5H,7H-dibenzo[b,d]azepin-6-one was separated by chromatography on Chiralpak AD with isopopanol/heptane 1:3 as solvent to yield
(S)-7-amino-5-(2,2,2-trifluoro-ethyl)-5H,7H-dibenzo[b,d]azepin-6-one [α] 589=−29° (1% in CHCl$_3$) and
(R)-7-amino-5-(2,2,2-trifluoro-ethyl)-5H,7H-dibenzo[b,d]azepin-6-one. [α] 589=+260 (1% in CHCl$_3$).

b) (S)-2,2-Dimethyl-N-[(S)-6-oxo-5-(2,2,2-trifluoro-ethyl)-6,7-dihydro-5H-dibenzo[b,d]azepin-7-yl]-N'-(2,2,3,3,3-pentafluoro-propyl)-malonamide (S)-7-amino-5-(2,2,2-trifluoro-ethyl)-5H,7H-dibenzo[b,d]azepin-6-one was coupled with 2,2-dimethyl-N-(3,3,4,4,4-pentafluoro-butyl)-malonamic acid in analogy to the description example 73 to yield (S)-2,2-dimethyl-N-[(S)-6-oxo-5-(2,2,2-trifluoro-ethyl)-6,7-dihydro-5H-dibenzo[b,d]azepin-7-yl]-N'-(2,2,3,3,3-pentafluoro-propyl)-malonamide as white solid,

[α] 589=13.9° (1.1% in CHCl$_3$), MS m/e (%): 550.5 (M–H$^+$, 100).

EXAMPLE 90

(2RS)-2-Fluoro-2-methyl-N-[(S)-5-methyl-6-oxo-6,7-dihydro-5H-dibenzo[b,d]azepin-7-yl]-N'-(3,3,4,4,4-pentafluoro-butyl)-malonamide In an analogous manner to that described in Example 20 d), the condensation of (S)-7-amino-5-methyl-5H,7H-dibenzo[b,d]azepin-6-one and (2RS)-2-fluoro-2-methyl-N-(3,3,4,4,4-pentafluoro-butyl)-malonamic acid yielded the title compound as a white solid;
MS: m/e=502 (M+H)$^+$.
The (2RS)-2-fluoro-2-methyl-N-(3,3,4,4,4-pentafluoro-butyl)-malonamic acid was obtained in a reaction sequence analogous to that leading to (2RS)-methyl-N-(2,2,2-trifluoro-ethyl)-malonamic acid [Example 20 c)] by replacing (2RS)-methyl-malonic acid monoester by (2RS)-2-fluoro-2-methyl-malonic acid monoester and by replacing 2,2,2-trifluoro-ethylamine by 3,3,4,4,4-pentafluoro-butylamine [J.Fluorine Chemistry 55(1), 85 (1991)].

EXAMPLES 91 AND 92

(2R)-2-Fluoro-2-methyl-N-[(S)-5-methyl-6-oxo-6,7-dihydro-5H-dibenzo[b,d]azepin-7-yl]-N'-(3,3,4,4,4-pentafluoro-butyl)-malonamide and (2S)-2-Fluoro-2-methyl-N-[(S)-5-methyl-6-oxo-6,7-dihydro-5H-dibenzo[b,d]azepin-7-yl]-N'-(3,3,4,4,4-pentafluoro-butyl)-malonamide The separation of 0.2 g of the two isomers of (2RS)-2-fluoro-2-methyl-N-[(S)-5-methyl-6-oxo-6,7-dihydro-5H-dibenzo[b,d]azepin-7-yl]-N'-(3,3,4,4,4-pentafluoro-butyl)-malonamide (Example WG) was performed on a preparative chiral HPLC column (CHIRALPAK® AD, pressure: flow: 35 ml/min) using a 4:1 mixture of n-heptane and isopropanol as the eluent. There were obtained 23 mg [11% of theory, optical integrity >99.5% d.e., MS: m/e=502 (M+H)+] of the first eluting isomer (2R)-2-Fluoro-2-methyl-N-[(S)-5-methyl-6-oxo-6,7-dihydro-5H-dibenzo[b,d]azepin-7-yl]-N'-(3,3,4,4,4-pentafluoro-butyl)-malonamide and 22 mg [11% of theory, optical integrity >99.5% d.e., MS: m/e=502 (M+H)$^+$] of the later eluting isomer (2S)-2-fluoro-2-methyl-N-[(S)-5-methyl-6-oxo-6,7-dihydro-5H-dibenzo[b,d]azepin-7-yl]-N'-(3,3,4,4,4-pentafluoro-butyl)-malonamide, each as a yellowish foam.

EXAMPLE 93

(2RS)-2-Methyl-N-[(S)-5-methyl-6-oxo-6,7-dihydro-5H-dibenzo[b,d]azepin-7-yl]-N'-(3,3,4,4,4-pentafluoro-butyl)-malonamide In an analogous manner to that described in Example 20 d), the condensation of (S)-7-amino-5-methyl-5H,7H-dibenzo[b,d]azepin-6-one and (2RS)-2-methyl-N-(3,3,4,4,4-pentafluoro-butyl)-malonamic acid yielded the title compound as a white solid;
MS: m/e=484 (M+H)$^+$.
The (2RS)-2-methyl-N-(3,3,4,4,4-pentafluoro-butyl)-malonamic acid was obtained in a reaction sequence analogous to that leading to (2RS)-methyl-N-(2,2,2-trifluoro-ethyl)-malonamic acid [Example 20 c)] by replacing 2,2,2-trifluoro-ethylamine by 3,3,4,4,4-pentafluoro-butylamine [J.Fluorine Chemistry 55(1), 85 (1991)].

EXAMPLE 94

2,2-Dimethyl-N-[(S5-methyl-6-oxo-6,7-dihydro-5H-dibenzo[b,d]azepin-7-yl]-N'-(3,3,4,4,4-pentafluoro-butyl)-malonamide In an analogous manner to that described in Example 20 d), the condensation of (S)-7-amino-5-methyl-5H,7H-dibenzo[b,d]azepin-6-one and 2,2-dimethyl-N-(3,3,4,4,4-pentafluoro-butyl)-malonamic acid yielded the title compound as a white solid;
MS: m/e=498 (M+H)$^+$.
The 2,2-dimethyl-N-(3,3,4,4,4-pentafluoro-butyl)-malonamic acid was obtained in a reaction sequence analogous to that leading to (2RS)-methyl-N-(2,2,2-trifluoro-ethyl)-malonamic acid [Example 20 c)] by replacing (2RS)-methyl-malonic acid monoester by 2,2-dimethyl-malonic acid monoester and by replacing 2,2,2-trifluoro-ethylamine by 3,3,4,4,4-pentafluoro-butylamine.

EXAMPLE 95

(2RS)-Methyl-N-((3S)-1-methyl-2-oxo-5-trifluoromethanesulfonyl-2,3,4,5-tetrahydro-1H-benzo[b][1,4]diazepin-3-yl)-N'-(2,2,3,3,3-pentafluoro-propyl)-malonamide In an analogous manner to that described in Example 26, the reaction of (2RS)-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide [Example 25] with trifluoromethanesulfonic acid anhydride yielded the title compound as a white foam;
MS: m/e=555 (M+H)$^+$.

EXAMPLE 96

N-((3S)-5-Formyl-1-methyl-2-oxo-2,3,4,5-tetrahydro-1H-benzo[b][1,4]diazepin-3-yl)-(2RS)-methyl-N'-(2,2,3,3,3-pentafluoro-propyl)-malonamide In an analogous manner to that described in Example 26, the acylation of (2RS)-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide with acetic acid anhydride and formic acid yielded the title compound as a light yellow foam; MS: m/e=451 (M+H)$^+$.

EXAMPLE 97

N-[(3S)-5-(2-Fluoro-acetyl)-1-methyl-2-oxo-2,3,4,5-tetrahydro-1H-benzo[b][1,4]diazepin-3-yl]-(2RS)-methyl-N'-(2,2,3,3,3-pentafluoro-propyl)-malonamide In an analogous manner to that described in Example 26, the acylation of (2RS)-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide with fluoroacetyl chloride yielded the title compound as a light yellow foam;
MS: m/e=483 (M+H)$^+$.

EXAMPLE 98

(2RS)-Methyl-N-[(3S)-1-methyl-2-oxo-5-(2,2,2-trifluoro-acetyl)-2,3,4,5-tetrahydro-1H-benzo[b][1,4]diazepin-3-yl]-N'-(2,2,3,3,3-pentafluoro-propyl)-malonamide In an analogous manner to that described in Example 26, the acylation of (2RS)-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide with trifluoroacetic anhydride yielded the title compound as a white foam; MS: m/e=519 (M+H)$^+$.

EXAMPLE 99

N-[(3S)-5-(2-Methoxy-acetyl)-1-methyl-2-oxo-2,3,4,5-tetrahydro-1H-benzo[b][1,4]diazepin-3-yl]-(2RS)-methyl-N'-(2,2,3,3,3-pentafluoro-propyl)-malonamide In an analogous manner to that described in Example 26, the acylation of (2RS)-methyl-N-((3S)-1-methyl-2-oxo-2,3,4,5-tetrahydro-1H-benzo[b][1,4]diazepin-3-yl)-N'-(2,2,3,3,3-pentafluoro-propyl)-malonamide with methoxyacetyl chloride yielded the title compound as a light yellow foam; MS: m/e=495 (M+H)$^+$.

EXAMPLE 100

N-[(S)-5-Methanesulfonyl-2-oxo-1-(2,2,2-trifluoro-ethyl)-2,3,4,5-tetrahydro-1H-benzo[b][1,4]diazepin-3-yl]-(2RS)-methyl-N'-(2,2,3,3,3-pentafluoro-propyl)-malonamide a) (S)-3-Amino-1-(2,2,2-trifluoro-ethyl)-1,3,4,5-tetrahydro-benzo[b][1,4]diazepin-2-one Hydrochloride In an analogous manner to that described in Example 25 a), the alkylatiion of (S)-(2-oxo-2,3,4,5-tetrahydro-1H-benzo[b][1,4]diazepin-3-yl)-carbamic acid tert-butyl ester by 2,2,2-trifluoroethyl triflate followed by the acid catalysed cleavage of the tert-butoxycarbonyl group yielded the title compound as a yellow solid.

b) (2RS)-Methyl-N-[(S)-2-oxo-1-(2,2,2-trifluoro-ethyl)-2,3,4,5-tetrahydro-1H-benzo[b][1,4]diazepin-3-yl]-N'-(2,2,3,3,3:pentafluoro-propyl)-malonamide In an analogous manner to that described in Example 20 d), the condensation of (S)-3-amino-1-(2,2,2-trifluoro-ethyl)-1,3,4,5-tetrahydro-benzo[b][1,4]diazepin-2-one hydrochloride and (2RS)-methyl-N-(2,2,3,3,3-pentafluoro-propyl)-malonamic acid [see Example 25 b)] yielded the title compound as a white foam;
MS: m/e=491 (M+H)$^+$.

c) N-[(S)-5-Methanesulfonyl-2-oxo-1-(2,2,2-trifluoro-ethyl)-2,3,4,5-tetrahydro-1H-benzo[b][1,4]diazepin-3-yl]-(2RS)-methyl-N'-(2,2,3,3,3-pentafluoro-propyl)-malonamide In an analogous manner to that described in Example 26, the reaction of (2RS)-methyl-N-[(S)-2-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide with methanesullfonic acid anhydride yielded the title compound as an off-white amorphous material;
MS: m/e=567 (M−H)$^−$.

EXAMPLE 101

(2RS)-Methyl-N-[(S)-2-oxo-1-(2,2,2-trifluoro-ethyl)-5-trifluoromethanesulfonyl-2,3,4,5-tetrahydro-1H-benzo[b][1,4] diazepin-3-yl]-N'-(2,2,3,3,3-pentafluoro-propyl)-malonamide In an analogous manner to that described in Example 26, the reaction of (2RS)-methyl-N-[(S)-2-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide with trifluoromethanesulfonic acid anhydride yielded the title compound as an white amorphous material;
MS: m/e=623 (M+H)$^+$.

EXAMPLE 102

(2RS)-Methyl-N-[(S)-2-oxo-5-(2,2,2-trifluoro-acetyl)-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide In an analogous manner to that described in Example 26, the reaction of (2RS)-methyl-N-[(S)-2-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide with trifluoroacetic acid anhydride yielded the title compound as a light yellow solid;
MS: m/e=587 (M+H)$^+$.

EXAMPLE 103

(S)-N-(5-Methanesulfonyl-1-methyl-2-oxo-2,3,4,5-tetrahydro-1H-benzo[b][1,4]diazepin-3-yl)-(2RS)-methyl-N'-(2,2,3,3,3-pentafluoro-propyl)-malonamide a) (S)-(1-Methyl-2-oxo-2,3,4,5-tetrahydro-1H-benzo[b][1,4]diazepin-3-yl)-carbamic acid tert-butyl ester The alkylation of the (S)-(2-oxo-2,3,4,5-tetrahydro-1H-benzo[b][1,4] diazepin-3-yl)-carbamic acid tert-butyl ester with methyliodide, as described in Example 25 a), yielded, after chromatography on silica gel using a 3:1-mixture of n-heptane and ethyl acetate as the eluent, the (S)-(1-methyl-2-oxo-2,3,4,5-tetrahydro-1H-benzo[b][1,4]diazepin-3-yl)-carbamic acid tert-butyl ester as a light yellow foam;
MS: m/e=292 (M+H)$^+$.

b) [(S)-5-Methanesulfonyl-1-methyl-2-oxo-2,3,4,5-tetrahydro-1H-benzo[b][1,4]diazepin-3-yl]-carbamic acid tert-butyl ester A mixture of 623 mg (3.4 mmol) of methanesulfonic acid anhydride and 0.12 ml (0.7 mmol) of N-ethyl-diisopropylamine was cooled to 0° C. and treated with a solution of 200 mg (0.7 mmol) of (S)-(1-methyl-2-oxo-2,3,4,5-tetrahydro-1H-benzo[b][1,4]diazepin-3-yl)-carbamic acid tert-butyl ester in 2 ml of dichloromethane. The reaction mixture was left to warm to room temperature and stirred during 18 h. For the working-up, the reaction mixture was cooled to 0° C. and treated with a saturated solution of sodium carbonate. The organic layer was separated, washed with a saturated solution of ammonium hydrochloride and water, finally dried over sodium sulphate and evaporated. For purification, the crude material was chromatographed on silical gel using a 96:4-mixture of dichloromethane and ethyl acetate as the eluent. There were obtained 100 mg (40% of theory) of the ((S)-5-methanesulfonyl-1-methyl-2-oxo-2,3,4,5-tetrahydro-1H-benzo[b][1,4]diazepin-3-yl)-carbamic acid tert-butyl ester as a white foam;
MS: m/e=370 (M+H)+.

c) (S)-3-Amino-5-methanesulfonyl-1-methyl-1,3,4,5-tetrahydro-benzo[b][1,4]diazepin-2-one hydrochloride A solution of 100 mg (0.27 mmol) of ((S)-5-methanesulfonyl-1-methyl-2-oxo-2,3,4,5-tetrahydro-1H-benzo[b][1,4]diazepin-3-yl)-carbamic acid tert-butyl ester in 5 ml of dioxane was treated with 0.22 ml of hydrochloric acid and heated in the sealed flask at 50° C. for 1 hour. For the working-up, the solvent was evaporated under reduced pressure and the residue submitted to a azeotropic distillation with toluene. After drying under reduced pressure, the (S)-3-amino-5-methanesulfonyl-1-methyl-1,3,4,5-tetrahydro-benzo[b][1,4]diazepin-2-one hydrochloride was obtained in quantitative yield as a light yellow solid; MS: m/e=270 (M+H)+.

d) (S)-N-(5-methanesulfonyl-1-methyl-2-oxo-2,3,4,5-tetrahydro-1H-benzo[b][1,4]diazepin-3-yl)-(2RS)-methyl-N'-(2,2,3,3-pentafluoro-propyl)-malonamide In an analogous manner to that described in Example 20 d), the condensation of (S)-3-amino-5-methanesulfonyl-1-methyl-1,3,4,5-tetrahydro-benzo[b][1,4]diazepin-2-one hydrochloride and (2RS)-methyl-N-(2,2,3,3-pentafluoro-propyl)-malonamic acid [see Example 25 b)] yielded the title compound as a white foam;
MS: m/e=501 (M+H)+.

EXAMPLE 104

N-[(S)-5-(2,2-Dimethyl-propionyl)-1-methyl-2-oxo-2,3,4,5-tetrahydro-1H-benzo[b][1,4]diazepin-3-yl]-N'-(2,2,3,3-pentafluoro-propyl)-malonamide a) [(3S)-5-(2,2-Dimethyl-propionyl)-1-methyl-2-oxo-2,3,4,5-tetrahydro-1H-benzo[b][1,4]diazepin-3-yl]-carbamic acid tert-butyl ester In an analogous manner to that described in Example 103b), the acylation of (S)-(1-methyl-2-oxo-2,3,4,5-tetrahydro-1H-benzo[b][1,4]diazepin-3-yl)-carbamic acid tert-butyl ester with pivaloyl chloride yielded the title compound as a white solid; MS: m/e=376 (M+H)+.

b) (S)-3-Amino-5-(2,2-dimethyl-propionyl)-1-methyl-1,3,4,5-tetrahydro-benzo[b][1,4]diazepin-2-one Hydrochloride In an analogous manner to that described in Example 103c), the cleavage of the tert-butoxy-carbonyl group of the [(3S)-5-(2,2-dimethyl-propionyl)-1-methyl-2-oxo-2,3,4,5-tetrahydro-1H-benzo[b][1,4]diazepin-3-yl]-carbamic acid tert-butyl ester yielded the title compound as a white solid;
MS: m/e=276 (M+H)+.

c) N-[(S)-5-(2,2-Dimethyl-propionyl)-1-methyl-2-oxo-2,3,4,5-tetrahydro-1H-benzo[b][1,4]diazepin-3-yl]-N'-(2,2,3,3-3-pentafluoro-propyl)-malonamide In an analogous manner to that described in Example 20 d), the condensation of (S)-3-amino-5-(2,2-dimethyl-propionyl)-1-methyl-1,3,4,5-tetrahydro-benzo[b][1,4]diazepin-2-one hydrochloride and N-(2,2,3,3,3-pentafluoro-propyl)-malonamic acid yielded the title compound as a white foam;
MS: m/e=493 (M+H)+.

The N-(2,2,3,3,3-pentafluoro-propyl)-malonamic acid was obtained in a reaction sequence analogous to that leading to (2RS)-methyl-N-(2,2,2-trifluoro-ethyl)-malonamic acid [Example 20 c)] by replacing (2RS)-methylmalonic acid monoester by malonic acid monoester.

EXAMPLE 105

N-[(3S)-5-(2,2-Dimethyl-propionyl)-1-methyl-2-oxo-2,3,4,5-tetrahydro-1H-benzo[b][1,4]diazepin-3-yl]-(2RS)-methyl-N'-(2,2,3,3,3-pentafluoro-propyl)-malonamide In an analogous manner to that described in Example 20 d), the condensation of (S)-3-amino-5-(2,2-dimethyl-propionyl)-1-methyl-1,3,4,5-tetrahydro-benzo[b][1,4]diazepin-2-one hydrochloride and (2RS)-methyl-N-(2,2,2-trifluoro-ethyl)-malonamic acid [Example 20 c)] yielded the title compound as a white foam; MS: m/e=507 (M+H)+.

EXAMPLE 106

5-Methyl-4-oxo-(3S)-[(2RS)-(2,2,3,3,3-pentafluoro-propylcarbamoyl)-propionylamino]-2,3,4,5-tetrahydro-benzo[b][1,4]diazepine-1-carboxylic acid cyclopropylmethyl estermalonamide a) (S)-3-tert-Butoxycarbonylamino-5-methyl-4-oxo-2,3,4,5-tetrahydro-benzo[b][1,4]diazepine-1-carboxylic Acid Cyclopropylmethyl Ester A solution of 350 mg (1.2 mmol) of (S)-(1-methyl-2-oxo-2,3,4,5-tetrahydro-1H-benzo[b][1,4]diazepin-3-yl)-carbamic acid tert-butyl ester [Example 103a] in 10 ml of N,N-dimethylformamide was treated successively with about 1 g of solid carbon dioxide, 237 mg (1.7 mmol) of bromomethyl-cyclopropane, and 626 mg (1.9 mmol) of cesium carbonate. The reaction mixture was stirred in a sealed flask at 80° C. during the weekend. For the working-up, the solvent was evaporated under reduced pressure and the residue was dissolved in a mixture of 30 ml of ethyl acetate and 10 ml of water. The organic layer was separated, dried over sodium sulphate and evaporated under reduced pressure. For the purification, the crude compound was chromatographed on silica gel using a 3:1-mixture of heptane and ethyl acetate as the eluent. There were obtained 410 mg (87% of theory) of the (S)-3-tert-butoxycarbonylamino-5-methyl-4-oxo-2,3,4,5-tetrahydro-benzo[b][1,4]diazepine-1-carboxylic acid cyclopropylmethyl ester as a white gum; MS: m/e=579 (M+OAc)+.

b) (S)-3-Amino-5-methyl-4-oxo-2,3,4,5-tetrahydro-benzo[b][1,4]diazepine-1-carboxylic acid cyclopropylmethyl ester hydrochloride In an analogous manner to that described in Example 103c), the cleavage of the tert-butoxy-carbonyl group of the (S)-3-tert-butoxycarbonylamino-5-methyl-4-oxo-2,3,4,5-tetrahydro-benzo[b][1,4]diazepine-1-carboxylic acid cyclopropylmethyl ester yielded the title compound as a light yellow foam.

c) 5-Methyl-4-oxo-(3S)-[(2RS)-(2,2,3,3,3-pentafluoropropylcarbamoyl)-propionylamino]-2,3,4,5-tetrahydro-benzo[b][1,4]diazepine-1-carboxylic acid cyclopropylmethyl estermalonamide In an analogous manner to that described in Example 20 d), the condensation of (S)-3-amino-5-methyl-4-oxo-2,3,4,5-tetrahydro-benzo[b][1,4]diazepine-1-carboxylic acid cyclopropylmethyl ester hydrochloride and (2RS)-methyl-N-(2,2,2-trifluoro-ethyl)-malonamic acid [Example 20 c)] yielded the title compound as a white solid; MS: m/e=579 (M+OAc)+.

EXAMPLE 107

N-[(S)-5-Acetyl-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide a) [(S)-2-Oxo-1-(2,2,2-trifluoro-ethyl)-2,3,4,5-tetrahydro-1H-benzo[b][1,4]diazepin-3-yl]-carbamic acid tert-butyl ester In an analogous manner to that described in Example 25 a), the alkylation of the (S)-(2-oxo-2,3,4,5-tetrahydro-1H-benzo[b][1,4] diazepin-3-yl)-carbamic acid tert-butyl ester with 2,2,2-trifluoroethyl triflate, yielded, after chromatography on silica gel using a 98:2-mixture of dichloromethane and methanol as the eluent, the title compound as a white solid;

MS: m/e=360 (M+H)+.

b) [(S)-5-Acetyl-2-oxo-1-(2,2,2-trifluoro-ethyl)-2,3,4,5-tetrahydro-1H-benzo[b][1,4]diazepin-3-yl]-carbamic acid tert-butyl ester In an analogous manner to that described in Example 103b, the acylation of the [(S)-2-oxo-1-(2,2,2-trifluoro-ethyl)-2,3,4,5-tetrahydro-1H-benzo[b][1,4]diazepin-3-yl]-carbamic acid tert-butyl ester with acetic acid anhydride yielded the title compound as a white solid;

MS: m/e=419 (M+NH4)+.

c) (S)-5-Acetyl-3-amino-1-(2,2,2-trifluoro-ethyl)-1,3,4,5-tetrahydro-benzo[b][1,4]diazepin-2-one Hydrochloride In an analogous manner to that described in Example 103c, the cleavage of the tert-butoxycarbonyl group of the [(S)-5-acetyl-2-oxo-1-(2,2,2-trifluoro-ethyl)-2,3,4,5-tetrahydro-1H-benzo[b][1,4]diazepin-3-yl]-carbamic acid tert-butyl ester by hydrochloric acid yielded the title compound as a light yellow solid;

MS: m/e=302 (M+H)+.

d) N-[(S)-5-Acetyl-2-oxo-1-(2,2,2-trifluoro-ethyl)-2,3,4,5-tetrahydro-1H-benzo[b][1,4]diazepin-3-yl]-(2RS)-methyl-N'-(2,2,3,3,3:pentafluoro-propyl)-malonamide In an analogous manner to that described in Example 20 d), the condensation of (S)-5-acetyl-3-amino-1-(2,2,2-trifluoro-ethyl)-1,3,4,5-tetrahydro-benzo[b][1,4]diazepin-2-one hydrochloride and (2RS)-methyl-N-(2,2,3,3,3-pentafluoro-propyl)-malonamic acid [see Example 25 b)] yielded the title compound as a white solid; MS: m/e=533 (M+H)+.

EXAMPLE 108

N-[(S)-5-Cyclopropanecarbonyl-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide a) [(S)-5-Cyclopropanecarbonyl-2-oxo-1-(2,2,2-trifluoro-ethyl)-2,3,4,5-tetrahydro-1H-benzo[b][1,4]diazepin-3-yl]-carbamic acid tert-butyl ester In an analogous manner to that described in Example 103b, the acylation of the [(S)-2-oxo-1-(2,2,2-trifluoro-ethyl)-2,3,4,5-tetrahydro-1H-benzo[b][1,4]diazepin-3-yl]-carbamic acid tert-butyl ester [Example 107b] with cyclopropane-carbonyl chloride yielded the title compound as a yellow solid; MS: m/e=428 (M+H)+.

b) (S)-3-Amino-5-cyclopropanecarbonyl-1-(2,2,2-trifluoro-ethyl)-1,3,4,5-tetrahydro-benzo[b][1,4]diazepin-2-one hydrochloride In an analogous manner to that described in Example 103c, the cleavage of the tert-butoxycarbonyl group of the [(S)-5-cyclopropanecarbonyl-2-oxo-1-(2,2,2-trifluoro-ethyl)-2,3,4,5-tetrahydro-1H-benzo[b][1,4]diazepin-3-yl]-carbamic acid tert-butyl ester by hydrochloric acid yielded the title compound as a yellow solid; MS: m/e=328 (M+H)+.

c) N-[(S)-5-Cyclopropanecarbonyl-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide In an analogous manner to that described in Example 20 d), the condensation of (S)-5-acetyl-3-amino-1-(2,2,2-trifluoro-ethyl)-1,3,4,5-tetrahydro-benzo[b][1,4]diazepin-2-one hydrochloride and (2RS)-methyl-N-(2,2,3,3,3-pentafluoro-propyl)-malonamic acid [see Example 25 b)] yielded the title compound as a white solid;

MS: m/e=559 (M+H)+.

EXAMPLE 109

4-Oxo-(3S)-[(2RS)-(2,2,3,3,3-pentafluoro-propylcarbamoyl)-propionylamino]-5-(2,2,2-trifluoro-ethyl)-2,3,4,5-tetrahydro-benzo[b][1,4]diazepine-1-carboxylic Acid Cyclopropylmethyl Ester a) (S)-3-tert-Butoxycarbonylamino-4-oxo-5-(2,2,2-trifluoro-ethyl)-2,3,4,5-tetrahydro-benzo[b][1,4]diazepine-1-carboxylic acid cyclopropylmethyl ester In an analogous manner to that described in Example 106a, the reaction of [(S)-2-oxo-1-(2,2,2-trifluoro-ethyl)-2,3,4,5-tetrahydro-1H-benzo[b][1,4]diazepin-3-yl]-carbamic acid tert-butyl ester [Example 107b] with carbon dioxide and bromomethyl-cyclopropane in presence of cesium carbonate yielded the title compound as a white foam; MS: m/e=475 (M+NH4)+.

b) (S)-3-Amino-4-oxo-5-(2,2,2-trifluoro-ethyl)-2,3,4,5-tetrahydro-benzo[b][1,4]diazepine-1-carboxylic acid cyclopropylmethyl ester hydrochloride In an analogous manner to that described in Example 103c, the cleavage of the tert-butoxycarbonyl group of the (S)-3-tert-butoxycarbonylamino-4-oxo-5-(2,2,2-trifluoro-ethyl)-2,3,4,5-tetrahydro-benzo[b][1,4]diazepine-1-carboxylic acid cyclopropylmethyl ester by hydrochloric acid yielded the title compound as a yellowish foam which was engaged in the next step without further purification and characterisation.

c) 4-Oxo-(3S)-[(2RS)-(2,2,3,3,3-pentafluoro-propylcarbamoyl)-propionylamino]-5-(2,2,2-trifluoro-ethyl)-2,3,4,5-tetrahydro-benzo[b][1,4]diazepine-1-carboxylic acid cyclopropylmethyl ester In an analogous manner to that described in Example 20 d), the condensation of the (S)-3-Amino-4-oxo-5-(2,2,2-trifluoro-ethyl)-2,3,4,5-tetrahydro-benzo[b][1,4]diazepine-1-carboxylic acid cyclopropylmethyl ester hydrochloride and (2RS)-methyl-N-(2,2,3,3,3-pentafluoro-propyl)-malonamic acid [see Example 25 b)] yielded the title compound as a light yellow solid; MS: m/e=647 (M+OAc)+.

EXAMPLE 110

(2RS)-N-[(S)-5-Acetyl-1-methyl-2-oxo-2,3,4,5-tetrahydro-1H-benzo[b][1,4]diazepin-3-yl]-2-fluoro-2-methyl-N'-(2,2,3,3,3-pentafluoro-propyl)-malonamide a) [(S)-5-Acetyl-1-methyl-2-oxo-2,3,4,5-tetrahydro-1H-benzo[b][1,4]diazepin-3-yl]carbamic acid tert-butyl ester In an analogous manner to that described in Example 103b, the acylation of (S)-(1-methyl-2-oxo-2,3,4,5-tetrahydro-1H-benzo[b][1,4]diazepin-3-yl)-carbamic acid tert-butyl ester [Example 103a] with acetic acid anhydride yielded the title compound as a white solid;

MS: m/e=334 (M+H)$^+$.

b) (S)-5-Acetyl-3-amino-1-methyl-1,3,4,5-tetrahydro-benzo[b][1,4]diazepin-2-one hydrochloride In an analogous manner to that described in Example 103c, the cleavage of the tert-butoxy-carbonyl group of the [(S)-5-acetyl-1-methyl-2-oxo-2,3,4,5-tetrahydro-1H-benzo[b][1,4]diazepin-3-yl]-carbamic acid tert-butyl ester yielded the title compound as a light yellow solid;

MS: m/e=234 (M+H)$^+$.

c) (2RS)-N-[(S)-5-Acetyl-1-methyl-2-oxo-2,3,4,5-tetrahydro-1H-benzo[b][1,4]diazepin-3-yl]-2-fluoro-2-methyl-N'-(2,2,3,3,3-pentafluoro-propyl)-malonamide In an analogous manner to that described in Example 20 d), the condensation of (S)-5-acetyl-3-amino-1-methyl-1,3,4,5-tetrahydro-benzo[b][1,4]diazepin-2-one hydrochloride and 2-fluoro-2-methyl-N-(2,2,3,3,3-pentafluoro-propyl)-malonamic acid yielded the title compound as a white foam;

MS: m/e=483 (M+H)$^+$.

The (2RS)-2-fluoro-2-methyl-N-(2,2,3,3,3-pentafluoro-propyl)-malonamic acid was obtained in a reaction sequence analogous to that leading to (2RS)-methyl-N-(2,2,2-trifluoro-ethyl)-malonamic acid [Example 20 c)] by replacing (2RS)-methyl-malonic acid monoester by (2RS)-2-fluoro-2-methyl-malonic acid monoester.

EXAMPLE 111

N-[(S)-5-Acetyl-1-ethyl-2-oxo-2,3,4,5-tetrahydro-1H-benzo[b][1,4]diazepin-3-yl]-2,2-dimethyl-N'-(2,2,3,3,3-pentafluoro-propyl)-malonamide a) (S)-1-Acetyl-4-oxo-2,3,4,5-tetrahydro-1H-benzo[b][1,4]diazepin-3-yl)-carbamic acid tert-butyl ester In an analogous manner to that described in Example 52 a), the acetylattion of (S)-(2-oxo-2,3,4,5-tetrahydro-1H-benzo[b][1,4] diazepin-3-yl)-carbamic acid tert-butyl ester with acetic acid anhydride yielded the title compound as a grey solid; MS: m/e=320 (M+H)$^+$.

b) (S)-5-Acetyl-3-amino-1-ethyl-1,3,4,5-tetrahydro-benzo[b][1,4]diazepin-2-one

In an analogous manner to that described in Example 25 a), the alkylation of the (S)-1-acetyl-4-oxo-2,3,4,5-tetrahydro-1H-benzo[b][1,4]diazepin-3-yl)-carbamic acid tert-butyl ester with ethyl iodide, followed by the acid catalysed cleavage of the tert-butoxycarbonyl group yielded the title compound as a yellowish waxy solid [MS: m/e=248 (M+H)$^+$] which was engaged in the next step without further purification.

c) N-[(S)-5-Acetyl-1-ethyl-2-oxo-2,3,4,5-tetrahydro-1H-benzo[b][1,4]diazepin-3-yl]-2,2-dimethyl-N'-(2,2,3,3,3-pentafluoro-propyl)-malonamide In an analogous manner to that described in Example 20 d) and 27, the condensation of (S)-5-acetyl-3-amino-1-ethyl-1,3,4,5-tetrahydro-benzo[b][1,4]diazepin-2-one and 2,2-dimethyl-N-(2,2,3,3,3-pentafluoro-propyl)-malonamic acid yielded the title compound as a white solid; MS: m/e=493 (M+H)$^+$.

EXAMPLE 112

N-((S)-5-Acetyl-1-ethyl-2-oxo-2,3,4,5-tetrahydro-1H-benzo[b][1,4]diazepin-3-yl)-(2RS)-methyl-N'-(2,2,3,3,3-pentafluoro-propyl)-malonamide In an analogous manner to that described in Example 20 d) and 27, the condensation of (S)-5-acetyl-3-amino-1-ethyl-1,3,4,5-tetrahydro-benzo[b][1,4]diazepin-2-one and (2RS)-methyl-N-(2,2,3,3,3-pentafluoro-propyl)-malonamic acid [see Example 25 b)] yielded the title compound as a white solid;

MS: m/e=479 (M+H)$^+$.

EXAMPLE 113

N-[(S)-5-Acetyl-1-isopropyl-2-oxo-2,3,4,5-tetrahydro-1H-benzo[b][1,4]diazepin-3-yl]-(2RS)-methyl-N'-(2,2,3,3,3-pentafluoro-propyl)-malonamide a) (S)-5-Acetyl-3-amino-1-isopropyl-1,3,4,5-tetrahydro-benzo[b][1,4]diazepin-2-one In an analogous manner to that described in Example 25 a), the alkylation of the (S)-1-acetyl-4-oxo-2,3,4,5-tetrahydro-1H-benzo[b][1,4]diazepin-3-yl)-carbamic acid tert-butyl ester with 2-iodo-propane, followed by the acid catalysed cleavage of the tert-butoxycarbonyl group yielded the title compound as a yellowish waxy solid [MS: m/e=262 (M+H)$^+$] which was engaged in the next step without further purification.

b) N-[(S)-5-Acetyl-1-isopropyl-2-oxo-2,3,4,5-tetrahydro-1H-benzo[b][1,4]diazepin-3-yl]-(2RS)-methyl-N'-(2,2,3,3,3-pentafluoro-propyl)-malonamide In an analogous manner to that described in Example 20 d) and 27, the condensation of (S)-5-acetyl-3-amino-1-isopropyl-1,3,4,5-tetrahydro-benzo[b][1,4]diazepin-2-one and (2RS)-methyl-N-(2,2,3,3,3-pentafluoro-propyl)-malonamic acid [see Example 25 b)] yielded the title compound as a white solid; MS: m/e=493 (M+H)$^+$.

EXAMPLE 114

N-[(S)-5-Acetyl-1-benzyl-2-oxo-2,3,4,5-tetrahydro-1H-benzo[b][1,4]diazepin-3-yl]-2,2-dimethyl-N'-(2,2,3,3,3-pentafluoro-propyl)-malonamide a) (S)-5-Acetyl-3-amino-1-benzyl-1,3,4,5-tetrahydro-benzo[b][1,4]diazepin-2-one In an analogous manner to that described in Example 25 a), the alkylation of the (S)-1-acetyl-4-oxo-2,3,4,5-tetrahydro-1H-benzo[b][1,4]diazepin-3-yl)-carbamic acid tert-butyl ester with benzylbromide, followed by the acid catalysed cleavage of the tert-butoxycarbonyl group yielded the title compound as a light yellow solid [MS: m/e=310 (M+H)$^+$] which was engaged in the next step without further purification.

b) N-[(S)-5-Acetyl-1-benzyl-2-oxo-2,3,4,5-tetrahydro-1H-benzo[b][1,4]diazepin-3-yl]-2,2-dimethyl-N'-(2,2,3,3,3-pentafluoro-propyl)-malonamide In an analogous manner to that described in Example 20 d) and 27, the condensation of (S)-5-acetyl-3-amino-1-benzyl-1,3,4,5-tetrahydro-benzo[b][1,4]diazepin-2-one and 2,2-dimethyl-N-(2,2,3,3,3-pentafluoro-propyl)-malonamic acid [see Example 25 b)] yielded the title compound as a white solid; MS: m/e=553 (M−H)⁻.

EXAMPLE 115

N-((S)-5-Acetyl-1-benzyl-2-oxo-2,3,4,5-tetrahydro-1H-benzo[b][1,4]diazepin-3-yl)-(2RS)-methyl-N'-(2,2,3,3,3-pentafluoro-propyl)-malonamide In an analogous manner to that described in Example 20 d) and 27, the condensation of (S)-5-acetyl-3-amino-1-benzyl-1,3,4,5-tetrahydro-benzo[b][1,4]diazepin-2-one and (2RS)-methyl-N-(2,2,3,3,3-pentafluoro-propyl)-malonamic acid [see Example 25 b)] yielded the title compound as a white solid; MS: m/e=539 (M−H)⁻.

EXAMPLE 116

N-[(S)-5-Acetyl-1-(4-fluoro-benzyl-2-oxo-2,3,4,5-tetrahydro-1H-benzo[b][1,4]diazepin-3-yl]-2,2-dimethyl-N'-(2,2,3,3,3-pentafluoro-propyl)-malonamide a) (S)-5-Acetyl-3-amino-1-(4-fluoro-benzyl-1,3,4,5-tetrahydro-benzo[b][1,4]diazepin-2-one In an analogous manner to that described in Example 25 a), the alkylation of the (S)-1-acetyl-4-oxo-2,3,4,5-tetrahydro-1H-benzo[b][1,4]diazepin-3-yl)-carbamic acid tert-butyl ester with 4-fluoro-benzylbromide, followed by the acid catalysed cleavage of the tert-butoxycarbonyl group yielded the title compound as a white foam [MS: m/e=328 (M+H)⁺] which was engaged in the next step without further purification.

b) N-[(S)-5-Acetyl-1-(4-fluoro-benzyl-2-oxo-2,3,4,5-tetrahydro-1H-benzo[b][1,4]diazepin-3-yl]-2,2-dimethyl-N'-(2,2,3,3,3-pentafluoro-propyl)-malonamide In an analogous manner to that described in Example 20 d) and 27, the condensation of (S)-5-acetyl-3-amino-1-(4-fluoro-benzyl-1,3,4,5-tetrahydro-benzo[b][1,4]diazepin-2-one and 2,2-dimethyl-N-(2,2,3,3,3-pentafluoro-propyl)-malonamic acid [see Example 25 b)] yielded the title compound as a white solid;

MS: m/e=571 (M−H)⁻.

EXAMPLE 117

N-((S)-5-Acetyl-1-(4-fluoro-benzyl-2-oxo-2,3,4,5-tetrahydro-1H-benzo[b][1,4]diazepin-3-yl)-(2RS)-methyl-N'-(2,2,3,3,3-pentafluoro-propyl)-malonamide In an analogous manner to that described in Example 20 d) and 27, the condensation of (S)-5-acetyl-3-amino-1-(4-fluoro-benzyl-1,3,4,5-tetrahydro-benzo[b][1,4]diazepin-2-one and (2RS)-methyl-N-(2,2,3,3,3-pentafluoro-propyl)-malonamic acid [see Example 25 b)] yielded the title compound as a white solid;

MS: m/e=557 (M−H)⁻.

EXAMPLES 118 AND 119

N-[(S)-1-Acetyl-4-oxo-2,3,4,5-tetrahydro-1H-benzo[b][1,4]diazepin-3-yl]-(2R or 2S)-methyl-N'-(2,2,3,3,3-pentafluoro-propyl)-malonamide and N-[(S)-1-Acetyl-4-oxo-2,3,4,5-tetrahydro-1H-benzo[b][1,4]diazepin-3-yl]-(2S or 2R)-methyl-N'-(2,2,3,3,3-pentafluoro-propyl)-malonamide The separation of 0.2 g of the two isomers of N-[(S)-1-acetyl-4-oxo-2,3,4,5-tetrahydro-1H-benzo[b][1,4]diazepin-3-yl]-(2RS)-methyl-N'-(2,2,3,3,3-pentafluoro-propyl)-malonamide (Example 52) was performed on a preparative chiral HPLC column (CHIRALPAK® AD, pressure: 15 bar, flow: 35 ml/min) using a 4:1 mixture of n-heptane and isopropanol as the eluent. There were obtained 77 mg [35% of theory, optical integrity >99.5% d.e., MS: m/e=449 (M−H)-] of the first eluting isomer (+)-N-[(S)-1-acetyl-4-oxo-2,3,4,5-tetrahydro-1H-benzo[b][1,4]diazepin-3-yl]-(2R or 2S)-methyl-N'-(2,2,3,3,3-pentafluoro-propyl)-malonamide and 77 mg [35% of theory, optical integrity 99.4% d.e., MS: m/e=449 (M−H)⁻] of the later eluting isomer (−)-N-[(S)-1-acetyl-4-oxo-2,3,4,5-tetrahydro-1H-benzo[b][1,4]diazepin-3-yl]-(2S or 2R)-methyl-N'-(2,2,3,3,3-pentafluoro-propyl)-malonamide, each as a white solid.

EXAMPLES 120 AND 121

N-[(S)-5-Acetyl-1-methyl-2-oxo-2,3,4,5-tetrahydro-1H-benzo[b][1,4]diazepin-3-yl]-(2R or 2S)-methyl-N'-(2,2,3,3,3-pentafluoro-propyl)-malonamide and N-[(S)-5-Acetyl-1-methyl-2-oxo-2,3,4,5-tetrahydro-1H-benzo[b][1,4]diazepin-3-yl]-(2S or 2R)-methyl-N'-(2,2,3,3,3-pentafluoro-propyl)-malonamide The separation of 0.6 g of the two isomers of N-[(S)-5-acetyl-1-methyl-2-oxo-2,3,4,5-tetrahydro-1H-benzo[b][1,4]diazepin-3-yl]-(2RS)-methyl-N'-(2,2,3,3,3-pentafluoro-propyl)-malonamide (Example 40) was performed on a preparative chiral HPLC column (CHIRALPAK® AD, pressure: 15 bar, flow: 35 ml/min) using a 4:1 mixture of n-heptane and isopropanol as the eluent. There were obtained 220 mg (36.7% of theory, optical integrity >99.5% d.e.) of the first eluting isomer (+)-N-[(S)-5-acetyl-1-methyl-2-oxo-2,3,4,5-tetrahydro-1H-benzo[b][1,4]diazepin-3-yl]-(2R or 2S)-methyl-N'-(2,2,3,3,3-pentafluoro-propyl)-malonamide and 247 mg (41.2% of theory, optical integrity >99.5% d.e.) of the later eluting isomer (−)-N-[(S)-5-acetyl-1-methyl-2-oxo-2,3,4,5-tetrahydro-1H-benzo[b][1,4]diazepin-3-yl]-(2S or 2R)-methyl-N'-(2,2,3,3,3-pentafluoro-propyl)-malonamide, each as a white solid.

In analogy to the described examples the following compounds have been prepared:

EXAMPLE 122

2,2-Dimethyl-N-((S)-6-oxo-6,7-dihydro-5H-dibenzo[b,d]azepin-7-yl)-N'-(3,3,4,4,4-pentafluoro-butyl)-malonamide, MS: m/e (%)=484.5 (M+H)⁺, 100.

EXAMPLE 123

(R)-2-Fluoro-2-methyl-N-((S)-6-oxo-6,7-dihydro-5H-dibenzo[b,d]azepin-7-yl)-N'-(3,3,4,4,4-pentafluoro-butyl)-malonamide

EXAMPLE 124

(3,3,4,4,4-pentafluoro-butyl)-carbamic acid (S)-1-((S)-6-oxo-6,7-dihydro-5H-dibenzo[b,d]azepin-7-ylcarbamoyl)-ethyl ester MS: m/e (%)=488.5 (M+H)$^+$, 100.

EXAMPLE 125

(R)-2-Fluoro-2-methyl-N-((S)-5-methyl-6-oxo-6,7-dihydro-5H-dibenzo[b,d]azepin-7-yl)-N'-(3,3,3-trifluoro-propyl)-malonamide The title compound [MS m/e (%): 452.3 (M+H$^+$, 100)] was prepared in analogy to example 14 from 3,3,3-trifluoropropylamine and (2S)-2-fluoro-2-methyl-N-((S)-5-methyl-6-oxo-6,7-dihydro-5H-dibenzo[b,d]azepin-7-yl)-malonamic acid.

TABLE 2

| R$^1$ | R$^2$ | R$^3$ | R$^4$ | Example |
|---|---|---|---|---|
| 5-methyl-6-oxo-6,7-dihydro-5H-dibenzo[b,d]azepin-7-yl | CH$_2$-cyclopropyl | CH$_3$ | H | 1 |
| 5-methyl-6-oxo-6,7-dihydro-5H-dibenzo[b,d]azepin-7-yl | CH$_2$CH$_3$ | CH$_3$ | H | 2 |
| 5-methyl-6-oxo-6,7-dihydro-5H-dibenzo[b,d]azepin-7-yl | CH$_2$C≡CH | CH$_3$ | H | 3 |
| 5-methyl-6-oxo-6,7-dihydro-5H-dibenzo[b,d]azepin-7-yl | CH$_2$CH$_2$OCH$_3$ | CH$_3$ | H | 4 |
| 5-methyl-6-oxo-6,7-dihydro-5H-dibenzo[b,d]azepin-7-yl | n-butyl | CH$_3$ | H | 5 |

TABLE 2-continued
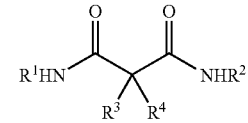
I
| R¹ | R² | R³ | R⁴ | Example |
|---|---|---|---|---|
| 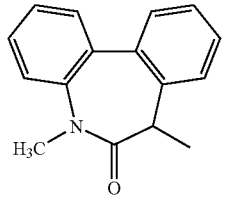 | 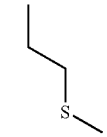 | CH₃ | H | 6 |
| 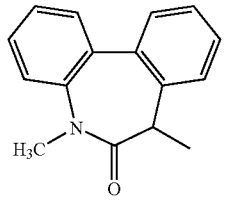 | 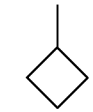 | CH₃ | H | 7 |
| 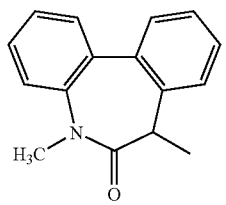 | 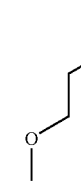 | CH₃ | H | 8 |
| 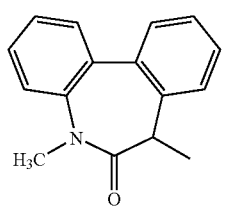 | 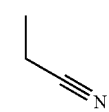 | CH₃ | H | 9 |
| 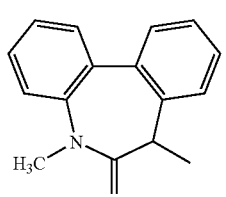 |  | CH₃ | H | 10 |
| 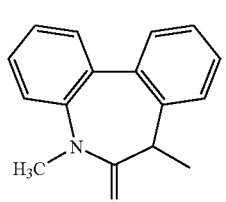 | 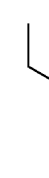 | CH₃ | H | 11 |

TABLE 2-continued
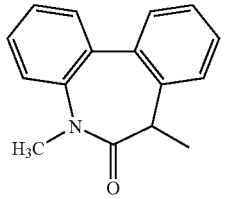
| R¹ | R² | R³ | R⁴ | Example |
|---|---|---|---|---|
| 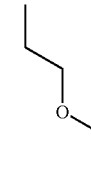 | 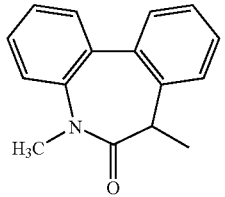 | CH₃ | H | 12 |
|  | 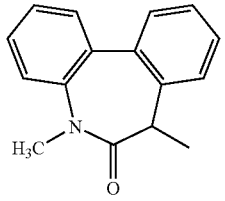 | CH₃ | H | 13 |
| 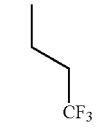 | 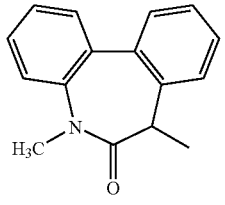 | CH₃ | H | 14 |
| 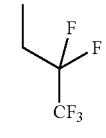 | 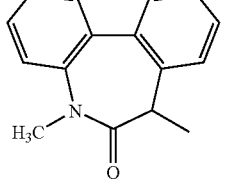 | CH₃ | H | 15 |
| 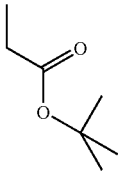 | 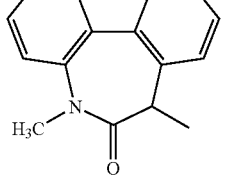 | CH₃ | H | 16 |
| 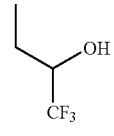 | | CH₃ | H | 17 |

TABLE 2-continued
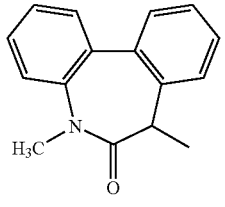
I
| R¹ | R² | R³ | R⁴ | Example |
|---|---|---|---|---|
| 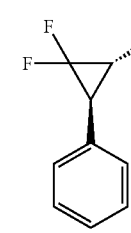 | 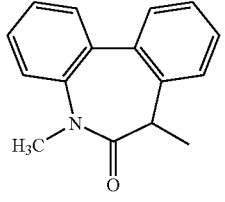 | CH₃ | H | 18 |
| 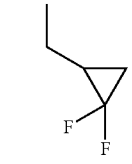 | 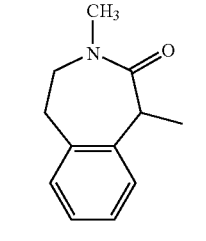 | CH₃ | H | 19 |
| 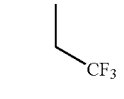 | 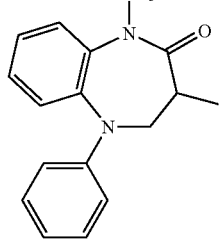 | CH₃ | H | 20 |
| 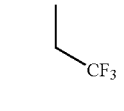 | 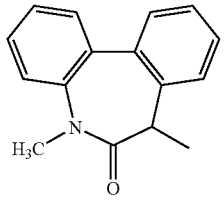 | CH₃ | H | 21 |
| 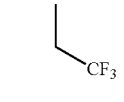 | 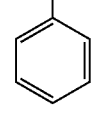 | 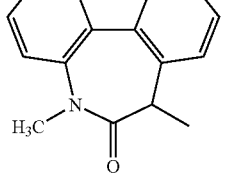 | H | 22 |
| 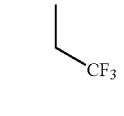 | CF₃ (propyl-CF₃) | CH₃ | F | 23 |

TABLE 2-continued

I

R¹HN-C(O)-C(R³)(R⁴)-C(O)-NHR²

| R¹ | R² | R³ | R⁴ | Example |
|---|---|---|---|---|
| N-methyl dibenzazepinone (H₃C-N, CH₃ substituent) | CF₃CF(F)- | CH₃ | F | 24 |
| benzodiazepine (NH, N-CH₃, =O) | CF₃CF(F)- | CH₃ | H | 25 |
| N-benzoyl benzodiazepinone (N-CH₃, =O) | CF₃CF(F)- | CH₃ | H | 26 |
| N-benzoyl benzodiazepinone (N-CH₃, =O) | CF₃CH₂- | CH₃ | CH₃ | 27 |
| N-(4-fluorobenzoyl) benzodiazepinone | CF₃CF(F)- | CH₃ | H | 28 |
| N-(4-chlorobenzoyl) benzodiazepinone | CF₃CF(F)- | CH₃ | H | 29 |

TABLE 2-continued

I

R¹HN—C(O)—C(R³)(R⁴)—C(O)—NHR²

| R¹ | R² | R³ | R⁴ | Example |
|---|---|---|---|---|
| (1-methyl-5-(3,5-difluorobenzoyl)-2,3,4,5-tetrahydro-1H-benzo[b][1,4]diazepin-3-yl) | CH₂C(F)(F)CF₃ | CH₃ | H | 30 |
| (5-methyl-6-oxo-6,7-dihydro-5H-dibenzo[b,d]azepin-7-yl) | CH(CF₃)C(CH₃)₃, with OH | CH₃ | CH₃ | 31 |
| (5-methyl-6-oxo-6,7-dihydro-5H-dibenzo[b,d]azepin-7-yl) | CH₂CH₂F | CH₃ | F | 32 |
| (5-methyl-6-oxo-6,7-dihydro-5H-dibenzo[b,d]azepin-7-yl) | CH₂CHF₂ (propyl-CHF₂) | CH₃ | F | 33 |
| (5-methyl-6-oxo-6,7-dihydro-5H-dibenzo[b,d]azepin-7-yl) | (2-fluorocyclopropyl) | CH₃ | F | 34 |
| (5-methyl-6-oxo-6,7-dihydro-5H-dibenzo[b,d]azepin-7-yl) | CH₂C(F)(F)CF₃ | CH₃ | F | 35 |

TABLE 2-continued
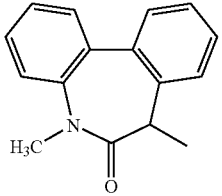
I
| R¹ | R² | R³ | R⁴ | Example |
|---|---|---|---|---|
| 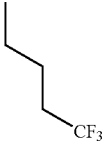 | 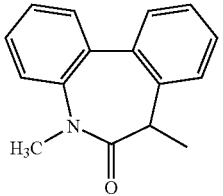 | CH₃ | F | 36 |
| 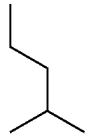 | 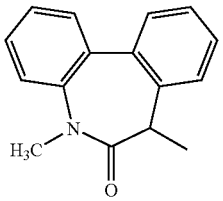 | CH₃ | F | 37 |
| 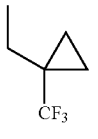 | 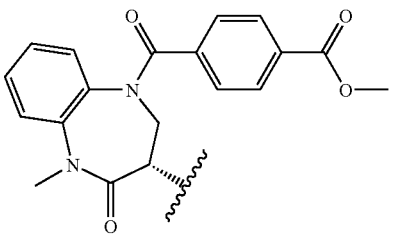 | CH₃ | F | 38 |
| 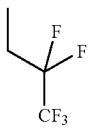 | 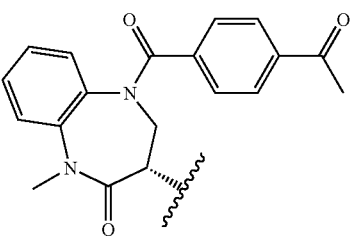 | CH₃ | H | 39 |
| 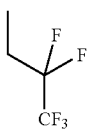 | 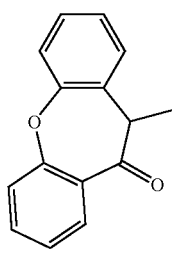 | CH₃ | H | 40 |
| 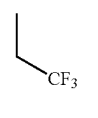 | | CH₃ | H | 41 |

TABLE 2-continued

I $$R^1HN-\overset{O}{C}-\overset{R^3\ R^4}{\underset{}{C}}-\overset{O}{C}-NHR^2$$

| R¹ | R² | R³ | R⁴ | Example |
|---|---|---|---|---|
| (dibenzoxepinone with methyl) | CF₃CF₂CH(F)- type group | CH₃ | H | 42 |
| (N-methyl dibenzazepinone with methyl) | CH₃O-CH(CF₃)-CH₂CH₂CH₃ | CH₃ | H | 43 |
| (N-methyl dibenzazepinone with methyl) | CHF₂-CF₂-CH₂CH₂CH₃ | CH₃ | H | 44 |
| (N-methyl dibenzazepinone with methyl) | iPrO-CH₂CH₂CH₂- | CH₃ | H | 45 |
| (N-cyclopropylmethyl benzodiazepinone with methyl) | CF₃CF₂CH₂- | CH₃ | H | 46 |
| (N,N'-dimethyl benzodiazepinone with methyl) | CF₃CF₂CH₂- | CH₃ | H | 47 |

TABLE 2-continued

|  |  |  |  | I |
|---|---|---|---|---|
| R¹ | R² | R³ | R⁴ | Example |
| [benzodiazepinone with N-cyclopropanecarbonyl and N-CH₃, methyl substituent] | CH(CF₃)F with CH₂ | CH₃ | H | 48 |
| [benzodiazepinone with N-(4-fluorobenzyl) and N-CH₃, methyl substituent] | CH(CF₃)F with CH₂ | CH₃ | H | 49 |
| [benzodiazepinone with N-(4-chlorobenzoyl) and N-cyclopropylmethyl, methyl substituent] | CH(CF₃)F with CH₂ | CH₃ | H | 50 |
| [dibenzazepinone with N-cyclopropylmethyl, methyl substituent] | CH(CF₃)F with CH₂ | CH₃ | H | 51 |
| [benzodiazepinone with N-acetyl and NH, methyl substituent] | CH(CF₃)F with CH₂ | CH₃ | H | 52 |

TABLE 2-continued
$$\underset{R^3}{\overset{R^1HN}{\longrightarrow}}\underset{R^4}{\overset{O}{\longrightarrow}}\underset{}{\overset{O}{\longrightarrow}}NHR^2 \qquad I$$
| R¹ | R² | R³ | R⁴ | Example |
|---|---|---|---|---|
| 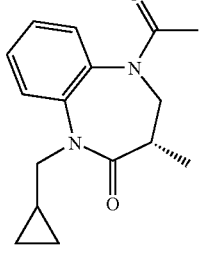 | 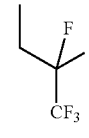 | CH₃ | H | 53 |
| 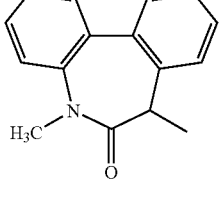 | 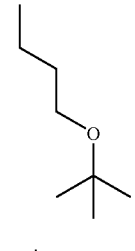 | CH₃ | H | 54 |
| 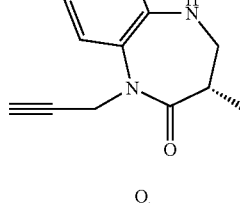 | 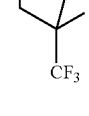 | CH₃ | H | 55 |
| 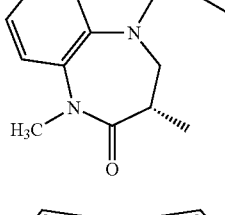 | 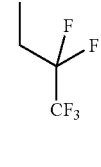 | CH₃ | H | 56 |
| 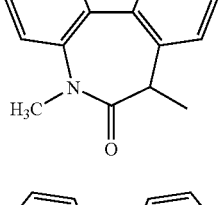 | 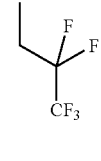 | CH₂CH₃ | H | 57 |
| 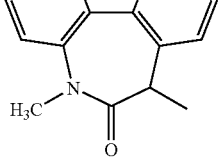 | 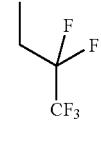 | CH(CH₃)₂ | H | 58 |

TABLE 2-continued
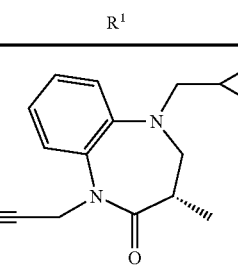
| R¹ | R² | R³ | R⁴ | Example |
|---|---|---|---|---|
| 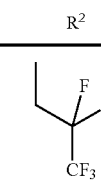 | 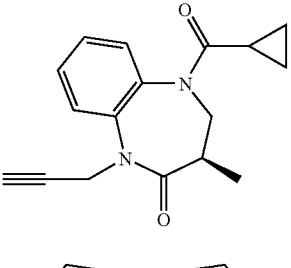 | CH₃ | H | 59 |
|  | 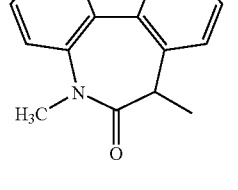 | CH₃ | H | 60 |
|  | 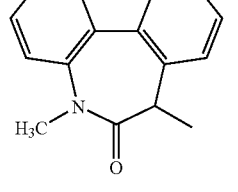 | H | H | 61 |
|  | 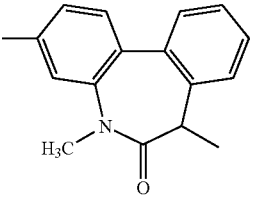 | CH₃ | CH₃ | 62 |
|  | 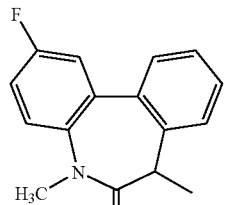 | CH₃ | H | 63 |
| 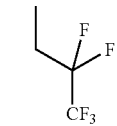 | | CH₃ | H | 64 |

TABLE 2-continued
I
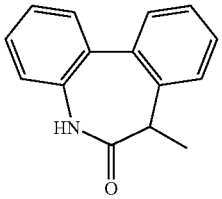
| R¹ | R² | R³ | R⁴ | Example |
|---|---|---|---|---|
| 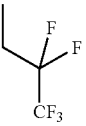 | 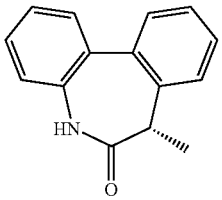 | CH₃ | H | 65 |
| 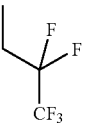 | 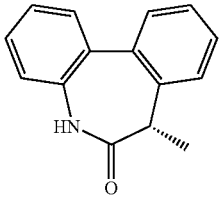 | H | H | 66 |
| 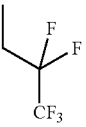 | 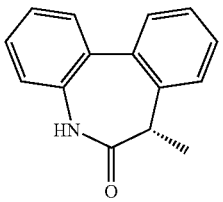 | CH₃ | CH₃ | 67 |
| 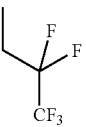 | 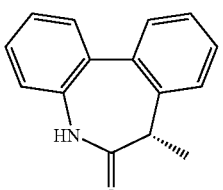 | OCH₃ | H | 68 |
| 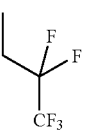 | 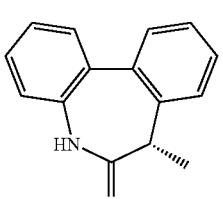 | ◂F | ⋯⋯ⅠⅠCH₃ | 69 |
| 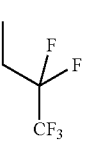 | | ⋯⋯ⅠⅠF | ◂CH₃ | 70 |

TABLE 2-continued

| R¹ | R² | R³ | R⁴ | Example |
|---|---|---|---|---|
| (N-cyclopropylmethyl dibenzazepinone) | CH₂C(F)(F)CF₃ | H | H | 71 |
| (N-cyclopropylmethyl dibenzazepinone) | CH₂C(F)(F)CF₃ | ◀CH₃ | H | 72 |
| (N-cyclopropylmethyl dibenzazepinone) | CH₂C(F)(F)CF₃ | ⋯⫼CH₃ | H | 73 |
| (N-cyclopropylmethyl dibenzazepinone) | CH₂C(F)(F)CF₃ | CH₃ | CH₃ | 74 |
| (N-cyclopropylmethyl dibenzazepinone) | CH₂C(F)(F)CF₃ | ◀F | ⋯⫼CH₃ | 75 |
| (N-cyclopropylmethyl dibenzazepinone) | CH₂C(F)(F)CF₃ | OCH₃ | H | 76 |

TABLE 2-continued

| R¹ | R² | R³ | R⁴ | Example |
|---|---|---|---|---|
| (dibenzazepinone with N-CH2-cyclopropyl, CH3) | (CH2CH2C(F)(F)CF3) | H | H | 77 |
| (dibenzazepinone with N-CH2-cyclopropyl, CH3) | (CH2CH2C(F)(F)CF3) | CH₃ | H | 78 |
| (dibenzazepinone with N-CH2-cyclopropyl, CH3) | (CH2CH2C(F)(F)CF3) | CH₃ | CH₃ | 79 |
| (dibenzazepinone with N-CH2-cyclopropyl, CH3) | (CH2CH2C(F)(F)CF3) | F | CH₃ | 80 |
| (dibenzazepinone with N-isopropyl, CH3) | (CH2C(F)(F)CF3) | H | CH₃ | 81 |
| (dibenzazepinone with N-isopropyl, CH3) | (CH2C(F)(F)CF3) | CH₃ | CH₃ | 82 |

TABLE 2-continued

R¹HN-C(=O)-C(R³)(R⁴)-C(=O)-NHR²   I

| R¹ | R² | R³ | R⁴ | Example |
|---|---|---|---|---|
| (N-methyl dibenzazepinone) | CH(CF₃)(CHF₂) | H | H | 83 |
| (N-methyl dibenzazepinone) | CH(CF₃)(CHF₂) | CH₃ | CH₃ | 84 |
| (N-methyl dibenzazepinone) | CH(CF₃)(CHF₂) | F (wedge) | CH₃ (dash) | 85 |
| (N-methyl dibenzazepinone) | CH(CF₃)(CHF₂) | F (dash) | CH₃ (wedge) | 86 |
| (N-methyl dibenzazepinone) | CH(CF₃)(CHF₂) | OCH₃ | H | 87 |
| (N-methyl dibenzazepinone) | CH(CF₃)(CH₂CH₃)... (CHF₂ variant) | H | H | 88 |

TABLE 2-continued

I

R¹HN–C(O)–C(R³)(R⁴)–C(O)–NHR²

| R¹ | R² | R³ | R⁴ | Example |
|---|---|---|---|---|
| (dibenzazepinone with N-CH₂CF₃) | CH₂C(F)(F)CF₃ | CH₃ | CH₃ | 89 |
| (N-methyl dibenzazepinone) | CH₂C(F)(F)CF₃ | F | CH₃ | 90 |
| (N-methyl dibenzazepinone) | CH₂C(F)(F)CF₃ | ◀F | ⅲCH₃ | 91 |
| (N-methyl dibenzazepinone) | CH₂C(F)(F)CF₃ | ⅲF | ◀CH₃ | 92 |
| (N-methyl dibenzazepinone) | CH₂C(F)(F)CF₃ | CH₃ | H | 93 |
| (N-methyl dibenzazepinone) | CH₂C(F)(F)CF₃ | CH₃ | CH₃ | 94 |

TABLE 2-continued

I

R¹HN-C(=O)-C(R³)(R⁴)-C(=O)-NHR²

| R¹ | R² | R³ | R⁴ | Example |
|---|---|---|---|---|
| [2,3,4,5-tetrahydro-1-(trifluoromethylsulfonyl)-1H-1,5-benzodiazepin-3-yl, 5-methyl-4-oxo] | CH(CF₃)(CHF₂) (1,1,1,3,3-pentafluoropropan-2-yl) | CH₃ | H | 95 |
| [1-formyl-2,3,4,5-tetrahydro-1H-1,5-benzodiazepin-3-yl, 5-methyl-4-oxo] | CH(CF₃)(CHF₂) | CH₃ | H | 96 |
| [1-(fluoroacetyl)-2,3,4,5-tetrahydro-1H-1,5-benzodiazepin-3-yl, 5-methyl-4-oxo] | CH(CF₃)(CHF₂) | CH₃ | H | 97 |
| [1-(trifluoroacetyl)-2,3,4,5-tetrahydro-1H-1,5-benzodiazepin-3-yl, 5-methyl-4-oxo] | CH(CF₃)(CHF₂) | CH₃ | H | 98 |
| [1-(methoxyacetyl)-2,3,4,5-tetrahydro-1H-1,5-benzodiazepin-3-yl, 5-methyl-4-oxo] | CH(CF₃)(CHF₂) | CH₃ | H | 99 |

TABLE 2-continued

Structure I: R¹HN-C(=O)-CR³R⁴-C(=O)-NHR²

| R¹ | R² | R³ | R⁴ | Example |
|---|---|---|---|---|
| [2,2,2-trifluoroethyl-N, methylsulfonyl-N, benzodiazepinone] | CH₂CF(F)CF₃ | CH₃ | H | 100 |
| [2,2,2-trifluoroethyl-N, trifluoromethylsulfonyl-N, benzodiazepinone] | CH₂CF(F)CF₃ | CH₃ | H | 101 |
| [2,2,2-trifluoroethyl-N, trifluoroacetyl-N, benzodiazepinone] | CH₂CF(F)CF₃ | CH₃ | H | 102 |
| [methyl-N, methylsulfonyl-N, benzodiazepinone] | CH₂CF(F)CF₃ | CH₃ | H | 103 |
| [methyl-N, pivaloyl-N, benzodiazepinone] | CH₂CF(F)CF₃ | H | H | 104 |

TABLE 2-continued

I $$R^1HN-\underset{R^3}{\underset{|}{C}}(=O)-\underset{R^4}{\underset{|}{C}}-C(=O)-NHR^2$$

| R¹ | R² | R³ | R⁴ | Example |
|---|---|---|---|---|
| (1-methyl-5-oxo-4-yl of 1-pivaloyl-2,3,4,5-tetrahydro-1H-1,5-benzodiazepine) | CF₃-CF₂-CHF- | CH₃ | H | 105 |
| (1-(cyclopropylmethoxycarbonyl)-5-methyl-4-oxo-3-yl of benzodiazepine) | CF₃-CF₂-CHF- | CH₃ | H | 106 |
| (1-acetyl-5-(2,2,2-trifluoroethyl)-4-oxo-3-yl of benzodiazepine) | CF₃-CF₂-CHF- | CH₃ | H | 107 |
| (1-(cyclopropylcarbonyl)-5-(2,2,2-trifluoroethyl)-4-oxo-3-yl) | CF₃-CF₂-CHF- | CH₃ | H | 108 |
| (1-(cyclopropylmethoxycarbonyl)-5-(2,2,2-trifluoroethyl)-4-oxo-3-yl) | CF₃-CF₂-CHF- | CH₃ | H | 109 |

TABLE 2-continued

| R¹ | R² | R³ | R⁴ | Example |
|---|---|---|---|---|
| 1-acetyl-5-methyl-2,3,4,5-tetrahydro-1H-benzo[b][1,4]diazepin-4-yl (4-oxo) | CH₂C(F)(F)CF₃ | F | CH₃ | 110 |
| 1-acetyl-5-ethyl-2,3,4,5-tetrahydro-1H-benzo[b][1,4]diazepin-4-yl (4-oxo) | CH₂C(F)(F)CF₃ | CH₃ | CH₃ | 111 |
| 1-acetyl-5-ethyl-2,3,4,5-tetrahydro-1H-benzo[b][1,4]diazepin-4-yl (4-oxo) | CH₂C(F)(F)CF₃ | CH₃ | H | 112 |
| 1-acetyl-5-isopropyl-2,3,4,5-tetrahydro-1H-benzo[b][1,4]diazepin-4-yl (4-oxo) | CH₂C(F)(F)CF₃ | CH₃ | H | 113 |
| 1-acetyl-5-benzyl-2,3,4,5-tetrahydro-1H-benzo[b][1,4]diazepin-4-yl (4-oxo) | CH₂C(F)(F)CF₃ | CH₃ | CH₃ | 114 |
| 1-acetyl-5-benzyl-pyrido-fused-diazepinone | CH₂C(F)(F)CF₃ | CH₃ | H | 115 |

TABLE 2-continued
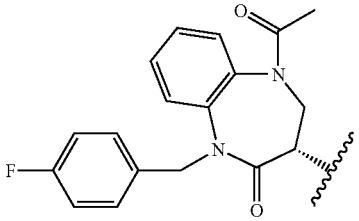
| R¹ | R² | R³ | R⁴ | Example |
|---|---|---|---|---|
| 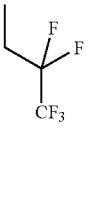 | 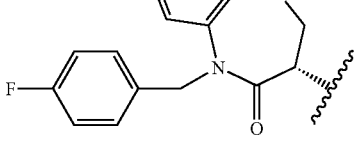 | CH₃ | CH₃ | 116 |
| 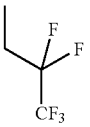 | 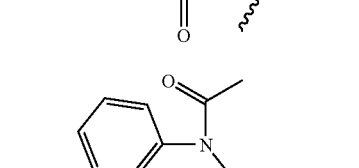 | CH₃ | H | 117 |
| 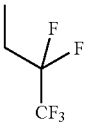 | 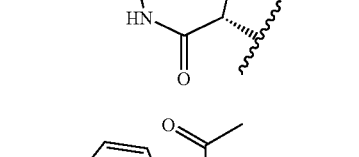 | ◀CH₃ | H | 118 |
| 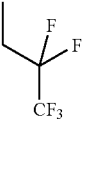 | 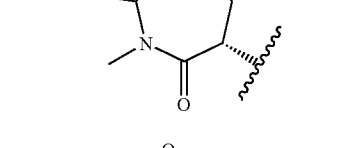 | ·······CH₃ | H | 119 |
| 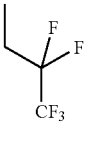 | 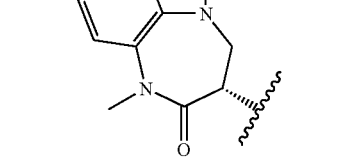 | ◀CH₃ | H | 120 |
| 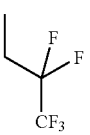 | | ·······CH₃ | H | 121 |

TABLE 2-continued

| | I |
|---|---|

Structure: R¹HN-C(=O)-C(R³)(R⁴)-C(=O)-NHR²

| R¹ | R² | R³ | R⁴ | Example |
|---|---|---|---|---|
| (methyl-dihydrodibenzazepinone) | CH(CF₃)CH₂CH₂CH₃ type | CH₃ | CH₃ | 122 |
| (methyl-dihydrodibenzazepinone) | CH(CF₃)CH₂CH₂CH₃ type | ·····ıF | ◀CH₃ | 123 |
| (methyl-dihydrodibenzazepinone) | CH(CF₃)CH₂CH₂CH₃ type | ·····ıCH₃ | ◀F | 124 |
| (methyl-dihydrodibenzazepinone) | CH₂CH₂CH₂CF₃ | ◀F | ·····ıCH₃ | 125 |

The invention claimed is:

1. A compound of formula

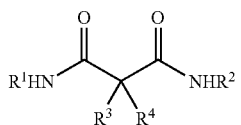

I wherein
R¹ is selected from a)

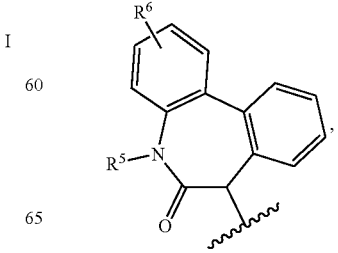

,

-continued b)

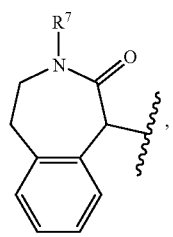

c)

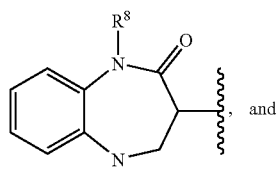, and d)

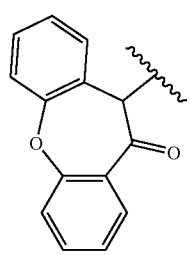

R² is lower alkyl, lower alkinyl, —(CH₂)ₙ—O-lower alkyl, —(CH₂), —S-lower alkyl, —(CH₂)ₙ—CN, —(CR'R")ₙ—CF₃, —(CR'R")ₙ—CHF₂, —(CR'R")ₙ—CH₂F, —(CH₂)ₙ—C(O)O-lower alkyl, —(CH₂)ₙ-halogen, or is —(CH₂)ₙ-cycloalkyl optionally substituted by one or more substituents selected from the group consisting of phenyl, halogen and CF₃;

R',R" are each independently hydrogen, lower alkyl, lower alkoxy, halogen or hydroxy;

R³, R⁴ are each independently hydrogen, lower alkyl, lower alkoxy, phenyl or halogen;

R⁵ is hydrogen, lower alkyl, —(CH₂)ₙ—CF₃ or —(CH₂)ₙ-cycloalkyl;

R⁶ is hydrogen or halogen;

R⁷ is hydrogen or lower alkyl;

R⁸ is hydrogen, lower alkyl, lower alkinyl, —(CH₂)ₙ—CF₃, —(CH₂)ₙ-cycloalkyl or —(CH₂)ₙ-phenyl optionally substituted by halogen;

R⁹ is hydrogen, lower alkyl, —C(O)H, —C(O)-lower alkyl, —C(O)—CF₃, —C(O)—CH₂F, —C(O)—CHF₂, —C(O)-cycloalkyl, —C(O)—(CH₂)ₙ—O-lower alkyl, —C(O)O—(CH₂)ₙ-cycloalkyl, —C(O)-phenyl optionally substituted by one or more substituents selected from the group consisting of halogen and —C(O)O-lower alkyl, or is —S(O)₂-lower alkyl, —S(O)₂—CF₃ —(CH₂)ₙ-cycloalkyl or is —(CH₂)ₙ— phenyl optionally substituted by halogen;

n is 0, 1, 2, 3 or 4;

or a pharmaceutically acceptable acid addition salt, optically pure enantiommer, racemate or diastereomeric mixture thereof.

2. A compound of formula

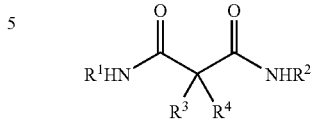

I-1 wherein

R¹ is selected from a)

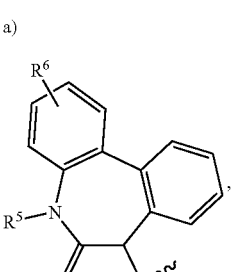

b)

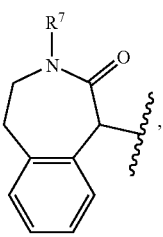, c)

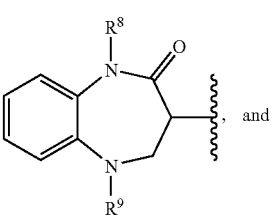, and d)

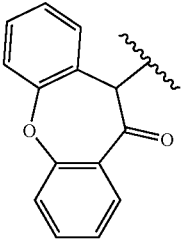

R² is lower alkyl, lower alkinyl, —(CH₂)ₙ—O-lower alkyl, —(CH₂)ₙ—S-lower alkyl, —(CH₂)ₙ—CN, —(CR'R")ₙ—CF₃, —(CR'R")ₙ—CHF₂, —(CH₂)ₙ—C(O)O-lower alkyl, —(CH₂)ₙ-halogen, or is —(CH₂)ₙ-cycloalkyl optionally substituted by one or more substituents selected from the group consisting of phenyl, halogen and CF₃;

R',R" are each independently hydrogen, lower alkyl, lower alkoxy, halogen or hydroxy;

R³, R⁴ are each independently hydrogen, lower alkyl, phenyl or halogen;
$R^5$ is lower alkyl or —(CH$_2$)$_2$-cycloalkyl;
$R^6$ is hydrogen or halogen;
$R^7$ is hydrogen or lower alkyl;
$R^8$ is hydrogen, lower alkyl, lower alkinyl or —(CH$_2$)$_2$-cycloalkyl;
$R^9$ is hydrogen, lower alkyl, —C(O)-lower alkyl, —C(O)-lower cycloalkyl, —(CH$_2$)$_n$-cycloalkyl, phenyl, —C(O)-phenyl optionally substituted by one or more substituents selected from the group consisting of halogen and —C(O)O-lower alkyl, or is (CH$_2$)$_2$-phenyl optionally substituted by halogen;
n is 0, 1, 2, 3 or 4;
or a pharmaceutically acceptable acid addition salt, optically pure enantiommer, racemate or diastereomeric mixture thereof.

3. A compound of formula I in accordance with claim 1, wherein R¹ is a).

4. A compound of formula I in accordance with claim 3, wherein R² is —(CH$_2$)$_n$-cycloalkyl optionally substituted by CF$_3$.

5. A compound of formula I in accordance with claim 4, wherein the compound is
N-cyclopropylmethyl-2-methyl-N'-(5-methyl-6-oxo-6,7-dihydro-5H-dibenzo[b,d]azepin-7-yl)-malonamide or
2-fluoro-2-methyl-N-(5-methyl-6-oxo-6,7-dihydro-5H-dibenzo[b,d]azepin-7-yl)-N'-(1-trifluoromethyl-cyclopropylmethyl)-malonamide.

6. A compound of formula I in accordance with claim 3, wherein R² is lower alkyl, —(CH$_2$)$_n$—O-lower alkyl or —(CH$_2$)$_n$—S-lower alkyl.

7. A compound of formula I in accordance with claim 6, wherein the compound is
2-methyl-N-(5-methyl-6-oxo-6,7-dihydro-5H-dibenzo[b,d]azepin-7-yl)-N'-(2-methoxyethyl)-malonamide,
2-methyl-N-(5-methyl-6-oxo-6,7-dihydro-5H-dibenzo[b,d]azepin-7-yl)-N'-(2-methylthioethyl)-malonamide,
2-methyl-N-(5-methyl-6-oxo-6,7-dihydro-5H-dibenzo[b,d]azepin-7-yl)-N'-(3-methoxy-propyl)-malonamide,
2-methyl-N-(5-methyl-6-oxo-6,7-dihydro-5H-dibenzo[b,d]azepin-7-yl)-N'-propyl-malonamide or
2-fluoro-2-methyl-N-(3-methyl-butyl)-N'-(5-methyl-6-oxo-6,7-dihydro-5H-dibenzo[b,d]azepin-7-yl)-malonamide.

8. A compound of formula I in accordance with claim 3, wherein R² is —(CR'R")$_n$—CF$_3$ or —(CR'R")$_n$—CHF$_2$.

9. A compound of formula I in accordance with claim 8, wherein the compound is
2-methyl-N-(5-methyl-6-oxo-6,7-dihydro-5H-dibenzo[b,d]azepin-7-yl)-N'-(2,2,2-trifluoroethyl)-malonamide,
2-methyl-N-(5-methyl-6-oxo-6,7-dihydro-5H-dibenzo[b,d]azepin-7-yl)-N'-(3,3,3-trifluoro-propyl)-malonamide,
2-fluoro-2-methyl-N-(5-methyl-6-oxo-6,7-dihydro-5H-dibenzo[b,d]azepin-7-yl)-N'-(2,2,2-trifluoro-ethyl)-malonamide,
2-fluoro-2-methyl-N-(5-methyl-6-oxo-6,7-dihydro-5H-dibenzo[b,d]azepin-7-yl)-N'-(2,2,3,3,3-pentafluoro-propyl)-malonamide,
2-fluoro-2-methyl-N-(5-methyl-6-oxo-6,7-dihydro-5H-dibenzo[b,d]azepin-7-yl)-N'-(3,3,4,4-tetrafluoro-butyl)-malonamide,
2-fluoro-2-methyl-N-(5-methyl-6-oxo-6,7-dihydro-5H-dibenzo[b,d]azepin-7-yl)-N'-(4,4,4-trifluoro-butyl)-malonamide,
2-methyl-N-(5-methyl-6-oxo-6,7-dihydro-5H-dibenzo[b,d]azepin-7-yl)-N'-(4,4,4-trifluoro-3-methoxy-butyl)-malonamide,
2-fluoro-2-methyl-N-(5-methyl-6-oxo-6,7-dihydro-5H-dibenzo[b,d]azepin-7-yl)-N'-(3,3,4,4-tetrafluoro-butyl)-malonamide, or
N-(5-cyclopropylmethyl-6-oxo-6,7-dihydro-5H-dibenzo[b,d]azepin-7-yl)-2-methyl-N'-(2,2,3,3,3-pentafluoro-propyl)-malonamide.

10. A compound of formula I in accordance with claim 8, wherein the compound is
2-methyl-N-(6-oxo-6,7-dihydro-5H-dibenzo[b,d]azepin-7-yl)-N'-(2,2,3,3,3-pentafluoro-propyl)-malonamide,
N-((S)-6-oxo-6,7-dihydro-5H-dibenzo[b,d]azepin-7-yl)-N'-(2,2,3,3,3-pentafluoro-propyl)-malonamide,
2,2-dimethyl-N-((S)-6-oxo-6,7-dihydro-5H-dibenzo[b,d]azepin-7-yl)-N'-(2,2,3,3,3-pentafluoro-propyl)-malonamide,
(−)-2-methoxy-N-(6-oxo-6,7-dihydro-5H-dibenzo[b,d]azepin-7-yl)-N'-(2,2,3,3,3-pentafluoro-propyl)-malonamide,
(2R)-2-fluoro-2-methyl-N-((S)-6-oxo-6,7-dihydro-5H-dibenzo[b,d]azepin-7-yl)-N'-(2,2,3,3,3-pentafluoro-propyl)-malonamide,
(2S)-2-fluoro-2-methyl-N-[(S)-6-oxo-6,7-dihydro-5H-dibenzo[b,d]azepin-7-yl]-N'-(2,2,3,3,3-pentafluoro-propyl)-malonamide,
N-((S)-5-cyclopropylmethyl-6-oxo-6,7-dihydro-5H-dibenzo[b,d]azepin-7-yl)-N'-(2,2,3,3,3-pentafluoro-propyl)-malonamide,
(R)-N-((S)-5-cyclopropylmethyl-6-oxo-6,7-dihydro-5H-dibenzo[b,d]azepin-7-yl)-2-methyl-N'-(2,2,3,3,3-pentafluoro-propyl)-malonamide, or
(S)-N-((S)-5-cyclopropylmethyl-6-oxo-6,7-dihydro-5H-dibenzo[b,d]azepin-7-yl)-2-methyl-N'-(2,2,3,3,3-pentafluoro-propyl)-malonamide.

11. A compound of formula I in accordance with claim 8, wherein the compound is
N-((S)-5-cyclopropylmethyl-6-oxo-6,7-dihydro-5H-dibenzo[b,d]azepin-7-yl)-2,2-dimethyl-N'-(2,2,3,3,3-pentafluoro-propyl)-malonamide,
(R)-N-((S)-5-cyclopropylmethyl-6-oxo-6,7-dihydro-5H-dibenzo[b,d]azepin-7-yl)-2-fluoro-2-methyl-N'-(2,2,3,3,3-pentafluoro-propyl)-malonamide,
N-((S)-5-cyclopropylmethyl-6-oxo-6,7-dihydro-5H-dibenzo[b,d]azepin-7-yl)-2-methoxy-N'(2,2,3,3,3-pentafluoro-propyl)-malonamide,
N-((S)-5-cyclopropylmethyl-6-oxo-6,7-dihydro-5H-dibenzo[b,d]azepin-7-yl)-N'-(3,3,4,4,4-pentafluoro-butyl)-malonamide,
N-((S)-5-cyclopropylmethyl-6-oxo-6,7-dihydro-5H-dibenzo[b,d]azepin-7-yl)-2-methyl-N'-(3,3,4,4,4-pentafluoro-butyl)-malonamide,
N-((S)-5-cyclopropylmethyl-6-oxo-6,7-dihydro-5H-dibenzo[b,d]azepin-7-yl)-2,2-dimethyl-N'-(3,3,4,4,4-pentafluoro-butyl)-malonamide,
(R)-N-((S)-5-cyclopropylmethyl-6-oxo-6,7-dihydro-5H-dibenzo[b,d]azepin-7-yl)-2-fluoro-2-methyl-N'-(3,3,4,4,4-pentafluoro-butyl)-malonamide, or
N-(5-isopropyl-6-oxo-6,7-dihydro-5H-dibenzo[b,d]azepin-7-yl)-2-methyl-N'-(2,2,3,3,3-pentafluoro-propyl)-malonamide.

12. A compound of formula I in accordance with claim 8, wherein the compound is
N-(5-isopropyl-6-oxo-6,7-dihydro-5H-dibenzo[b,d]azepin-7-yl)-2,2-dimethyl-N'-(2,2,3,3,3-pentafluoro-propyl)-malonamide, N-((S)-5-methyl-6-oxo-6,7-dihydro-5H-dibenzo[b,d]
azepin-7-yl)-N'-(2,2,3,3,3-pentafluoro-propyl)-malonamide,
2,2-dimethyl-N-((S)-5-methyl-6-oxo-6,7-dihydro-5H-
dibenzo[b,d]azepin-7-yl)-N-(2,2,3,3,3-pentafluoro-propyl)-malonamide,
(2R)-2-fluoro-2-methyl-N-[(S)-5-methyl-6-oxo-6,7-dihydro-5H-dibenzo[b,d]azepin-7-yl]-N'-(2,2,3,3,3-pentafluoro-propyl)-malonamide,
(2S)-2-fluoro-2-methyl-N-[(S)-5-methyl-6-oxo-6,7-dihydro-5H-dibenzo[b,d]azepin-7-yl]-N'-(2,2,3,3,3-pentafluoro-propyl)-malonamide,
2-methoxy-N-((S)-5-methyl-6-oxo-6,7-dihydro-5H-dibenzo[b,d]azepin-7-yl)-N'-(2,2,3,3,3-pentafluoro-propyl)-malonamide,
N-((S)-5-methyl-6-oxo-6,7-dihydro-5H-dibenzo[b,d]
azepin-7-yl)-N'-(3,3,4,4,4-pentafluoro-butyl)-malonamide or
2,2-dimethyl-N-[(S)-6-oxo-5-(2,2,2-trifluoro-ethyl)-6,7-dihydro-5H-dibenzo[b,d]azepin-7-yl]-N'-(2,2,3,3,3-pentafluoro-propyl)-malonamide.

13. A compound of formula I in accordance with claim 1, wherein $R^1$ is b).

14. A compound of formula I in accordance with claim 13, wherein the compound is 2-methyl-N-(3-methyl-2-oxo-2,3,4,5-tetrahydro-1H-benzo[d]azepin-1-yl)-N'-(2,2,2-trifluoro-ethyl)-malonamide.

15. A compound of formula I in accordance with claim 1, wherein $R^1$ is c).

16. A compound of formula I in accordance with claim 15, wherein $R^2$ is —(CR'R")$_n$—CF$_3$.

17. A compound of formula I in accordance with claim 16, wherein the compound is
2-methyl-N-(1-methyl-2-oxo-5-phenyl-2,3,4,5-tetrahydro-1H-benzo[b][1,4]diazepin-3-yl)-N'-(2,2,2-trifluoro-ethyl)-malonamide,
N-((3S)-5-benzoyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide,
N-[(3S)-5-(4-fluoro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide,
N-[(3S)-5-(4-chloro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide,
N-[(3S)-5-(3,5-difluoro-benzoyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide,
4-{(3S)-5-methyl-4-oxo-3-[2-(2,2,3,3,3-pentafluoro-propylcarbamoyl)-propionylamino]-2,3,4,5-tetrahydro-benzo[b][1,4]diazepine-1-carbonyl}-benzoic acid methyl ester,
N-((3S)-5-acetyl-1-methyl-2-oxo-2,3,4,5-tetrahydro-1H-benzo[b][1,4]diazepin-3-yl)-2-methyl-N'-(2,2,3,3,3-pentafluoro-propyl)-malonamide,
N-[5-((3S)-4-fluoro-benzyl)-1-methyl-2-oxo-2,3,4,5-tetrahydro-1H-benzo[b][1,4]diazepin-3-yl]-2-methyl-N'-(2,2,3,3,3-pentafluoro-propyl)-malonamide,
N-[(3S)-5-(4-chloro-benzoyl)-1-cyclopropylmethyl-2-oxo-2,3,4,5-tetrahydro-1H-benzo[b][1,4]diazepin-3-yl]-2-methyl-N'-(2,2,3,3,3-pentafluoro-propyl)-malonamide, or
(2RS)-methyl-N-((3S)-1-methyl-2-oxo-5-trifluoromethanesulfonyl-2,3,4,5-tetrahydro-1H-benzo[b][1,4]diazepin-3-yl)-N'-(2,2,3,3,3-pentafluoro-propyl)-malonamide.

18. A compound of formula I in accordance with claim 16, wherein the compound is
(2RS)-methyl-N-[(3S)-1-methyl-2-oxo-5-(2,2,2-trifluoro-acetyl)-2,3,4,5-tetrahydro-1H-benzo[b][1,4]diazepin-3-yl]-N'-(2,2,3,3,3-pentafluoro-propyl)-malonamide,
N-[(3S)-5-(2-methoxy-acetyl)-1-methyl-2-oxo-2,3,4,5-tetrahydro-1H-benzo[b][1,4]diazepin-3-yl]-(2RS)-methyl-N'-(2,2,3,3,3-pentafluoro-propyl)-malonamide,
N-[(S)-5-methanesulfonyl-2-oxo-1-(2,2,2-trifluoro-ethyl)-2,3,4,5-tetrahydro-1H-benzo[b][1,4]diazepin-3-yl]-(2RS)-methyl-N'-(2,2,3,3,3-pentafluoro-propyl)-malonamide,
(2RS)-methyl-N-[(S)-2-oxo-1-(2,2,2-trifluoro-ethyl)-5-trifluoromethanesulfonyl-2,3,4,5-tetrahydro-1H-benzo[b][1,4]diazepin-3-yl]-N'-(2,2,3,3,3-pentafluoro-propyl)-malonamide, 5-methyl-4-oxo-(3S)-[(2RS)-(2,2,3,3,3-pentafluoro-propylcarbamoyl)-propionylamino]-2,3,4,5-tetrahydro-benzo[b][1,4]diazepine-1-carboxylic acid cyclopropylmethyl estermalonamide,
N-[(S)-5-cyclopropanecarbonyl-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide, 4-oxo-(3S)-[(2RS)-(2,2,3,3,3-pentafluoro-propylcarbamoyl)-propionylamino]-5-(2,2,2-trifluoro-ethyl)-2,3,4,5-tetrahydro-benzo[b][1,4]diazepine-1-carboxylic acid cyclopropylmethyl ester,
N-[(S)-5-acetyl-1-isopropyl-2-oxo-2,3,4,5-tetrahydro-1H-benzo[b][1,4]diazepin-3-yl]-(2RS)-methyl-N'-(2,2,3,3,3-pentafluoro-propyl)-malonamide or
N-((S)-5-acetyl-1-benzyl-2-oxo-2,3,4,5-tetrahydro-1H-benzo[b][1,4]diazepin-3-yl)-(2RS)-methyl-N'-(2,2,3,3,3-pentafluoro-propyl)-malonamide.

19. A compound of formula I in accordance with claim 1, wherein $R^1$ is d).

20. A compound of formula I in accordance with claim 19, wherein the compound is
2-methyl-N-(11-oxo-10,11-dihydro-dibenzo[b,f]oxepin-10-yl)-N'-(2,2,2-trifluoro-ethyl)-malonamide or
2-methyl-N-(11-oxo-10,11-dihydro-dibenzo[b,f]oxepin-10-yl)-N'-(2,2,3,3,3-pentafluoro-propyl)-malonamide.

21. A composition comprising a compound of formula I wherein
$R^1$ is selected from a)

-continued b)

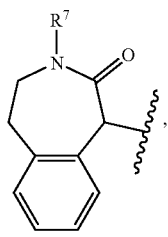

c)

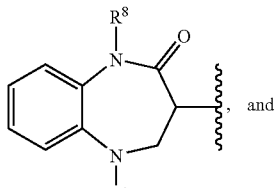, and d)

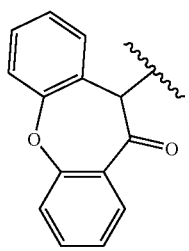

R² is lower alkyl, lower alkinyl, —(CH₂)ₙ—O-lower alkyl, —(CH₂)ₙ—S-lower alkyl, —(CH₂)ₙ—CN, —(CR'R")ₙ—CF₃, —(CR'R")ₙ—CHF₂, —(CR'R")ₙ—CH₂F, —(CH₂)ₙ—C(O)O-lower alkyl, —(CH₂)ₙ-halogen, or is —(CH₂)ₙ-cycloalkyl optionally substituted by one or more substituents selected from the group consisting of phenyl, halogen and CF₃;

R',R" are each independently hydrogen, lower alkyl, lower alkoxy, halogen or hydroxy;

R³, R⁴ are each independently hydrogen, lower alkyl, lower alkoxy, phenyl or halogen;

R⁵ is hydrogen, lower alkyl, —(CH₂)ₙ—CF₃ or —(CH₂)ₙ-cycloalkyl;

R⁶ is hydrogen or halogen;

R⁷ is hydrogen or lower alkyl;

R⁸ is hydrogen, lower alkyl, lower alkinyl, —(CH₂)ₙ—CF₃, —(CH₂)ₙ-cycloalkyl or —(CH₂)ₙ-phenyl optionally substituted by halogen;

R⁹ is hydrogen, lower alkyl, —C(O)H, —C(O)-lower alkyl, —C(O)—CF₃, —C(O)—CH₂F, —C(O)—CHF₂, —C(O)-cycloalkyl, —C(O)—(CH₂)ₙ—O-lower alkyl, —C(O)O—(CH₂)ₙ-cycloalkyl, —C(O)-phenyl optionally substituted by one or more substituents selected from the group consisting of halogen and —C(O)O-lower alkyl, or is —S(O)₂-lower alkyl, —S(O)₂—CF₃, —(CH₂)ₙ-cycloalkyl or is —(CH₂)ₙ— phenyl optionally substituted by halogen;

n is 0, 1, 2, 3 or 4;

or a pharmaceutically acceptable acid addition salt, optically pure enantiommer, racemate or diastereomeric mixture thereof and a pharmaceutically acceptable carrier.

22. A composition comprising a compound of formula

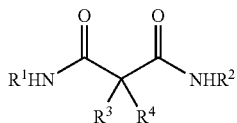

I-1 wherein

R¹ is selected from a)

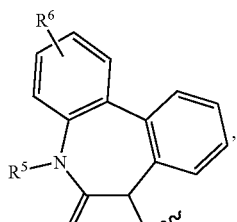

b)

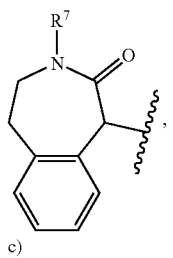

c)

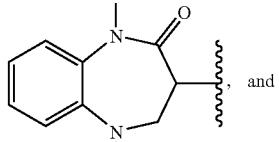, and d)

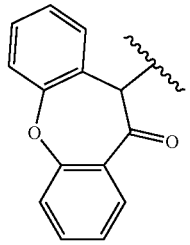

R² is lower alkyl, lower alkinyl, —(CH₂)ₙ—O-lower alkyl, —(CH₂)ₙ—S-lower alkyl, —(CH₂)ₙ—CN, —(CR'R")ₙ—CF₃, —(CR'R")ₙ—CHF₂, —(CH₂)ₙ—C(O)O-lower alkyl, —(CH₂)ₙ-halogen, or is —(CH₂)ₙ-cycloalkyl optionally substituted by one or more substituents selected from the group consisting of phenyl, halogen and CF₃;

R',R" are each independently hydrogen, lower alkyl, lower alkoxy, halogen or hydroxy;

$R^3$, $R^4$ are each independently hydrogen, lower alkyl, phenyl or halogen;

$R^5$ is lower alkyl or —$(CH)_2$-cycloalkyl;

$R^6$ is hydrogen or halogen;

$R^7$ is hydrogen or lower alkyl;

$R^8$ is hydrogen, lower alkyl, lower alkinyl or —$(CH)_2$-cycloalkyl;

$R^9$ is hydrogen, lower alkyl, —C(O)-lower alkyl, —C(O)-lower cycloalkyl, —$(CH_2)_n$-cycloalkyl, phenyl, —C(O)-phenyl optionally substituted by one or more substituents selected from the group consisting of halogen and —C(O)O-lower alkyl, or is $(CH)_2$-phenyl optionally substituted by halogen;

n is 0, 1, 2, 3 or 4;

or a pharmaceutically acceptable acid addition salt, optically pure enantiomer, racemate or diastereomeric mixture thereof and a pharmaceutically acceptable carrier.

23. A process for preparing a compound of formula

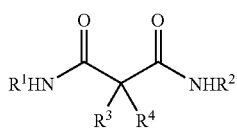

I wherein $R^1$ is selected from a)

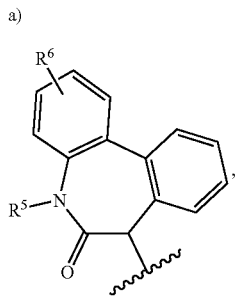

b)

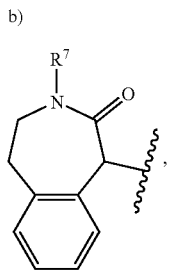

c)

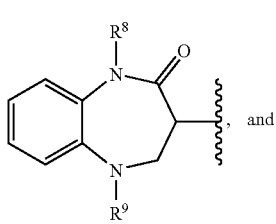
and d)

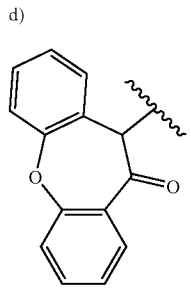

$R^2$ is lower alkyl, lower alkinyl, —$(CH_2)_n$—O-lower alkyl, —$(CH_2)_n$—S-lower alkyl, —$(CH_2)_n$—CN, —$(CR'R'')_n$—$CF_3$, —$(CR'R'')_n$—$CHF_2$, —$(CR'R'')_n$—$CH_2F$, —$(CH_2)_n$—C(O)O-lower alkyl, —$(CH_2)_n$-halogen, or is —$(CH_2)_n$-cycloalkyl optionally substituted by one or more substituents selected from the group consisting of phenyl, halogen and $CF_3$;

R',R'' are each independently hydrogen, lower alkyl, lower alkoxy, halogen or hydroxy;

$R^3$, $R^4$ are each independently hydrogen, lower alkyl, lower alkoxy, phenyl or halogen;

$R^5$ is hydrogen, lower alkyl, —$(CH_2)_n$—$CF_3$ or —$(CH_2)_n$-cycloalkyl;

$R^6$ is hydrogen or halogen;

$R^7$ is hydrogen or lower alkyl;

$R^8$ is hydrogen, lower alkyl, lower alkinyl, —$(CH_2)_n$—$CF_3$, —$(CH_2)_n$-cycloalkyl or —$(CH_2)_n$-phenyl optionally substituted by halogen;

$R^9$ is hydrogen, lower alkyl, —C(O)H, —C(O)-lower alkyl, —C(O)—$CF_3$, —C(O)—$CH_2F$, —C(O)—$CHF_2$, —C(O)-cycloalkyl, —C(O)—$(CH_2)_n$—O-lower alkyl, —C(O)O—$(CH_2)_n$-cycloalkyl, —C(O)-phenyl optionally substituted by one or more substituents selected from the group consisting of halogen and —C(O)O-lower alkyl, or is —$S(O)_2$-lower alkyl, —$S(O)_2$—$CF_3$, —$(CH_2)_n$-cycloalkyl or is —$(CH_2)_n$— phenyl optionally substituted by halogen; and n is 0, 1, 2, 3 or 4;

which process comprises reacting a compound of formula

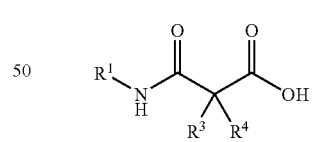

II with a compound of formula $NH_2R^2$    III to produce a compound of formula

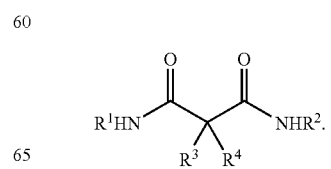

I

24. A method of treating Alzheimer's disease comprising administering to a patient having Alzheimer's disease a therapeutically effective amount of a compound of formula I

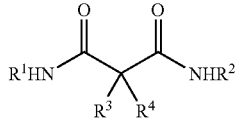

wherein

R¹ is selected from a)

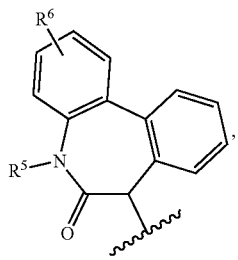

b)

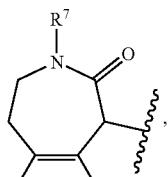

c)

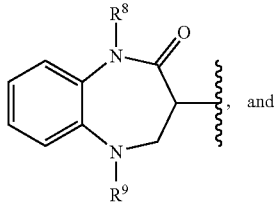, and d)

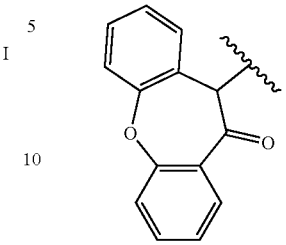

$R^2$ is lower alkyl, lower alkinyl, —$(CH_2)_n$—O-lower alkyl, —$(CH_2)_n$—S-lower alkyl, —$(CH_2)_n$—CN, —$(CR'R'')_n$—$CF_3$, —$(CR'R'')_n$—$CHF_2$, —(CR'R''), —$CH_2F$, —$(CH_2)_n$—C(O)O-lower alkyl, —$(CH_2)_n$-halogen, or is —$(CH_2)_n$-cycloalkyl optionally substituted by one or more substituents selected from the group consisting of phenyl, halogen and $CF_3$;

R',R" are each independently hydrogen, lower alkyl, lower alkoxy, halogen or hydroxy;

$R^3$, $R^4$ are each independently hydrogen, lower alkyl, lower alkoxy, phenyl or halogen;

$R^5$ is hydrogen, lower alkyl, —$(CH_2)_n$—$CF_3$ or —$(CH_2)_n$-cycloalkyl;

$R^6$ is hydrogen or halogen;

$R^7$ is hydrogen or lower alkyl;

$R^8$ is hydrogen, lower alkyl, lower alkinyl, —$(CH_2)_n$—$CF_3$, —$(CH_2)_n$-cycloalkyl or —$(CH_2)_n$-phenyl optionally substituted by halogen;

$R^9$ is hydrogen, lower alkyl, —C(O)H, —C(O)-lower alkyl, —C(O)—$CF_3$, —C(O)—$CH_2F$, —C(O)—$CHF_2$, —C(O)-cycloalkyl, —C(O)—$(CH_2)_n$—O-lower alkyl, —C(O)O—$(CH_2)_n$-cycloalkyl, —C(O)-phenyl optionally substituted by one or more substituents selected from the group consisting of halogen and —C(O)O-lower alkyl, or is —$S(O)_2$-lower alkyl, —$S(O)_2$—$CF_3$, —$(CH_2)_n$-cycloalkyl or is —$(CH_2)_n$— phenyl optionally substituted by halogen;

n is 0, 1, 2, 3 or 4;

or a pharmaceutically acceptable acid addition salt, optically pure enantiomer, racemate or diastereomeric mixture thereof.

* * * * *